US012673196B2

(12) United States Patent
Schultz

(10) Patent No.: US 12,673,196 B2
(45) Date of Patent: *Jul. 7, 2026

(54) MEDICAL CONNECTOR CONTAMINATION PREVENTION DEVICE

(71) Applicant: Joseph P. Schultz, Atlanta, GA (US)

(72) Inventor: Joseph P. Schultz, Atlanta, GA (US)

( * ) Notice: Subject to any disclaimer, the term of this patent is extended or adjusted under 35 U.S.C. 154(b) by 357 days.

This patent is subject to a terminal disclaimer.

(21) Appl. No.: 17/890,339

(22) Filed: Aug. 18, 2022

(65) Prior Publication Data

US 2023/0218881 A1     Jul. 13, 2023

Related U.S. Application Data

(63) Continuation of application No. 15/971,091, filed on May 4, 2018, now Pat. No. 11,433,227, which is a continuation of application No. 14/208,487, filed on Mar. 13, 2014, now Pat. No. 9,974,941.

(60) Provisional application No. 61/779,122, filed on Mar. 13, 2013.

(51) Int. Cl.
  *A61M 39/16*     (2006.01)
  *A61M 39/10*     (2006.01)

(52) U.S. Cl.
  CPC ...... *A61M 39/165* (2013.01); *A61M 39/1011* (2013.01); *A61M 39/162* (2013.01); *A61M 2039/1033* (2013.01); *A61M 2039/1066* (2013.01)

(58) Field of Classification Search
  CPC .......... A61M 2005/3118; A61M 5/347; A61M 5/345; A61M 5/5086; A61M 2039/1066; A61M 2039/1033; A61M 39/165; A61M 39/1011
  See application file for complete search history.

(56) References Cited

U.S. PATENT DOCUMENTS

| | | | |
|---|---|---|---|
| 4,243,035 A | 1/1981 | Barrett | |
| 4,636,204 A | 1/1987 | Christopherson et al. | |
| 4,747,835 A * | 5/1988 | Sandhaus ............ | A61M 5/3213 604/263 |
| 4,838,875 A | 6/1989 | Somor | |
| 4,859,336 A | 8/1989 | Savas et al. | |
| 4,981,469 A * | 1/1991 | Whitehouse .......... | A61M 39/14 604/905 |
| 5,135,509 A | 8/1992 | Olliffe | |
| 5,154,285 A | 10/1992 | Hollister | |
| 5,190,534 A | 3/1993 | Kendell | |
| 5,232,455 A | 8/1993 | Hollister | |

(Continued)

FOREIGN PATENT DOCUMENTS

| | | |
|---|---|---|
| EP | 0 471 574 | 2/1992 |
| FR | 2 985 433 | 7/2013 |

(Continued)

OTHER PUBLICATIONS

Extended European Search Report, dated Apr. 7, 2017 cited in EP 14 77 4399, 7 pages.

*Primary Examiner* — James D Ponton
*Assistant Examiner* — Hong-Van N Trinh
(74) *Attorney, Agent, or Firm* — Merchant & Gould P.C.

(57)     ABSTRACT

A system relating to improved medical-connector contamination prevention. More particularly, this invention relates to a reduced-touch contamination system for small-bore fluid connectors, including male and female Luer-type connectors.

12 Claims, 80 Drawing Sheets

(56)                    References Cited

U.S. PATENT DOCUMENTS

| 5,286,067 A | | 2/1994 | Choksi | |
|---|---|---|---|---|
| 5,464,399 A | | 11/1995 | Boettger | |
| 5,492,147 A | | 2/1996 | Challender et al. | |
| 5,496,288 A | | 3/1996 | Sweeney | |
| 5,647,849 A | * | 7/1997 | Kalin | A61M 5/3243 |
| | | | | 604/111 |
| 5,827,244 A | | 10/1998 | Boettger | |
| 6,010,468 A | | 1/2000 | Carter | |
| 6,010,486 A | * | 1/2000 | Carter | A61M 5/3234 |
| | | | | 604/110 |
| 6,569,118 B2 | | 5/2003 | Johnson et al. | |
| D617,454 S | | 6/2010 | Shaw | |
| 8,002,757 B1 | | 8/2011 | Schultz | |
| 9,974,941 B2 | | 5/2018 | Schultz | |
| 11,433,227 B2 | * | 9/2022 | Schultz | A61M 39/162 |
| 2003/0109853 A1 | | 6/2003 | Harding | |
| 2003/0201639 A1 | | 10/2003 | Korkor | |
| 2004/0039341 A1 | | 2/2004 | Ranalletta | |
| 2005/0251096 A1 | | 11/2005 | Armstrong et al. | |
| 2008/0132851 A1 | * | 6/2008 | Shaw | A61M 5/347 |
| | | | | 604/199 |
| 2008/0172039 A1 | | 7/2008 | Raines | |
| 2009/0182309 A1 | | 7/2009 | Muffly | |
| 2009/0194453 A1 | | 8/2009 | Thorne, Jr. et al. | |
| 2010/0286604 A1 | | 11/2010 | Shaw | |
| 2010/0331822 A1 | | 12/2010 | Willemstyn | |
| 2012/0157914 A1 | | 6/2012 | Stroup | |

FOREIGN PATENT DOCUMENTS

| GB | 2 379 253 | 3/2003 |
|---|---|---|
| WO | WO 99/37356 | 7/1999 |

* cited by examiner

COLLAR-ATTACHABLE
EMBODIMENTS

LUER-ENGAGED
EMBODIMENTS

REMOVABLE-SHEILD
EMBODIMENTS

Concave and Convex Inlet

Universal Single Part
Shield Male-Luer
Adapter with
Female Luer
Connector

Convex Inlet

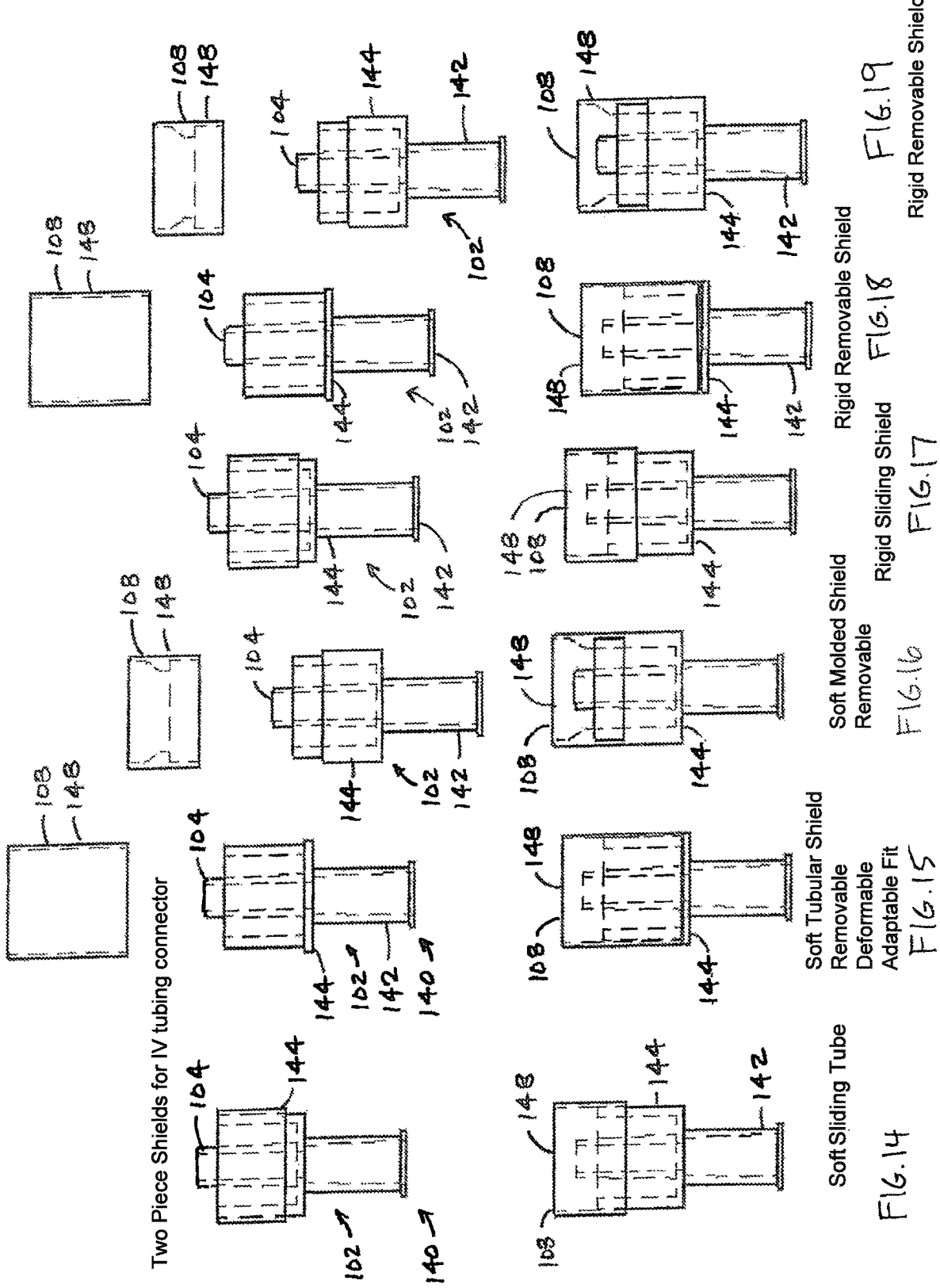

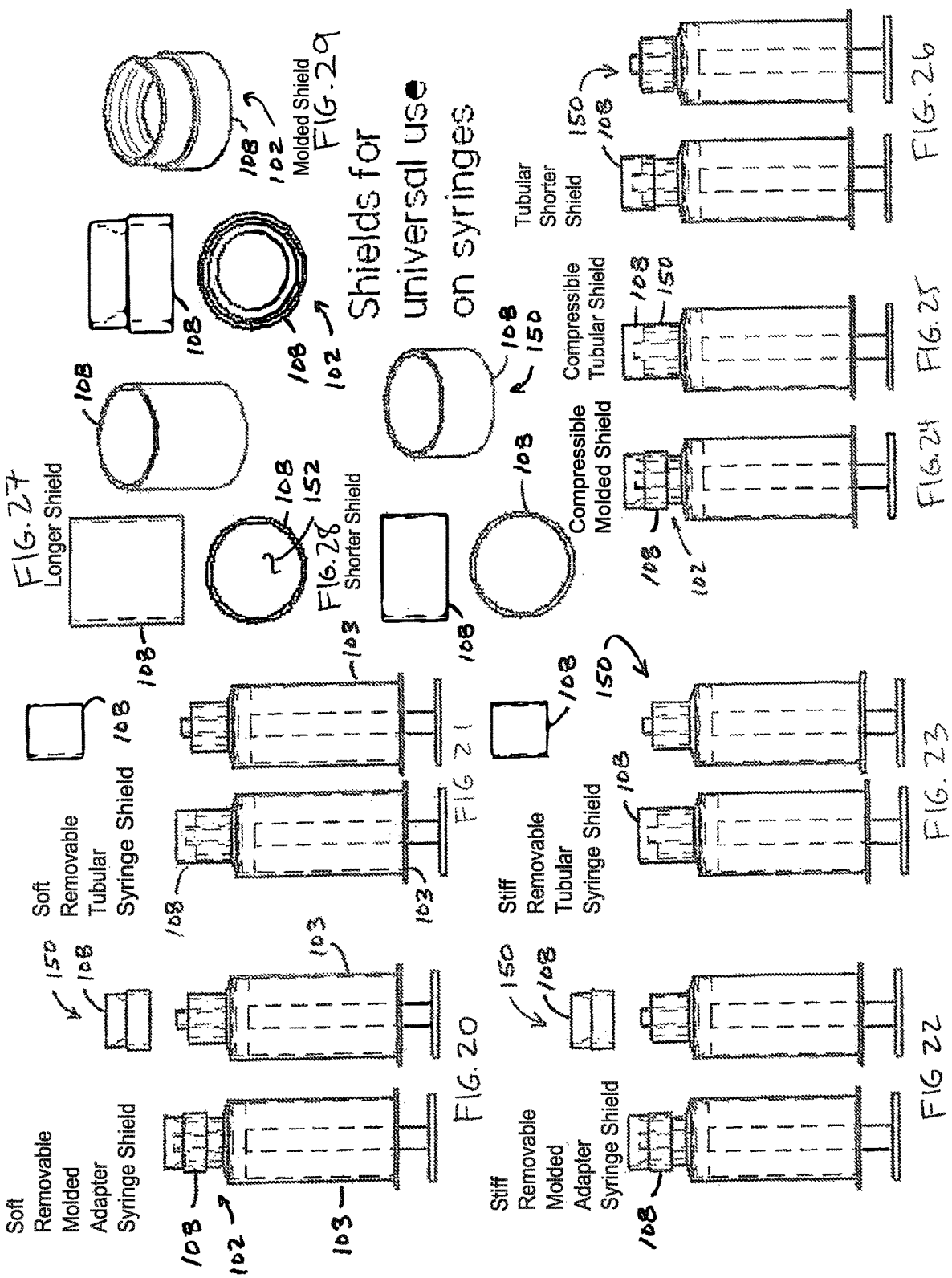

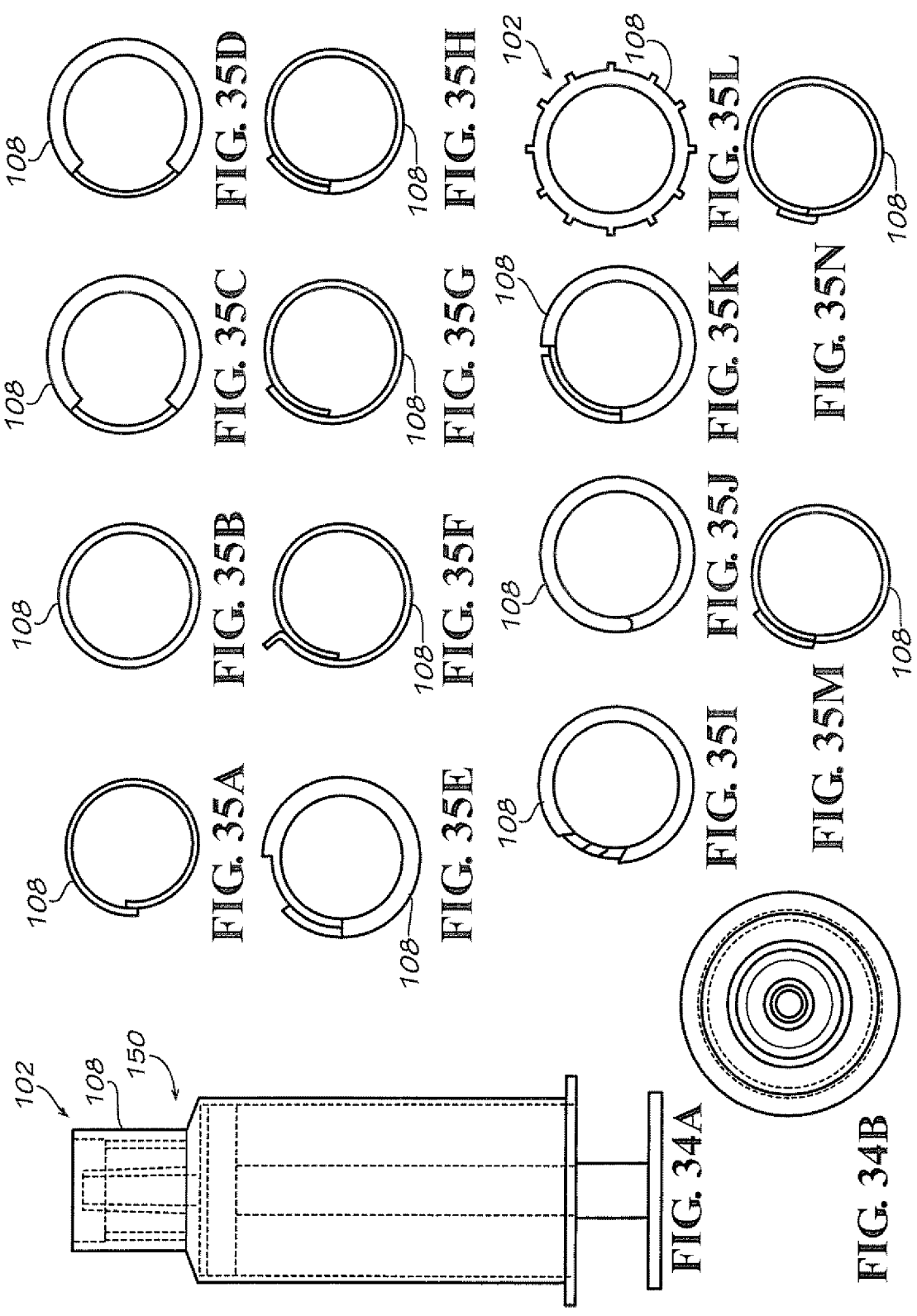

EXTRUDED UNIT

SHIELD COMPRISES AN ABSORBENT MATERIAL

RESILIENT COMPOSITION

EXTRUDED UNIT

SHIELD IS DEFORMABLE AWAY FROM DEVICE COLLAR AS REQUIRED

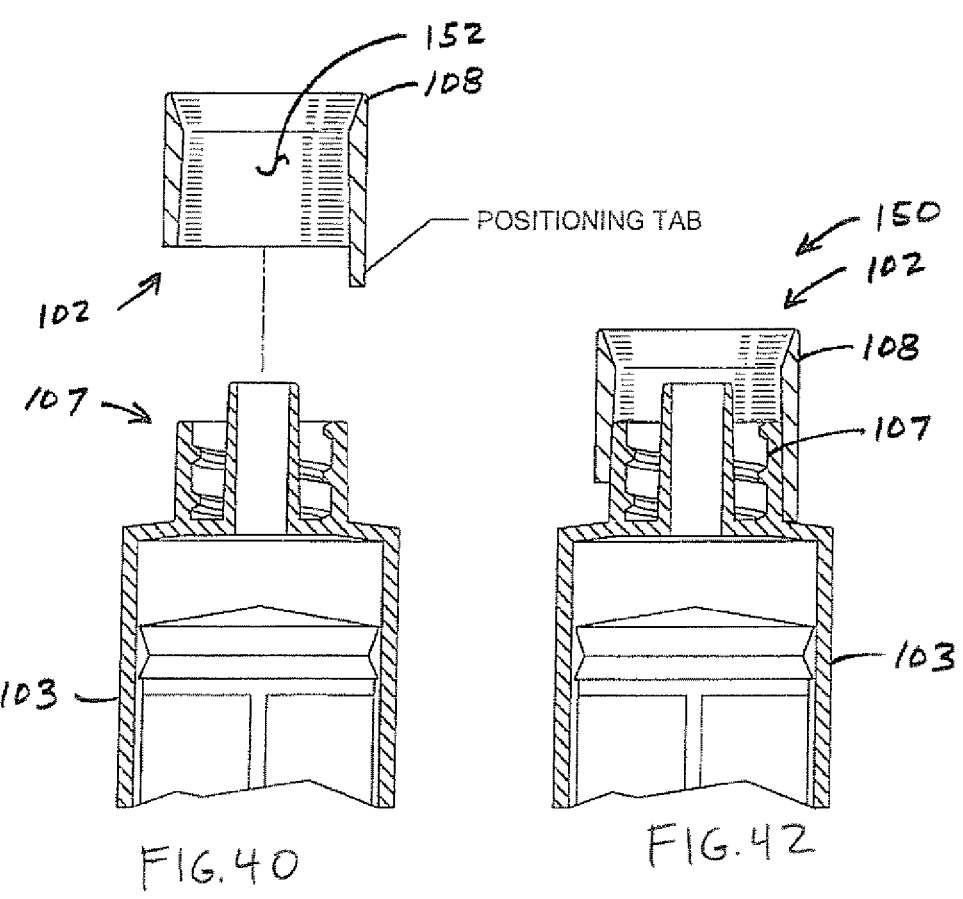
FIG.40
FIG.42
SHIELD IS MOVABLE ALONG DEVICE COLLAR
MOVABLE SHIELD INCLUDES POSITIONING TAB
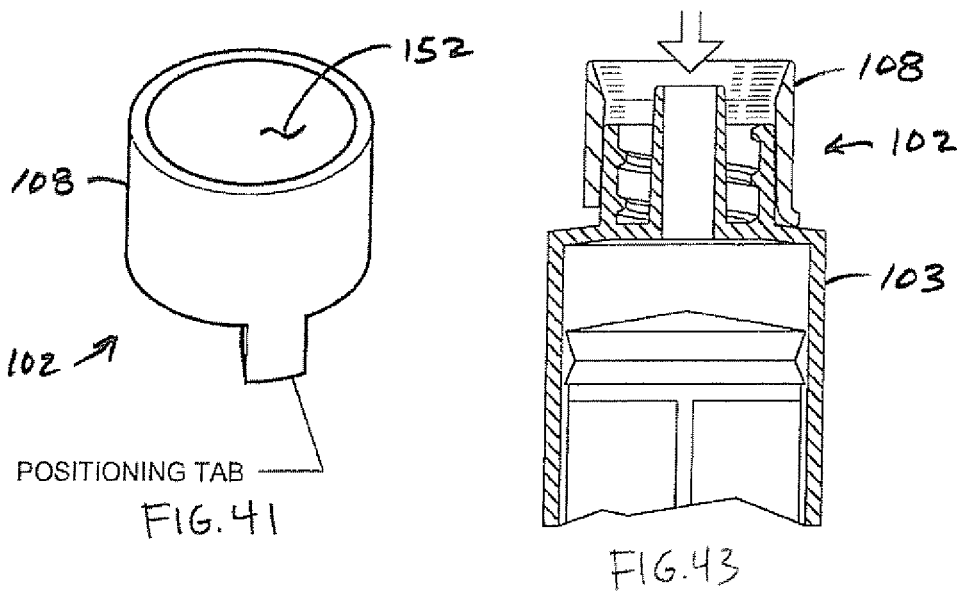
FIG.41
FIG.43

SHIELD IS ADHERED FILM

"SQUEEZE POINTS"
OVAL EMBODIMENT

MOLDED UNIT

120

102 →

110

108

104

UNITARY BODY
INTEGRAL SHEILD

SECTION B-B

SECTION B-B

120

102

UNITARY BODY
INTEGRAL SHEILD

SECTION B-B

SECTION A-A

102

120

UNITARY BODY
INTEGRAL SHEILD

SECTION A-A

A

A

SECTION A-A

120

UNITARY BODY
INTEGRAL SHEILD

102

136

108

SECTION A-A

UNITARY BODY
INTEGRAL SHEILD 102
120
136

SECTION A-A

SECTION A-A

UNITARY BODY
INTEGRAL SHEILD

SECTION E-E

SECTION E-E

UNITARY BODY
INTEGRAL SHEILD

SECTION A-A

SECTION A-A

102

UNITARY BODY
INTEGRAL SHEILD

SECTION B-B

102

120

SECTION B-B

UNITARY BODY
INTEGRAL SHEILD

SECTION A-A

SECTION A-A

SECTION A-A

120

102

UNITARY BODY
INTEGRAL SHEILD

SECTION A-A

SECTION D-D

120

102

UNITARY BODY
INTEGRAL SHEILD

SECTION D-D

SECTION B-B

120 →

UNITARY BODY
INTEGRAL SHEILD

102

SECTION B-B

102

B

SECTION B-B

B 120
136
104
UNITARY BODY
INTEGRAL SHEILD

102

SECTION B-B

102

UNITARY BODY
INTEGRAL SHEILD

SECTION A-A

102

120

136

104

SECTION A-A

ROTATABLE COLLAR

TWO-PART UNIT

ROTATABLE COLLAR
TWO-PART UNIT

TWO-PART UNIT

ROTATABLE COLLAR

TWO-PART UNIT

SECTION B-B

SECTION A-A

SECTION A-A

ROTATABLE
TWO-PART UNIT

SHEILD-RETRACTABLE EMBODIMENTS

SHIELD IS MOVABLE RELATIVE TO TIP/COLLAR
MOVABLE SHIELD INCLUDES BIASING SPRING

SHEILD-RETRACTABLE EMBODIMENTS

SHIELD IS MOVABLE RELATIVE TO TIP/COLLAR
MOVABLE SHIELD INCLUDES BIASING SPRING

SHIELD IS HINGED

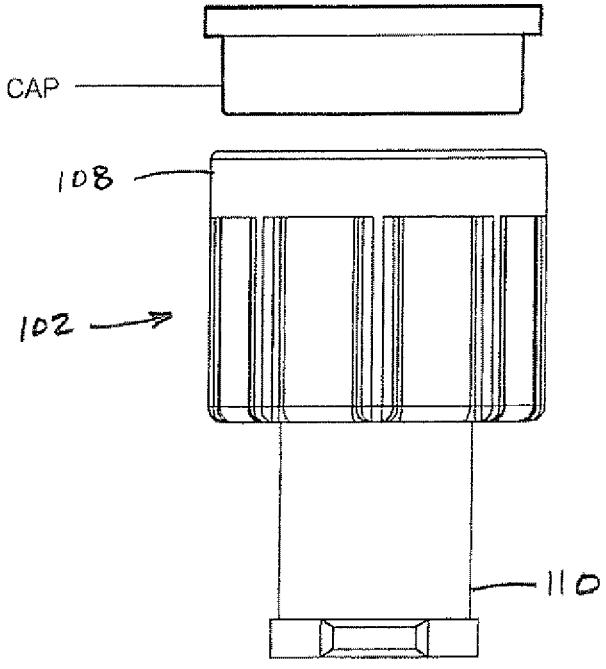
FIG. 74
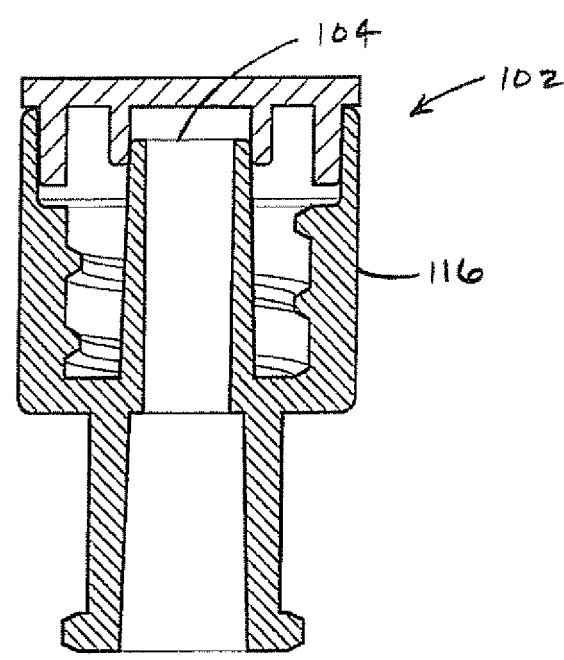

SECTION A-A
SCALE 5:1

PRESS FIT OR ADHESIVE BONDED 4.10 [0.161 in]

11.11 [0.438 in]

9.53 [0.375 in]

2.00 [0.079 in]

SECTION A-A
SCALE 5:1

PRESS FIT OR ADHESIVE BONDED 10.60 [0.417 in]

9.53 [0.375 in]

4.10 [0.161 in]

11.11 [0.438 in]

2.00 [0.079 in]

SECTION A-A
SCALE 5:1

SECTION B-B
SCALE 5:1

SECTION A-A
SCALE 5:1

120

1.00 [0.039 in]

1.10 [0.043 in]

2.10 [0.083 in]

X2

MINUS 1
DEGREE SIDE 10.00 [0.394 in]

83.0° [83.000°]

Ø11.00 [0.433 in]

3.10 [0.122 in]

A

A

102

ISO VIEW

SECTION A-A
SCALE 5:1

1.50 [0.059 in]
R0.50 [0.020 in]
R1.10 [0.043 in]
8.00 [0.315 in]
MINUS 1 DEGREE
DRAFT PER SIDE
10.0 [0.393 in]
11.00 [0.433 in]
3.60 [0.142 in]
R0.25 [0.010 in]

102
120

2.50 [0.098 in]

SECTION B-B
SCALE 5:1

NOMINAL 3 DEGREE IV
SUPPORT ANGLE

R0.50 [0.020 in]

12.00 [0.472 in]

8.60 [0.339 in]

0.44 [0.017 in]

9.53 [0.375 in]

11.11 [0.438 in]

SECTION A-A
SCALE 5:1

2 DEGREE ANGLE TAPER PRESS FIT

102

A

A

DETAIL B
SCALE 10 : 1

45°

TACTILE GRIP FEATURE

MOLDED STRESS RISER
TEAR OFF NOTCH

SHIELD TEAR OFF RIB/NOTCH FEATURES

SECTION C-C
SCALE 5:1

TEAR OFF GRIP RIB

SECTION A-A
SCALE 5:1

102

RADIAL RIB FEATURE
FOR SHIELD TUBE

FULL CIRCUMFERENCE SHIELD

STANDARD ISO LUER THREADS

FEATURES BASED ON ISO
LUER STANDARDS

RIBBED (POST) OPENINGS
FOR VISUAL ALIGNMENT AND
SHIELDING 16.60 [0.654 in]

Ø11.00 [0.433 in]

0.50 [0.020 in]

7.50 [0.295 in]

2.10 [0.083 in]

SECTION A-A
SCALE 4:1

0.50 [0.020 in]

116

106

STANDARD ISO
LUER LOCK
FEATUERS

POST IS: SUB FLUSH,
FLUSH OR EXTENDING
PAST THE LUER ENTRY

SECTION A-A
SCALE 5:1

6 OR OTHER MULTIPLICITY
OF POST PROTRUSIONS

STANDARD ISO LUER THREADS

Ø11.00 [0.433 in]

104

16.60 [0.654 in]

POST PROTRUSION
FEATURES FOR
SHIELDING

102

180

CYLINDRICAL SHIELD 0.50[0.020 in]

11.00 [0.433 in]

9.50 [0.374 in]

3.4°[3.440°]

4.24 [0.187 in]

ISO FEMALE LUER FEATURE

SECTION A-A
SCALE 5:1

2.10[0.083 in]

106

104

180

180

102

ISO VIEW

SECTION C-C

RETRACTING SNAP FIT
RAMP FEATURE

ASSEMBLY SNAP FIT
FEATURE

30°

50°

SECTION A-A
SCALE 5:1

A

A

125

104

ISO FEMALE
LUER FEATURE

ISO LUER TIP
FEATURE

ISO LUER FEMALE FEATURE

SECTION A-A
SCALE 5 : 1

104

125

ASSEMBLY SNAP FIT FEATURE
(SLIDE ONLY)

SLIDE AND SNAP FIT FEATURE
TO ROTATE 360 DEGREES

ISO LUER TIP

SLIDING ALIGNMENT RIB FEATURES (3)

SECTION B-B
SCALE 5 : 1

125

104

MEDICAL CONNECTOR CONTAMINATION PREVENTION DEVICE

CROSS-REFERENCE TO RELATED APPLICATIONS

This application is a continuation of U.S. patent application Ser. No. 15/971,091, filed May 4, 2018, now U.S. Pat. No. 11,433,227, which is a continuation of U.S. patent application Ser. No. 14/208,487, filed Mar. 13, 2014, now U.S. Pat. No. 9,974,941, which claims the priority benefit of U.S. Provisional Patent Application Ser. No. 61/779,122, filed Mar. 13, 2013, both each of which are hereby incorporated herein by reference.

TECHNICAL FIELD

This invention relates to providing a system for improved medical-connector contamination prevention. More particularly, this invention relates to various embodiments of a reduced touch contamination system for small-bore fluid connectors, including male Luer lock connectors.

BACKGROUND

Touch contamination in medical-care environments has been identified as a frequent contributor to medical complications including vascular-access-associated infections and is now considered a leading compromiser of patient safety.

Hospital-acquired bloodstream infections are estimated to cause thousands of deaths a year and billions in lost revenues; many of these are related to indwelling vascular access devices, including intravenous (IV) catheters. Non-sterile contact of a sterile surface of a medical device with a non-sterile surface can contaminate a medical device. This can have deadly results when dealing with intravascular fluid connectors since contamination through an intravascular line can bypass the skin barriers and be directly transmitted into the bloodstream, and throughout the body, to key organs such as the brain or heart, and/or could lead to widespread sepsis, shock and death.

Care must be made when connecting intravenous devices as even minute contamination of critical connector surfaces could introduce bacteria directly into the fluid path entering the bloodstream. Contamination risks frequently are thought to occur at the site of insertion of an intravascular line; however, it is applicant's observation that a frequently overlooked factor in contamination is the subsequent connections and in particular the insertion of the male "Luer" tip into the compatible female "Luer" connector.

Luer connections have been identified as sources for infection. Tragically, little has been done to successfully deal with producing a better connector that helps to reduce infection and is acceptable to the medical marketplace for widespread use. A simple system to protect Luer connectors that assures universal connectivity with standard and non-standard female Luer-like connectors, while also providing widespread protection against contact contamination, does not currently exist.

Contact of a sterile surface of a medical device with a non-sterile surface is a common mode of hazardous contamination. This contamination can have deadly results when dealing with intravascular fluid connectors as contamination through an intravascular line bypasses the skin barriers and directly transmits the contamination into the bloodstream and throughout the body to key organs such as the brain or heart, and/or could lead to widespread sepsis, shock and death.

Luer connectors are ubiquitous throughout the healthcare industry and frequently are used to provide connections to intravascular access. Luer connectors refer to large bore and small bore Luer connectors, not just any device with a 6% Luer angle. In the present invention, "Luer connectors" preferably refers to small bore Luer connectors. Luer devices are standard for intravenous access. Intravenous catheters have a female lock Luer hub on a proximal end that receives another medical device with male Luer connector on the distal end. These male Luer connectors are frequently Luer lock connectors with internally threaded collars, which help secure the connection between the male and female Luer connectors.

Luer connectors originated in late 1800s when Wolfgang Luer invented a two piece syringe. The Luer connector that followed comprised a 6% taper. Luer locks were a later advance that assisted with securing with threaded connections. The earlier Luer and Luer-lock connectors were made of steel and glass and standards existed as early as the 1950s; only in the early 1990s was a standard developed for plastic components with the ANSI standard. Shortly thereafter, a more comprehensive ISO standard was developed that has become the guiding document for the medical industry.

This ISO standard (ISO 594-1:1986 and 594-2:1998) insures the universal compatibility of multiple devices; however, the international dimensional standards also provide an obstacle to modifying Luer devices to prevent contact contamination. Female Luer connector hubs are recognized as the receiving end for male Luer connectors. It would be inconvenient and at times extremely dangerous to have non-compatible connectors. For example, when wanting to give resuscitation drugs in an ambulance, if the paramedic's intravenous (IV) tubing did not match the IV catheter, this would be dangerous. Even if an adapter were available in a separate package, time lost could lead to blood spills and biohazard risks while locating and opening the separate packaging of the other connector, as well as the delay in resuscitation medication delivery and distraction and confusion of the critical event.

While there has been a move to specialize connectors to reduce misconnection issues, it is generally accepted that the Luer standard is likely to remain the primary standard for intravascular access. While new standards may be developed for intrathecal administration or enteral administration, the current Luer standards are likely to persist.

Upstream from IV catheters, intravenous extension connectors, access ports, and fluid administrations sets connect necessary accessory tubing with the same convention of having female Luer-like receiving ports. For IV administration sets, frequently the most proximal portion contains an IV spike that inserts into the fluid origination source of a bag of IV fluid.

Inline adapters are attached with an open ended female IV catheter hub that accepts a standard male Luer adapter. For example, there are many port access devices that are attached to IV catheter hubs for intermittent access. Port access devices can also be located more proximally up the chain of extension tubing. The IV catheter ports can provide an end adapter that allows the proximal IV tubing to be removed from a distal IV catheter.

Originally these port and port caps allowed for needle insertion and access for the intermittent or continuous administration of IV medications and fluids. These ports required cleaning with disinfectants such as an alcohol swab prior to the insertion of a needle through the pierceable endwall (to reduce the risks of directly inoculating microorganisms on the outer surface into the inner lumen). More recently, these IV catheter ports have been adapted for needleless connection directly to syringes, tubing etc. with male Luer connector tips. In some cases, the design of these needleless connectors has led to increased risk of intravascular contamination, which will be discussed below.

Care must be made when connecting with and accessing intravenous devices because even minute contamination of any of these surfaces could introduce bacteria directly into the fluid path entering the bloodstream. Contamination risks frequently are thought to occur at the site of insertion of an intravascular line. However, it is applicant's observation that a frequently overlooked factor in contamination is the subsequent connections and in particular the insertion of the male Luer tip into the female connector.

In general, contamination is at a high risk of occurring when a male Luer device is inserted into the female Luer to assemble a closed intravenous fluid delivery system and also when the closed tubing system is accessed; for example, when a port, such as female Luer or female Luer-like valve, accepts a needle or male Luer for administration of fluid (frequently, this is done with a syringe). Intravenous catheters may be in for only minutes in places like an outpatient clinic or they can be in for years in a situation such as subcutaneous indwelling port access devices. There may be dozens or thousands of access events per intravascular device; each connection and access step has the potential to be a deadly one.

One of the problems with the current international ISO standard for Luer connectors is that Luer slip connectors are left with their tip-mating surface exposed. The slip connector's surface goes directly into the intravascular lumen. Luer connectors with locking collars have some degree of proximal contact contamination protection; however, even Luer connectors with locking collars have a high risk of contact contamination due to the 2.1 millimeter (mm) protrusion of the male tip beyond the collar of dictated by the current ISO standard; this makes the tip prone to contamination by contact with non-sterile surfaces (this can happen in a number of ways).

For example, the tip of intravenous tubing may be contaminated while exposed and resting on a stretcher-sheet surface. The torque of the IV tubing may cause the connector tip to touch the non-sterile linen and become contaminated. The longer the tip extends beyond the collar, the more risk there is of contamination, since there is less of an angle needed to change from a non-contaminated state in a orientation parallel to a flat sheet surface, to an angled state where the tip contacts the sheet. In contrast, the shorter the distance that the tip extends beyond the Luer locking collar, the less likely that such as event would occur.

Another risk of contamination occurs while handling the connector as the connector might be pushed into a non-sterile surface. For example, the sterile connector tip might be pushed into a bulge in the stretcher sheet or another device. If the protrusion distance of the tip from the collar were less than zero, the tip will be recessed within the collar. A tip recessed in a collar would have less chance of contamination since the collar would shield contact between a non sterile surface and the sterile tip of the male Luer.

Yet another potential contaminated surface is a finger or a glove of the health care provider. These surfaces might inadvertently touch the connector tip causing contamination. Sometimes this will occur when handling the connector for assembly, capping or recapping. The more deeply recessed the tip within a shielded collar, the less likely such an event will occur since the intruding non-sterile surface would have to travel farther within the collar to make the contact to contaminate the tip. Contact with the tip is an important factor since the tip will go directly into the fluid path while the collar remains on the outside.

There are other situations during the assembly process that make the standard Luer connectors prone to contamination. The male Luer connectors have a small tip that must engage a small female receiving end; sometimes, this can be difficult to achieve in a moving, uncooperative patient. Also, if the healthcare worker's vision or depth perception is poor, they are more likely to miss their target. In some cases, the protruding male connector tip might miss the female connector altogether. For example, the tip of the connector might hit a finger stabilizing the female connector. It might hit the side surface of the female connector which may not have been sterilized prior to access. If the male connector is then immediately inserted into the female connector, without re-sterilization, contamination may occur. Even if attempts are made to clean the male connector tip surface with a disinfectant, such as an iodine containing solution or alcohol, the residual disinfectant may have harmful toxic effects, or the practitioner may not wait for necessary drying to occur and contaminants may be flushed directly into the bloodstream once the male connector is connected and an infusion begun.

Recent advances in the medical connector field have focused on needleless access to reduce the risk of needle-sticks during the administration and disposal of needles used with injection ports. Needle-sticks can transmit deadly incurable infections to healthcare workers including HIV and Hepatitis. Since female connectors are standard for the input end of intravenous lines, the needle-stick reduction innovations have focused on improving the female input end. This is presumably because the output end had been needles attached to Luer lock syringes and when the needles are removed what remains is the male end of a universal fitting standard male Luer lock adapter.

While these medical connector designs have improved the safety conditions for healthcare workers by reducing needle-stick risks, they have brought on new issues related to safety of the patient being treated. For example, some of the new needleless access systems comprise valved features that increase the risk of bloodstream contamination due to the irregular surface contours that are more difficult to clean than a smooth surface. Some connectors have larger, wider connector bodies to accommodate the inner valve contents. These valve bodies can be wider than a standard female Luer stem. These wide connector bodies can be bigger targets for potential contact contamination of standard male Luer tips at the time of assembly and access, since typically only the proximal female connector end port is swabbed clean at the time of access and not the entire connector body which is frequently stabilized by non-sterile hands or gloves or has been in contact with the nonsterile skin surface of the patient. These wide bodied connectors reduce the margin for error since the male Luer tip might miss the female access port and instead of moving freely into the air, it will be more likely to hit the wide valve surface in close proximity that is contaminated.

Also, some of these needleless valve female connectors may accept male Luer connectors but do not have the standard female Luer dimensions. Some have a shortened distance from the female inlet end to the connector base. The outer surface of the wide bodied connector is closer to the female access end; therefore accelerating the tip touch contamination risks by reducing the margin for error when making connections at the female valve inlet.

Furthermore, another patient safety issue is that some of the newer needleless valve systems have new issues related to bounce contamination. These systems may have a flat or relatively flat receiving surface compared to the standard inner conical receiving surface of a standard female Luer lock. Downward pressure is required to activate these new needleless valves. Problems occur because the tip of a standard male Luer locking connector may touch the female connector end receiving surface before stabilization and engagement of the locking collar. A number of problems may result. The tip of the male connector may slide from a sterilized top surface to a non-sterile side surface. Even if the target is correctly contacted initially, the resilience of the valve may cause a "bounceback" effect pushing the male tip off the surface and then bouncing onto another non-sterile surface. The valve must be depressed the standard protrusion distance of the male Luer tip past the collar of 2.1 mm, before the standard Luer locking collar assists with stabilization.

SUMMARY

In accordance with a preferred embodiment hereof, this invention provides a unitary medical device, relating to assisting shielding of male Luer-type connectors from contamination when being connected to compatible female connectors, comprising: a male Luer-type connector comprising a male distal tip extending along a longitudinal axis and to be protected from contamination when being connected to a compatible female connector; wherein such male Luer-type connector comprises a second female Luer-type connector in fluid communication with such at least one male Luer-type connector; wherein such second female Luer-type connector is configured to be removably engagable with compatible male Luer-type connectors; and a shield configured to assist shielding such male distal tip to reduce contamination potential when such male distal tip is being connected to the compatible female connector; wherein such unitary medical device assists shielding of male Luer-type connectors from contamination when being connected to compatible female connectors.

Moreover, it provides such an unitary medical device wherein: such at least one shield comprises a distal terminating periphery defining a distal plane oriented at an angle substantially perpendicular to the longitudinal axis; such distal terminating periphery of such at least one shield is configured to substantially surround the longitudinal axis; and such male distal tip does not pass through the distal plane. Additionally, it provides such a unitary medical device wherein such at least one male Luer-type connector comprises at least one ISO standard male Luer-lock-type connector. Also, it provides such a unitary medical device wherein such shield is transparent. In addition, it provides such a unitary medical device wherein such shield is threaded.

In accordance with another preferred embodiment hereof, this invention provides a medical device system, relating to assisting shielding of male Luer-type connector distal tips from contamination when being connected to compatible female connectors, comprising: a male Luer-lock-type connector having a locking collar and a male distal tip extending along a longitudinal axis and to be protected from contamination when being connected to a compatible female connector; wherein such locking collar comprises a locking portion and a shield portion, such shield portion extending beyond such male distal tip and being configured to shield such male distal tip to reduce contamination potential when such male distal tip is being connected to the compatible female connector; wherein such shield portion comprises a distal terminating portion comprising a continuous periphery; wherein such shield portion does not obstruct connection when such male distal tip is being connected to the female Luer-type connector; wherein such shield portion is positionally fixed relative to such locking collar; and wherein such medical device system assists shielding of male Luer-type connector distal tips from contamination when being connected to compatible female connectors.

Furthermore, it provides such a medical device system wherein such at least one male Luer-type connector comprises at least one ISO standard male Luer-lock-type connector. Further, it provides such a medical device system wherein such shield portion is transparent. Even further, it provides such a medical device system further comprising: at least one medical-fluid delivery device; wherein such at least one medical-fluid delivery device comprises such at least one male Luer-type connector. The medical device system wherein at least one medical-fluid delivery device includes at least one selected from the group consisting essentially of: syringes, I.V. lines, valves, adapters, etc.

In accordance with another preferred embodiment hereof, this invention provides a medical device system, relating to assisting shielding of male Luer-type connector distal tips from contamination when being connected to compatible female connectors, comprising: a male Luer-lock-type connector having a locking collar and a male distal tip extending along a longitudinal axis and to be protected from contamination when being connected to a compatible female connector; wherein such male Luer-lock-type connector comprises at least one other fluid-conducting connector in fluid communication with such at least one male Luer-type connector; and wherein such locking collar comprises a locking portion and a shield portion, such shield portion being configured to shield such male distal tip to reduce contamination potential when such male distal tip is being connected to the compatible female connector; wherein such locking collar is rotatable; wherein such unitary medical device assists shielding of male Luer-type connectors from contamination when being connected to compatible female connectors.

Moreover, it provides such a unitary medical device wherein such male Luer-lock-type connector comprises at least one ISO standard male Luer-lock-type connector. Additionally, it provides such a medical device system wherein such at least one other fluid-conducting connector comprises fluid-conducting tubing. Also, it provides such a medical device system further comprising at least one female Luer-type connector structured and arranged to be in fluid communication with such male Luer-lock-type connector. In addition, it provides such a medical device system wherein such shield portion comprises threads matching ISO standard male Luer-lock-type connector. And, it provides such a medical device system wherein such shield portion comprises: at least one tip-protecting position configured to shield such male distal tip to reduce contamination potential; and at least one tip-exposed position configured provide exposed access to such male distal tip to provide unobstructed access to such male distal tip when being connected to a compatible female connector; wherein at least one of such at least one tip-exposed position and such at least one tip-exposed position limits rotation of such locking collar.

In accordance with another preferred embodiment hereof, this invention provides a medical device system, relating to assisting shielding of female Luer-type connectors from contamination when being connected to compatible male connectors, comprising: at least one female Luer-type connector comprising a female distal tip extending along a longitudinal axis and to be protected from contamination when being connected to a compatible male connector; at least one shield configured to shield such female distal tip to reduce contamination potential when such female distal tip is being connected to the compatible male connector; wherein such at least one shield does not obstruct connection when such female distal tip is being connected to the compatible male connector; wherein such medical device system assists shielding of the female Luer-type connectors from contamination when connected to such at least one male Luer-type connector and assists shielding such male distal tip from contamination when such male distal tip is being connected to the compatible female connector. Further, it provides such a medical device system wherein such at least one female Luer-type connector further comprises at least one male Luer-lock-type connector having a locking collar and a male distal tip.

In accordance with another preferred embodiment hereof, this invention provides a medical device system, relating to assisting shielding of at least one male Luer-lock-type connector having a locking collar and a male distal tip extending along a longitudinal axis and to be protected from contamination when being connected to a compatible female connector, such medical device system comprising: a male Luer-lock-type connector having a locking collar and a male distal tip, such locking collar having an outer cylindrical wall portion; a shield configured to shield such male distal tip to reduce contamination potential when such male distal tip is being connected to the compatible female connector; wherein such shield comprises a continuous cylindrical member having an inner bore configured to engage such outer cylindrical wall portion of such locking collar wherein such continuous cylindrical member, when engaged about such locking collar, is configured to extend distally beyond such locking collar and such male distal tip; wherein such shield, when engaged on the locking collar, does not obstruct connection when such male distal tip is being connected the compatible female connector; wherein such medical device system, when engaged about such locking collar, assists shielding such male distal tip from contamination when such male distal tip is being connected to the compatible female connector.

Even further, it provides such a medical device system wherein such shield is removable from such medical device system. Moreover, it provides such a medical device system wherein such shield is flexible. Additionally, it provides such a medical device system wherein such shield is transparent. Also, it provides such a medical device system wherein such shield is rotatable.

In addition, it provides such a medical device system wherein such shield is retractable. And, it provides such a medical device system wherein such shield is transferable from such medical device system. Further, it provides such a medical device system wherein such shield means is transferable to such medical device system. Even further, it provides such a medical device system wherein such shield is elliptical. Moreover, it provides such a medical device system wherein such shield is sufficiently elastic to be stably frictionally held in place on such outer cylindrical wall portion.

Additionally, it provides such a medical device according to many of the above arrangements wherein the shield is elliptical. Also, it provides such a medical device according to many of the above arrangements wherein the male Luer-type connector matches ISO standards.

In addition, it provides such a medical device system wherein properties of such shield include any three selected from the group consisting of: flexible, transparent, rotatable, retractable, transferable, fluid absorbent. And, it provides such a medical device system wherein properties of such shield include any four selected from the group consisting of: flexible, transparent, rotatable, retractable, transferable, fluid absorbent. Further, it provides such a medical device system wherein properties of such shield include any five selected from the group consisting of: flexible, transparent, rotatable, retractable, transferable, fluid absorbent.

Even further, it provides such a medical device system wherein such shield comprises at a longitudinal split. Moreover, it provides such a medical device system wherein such shield comprises a spiral. Additionally, it provides such a medical device system wherein such shield comprises at least one projecting grip.

In accordance with another preferred embodiment hereof, this invention provides a method, of reducing fluid-path contamination in patient treatment, comprising the steps of: providing a first bulk quantity of medical devices each including a male Luer-type connector having a male distal tip extending longitudinally and to be protected from contamination when being connected to a female Luer-type connector; providing a second bulk quantity of contamination shields each configured to be placeable upon a such medical device in a position to reduce contamination of a such male distal tip when being connected to a female Luer-type connector; placing each of such second bulk quantity upon each of such first bulk quantity to provide a third bulk quantity of combined elements; sterilizing/packaging each of such third bulk quantity to provide a fourth bulk quantity of sterile packages; and making such fourth bulk quantity of sterile packages available for use in patient treatment. Also, it provides such a medical device system wherein such at least one male Luer-type connector comprises at least one ISO standard male Luer-lock-type connector.

In accordance with another preferred embodiment hereof, this invention provides a medical device system, relating to assisting shielding of at least one male Luer-lock-type connector having a locking collar and a male distal tip extending along a longitudinal axis and to be protected from contamination when being connected to a compatible female connector, such medical device system comprising: an shield configured to shield such male distal tip to reduce contamination potential when such male distal tip is being connected to the compatible female connector; wherein such shield comprises a cylindrical member having an inner bore configured to engage an outer cylindrical wall portion of the locking collar wherein such cylindrical member, when engaged about the locking collar, is configured to extend distally beyond the locking collar and the male distal tip; wherein the such cylindrical member comprises at least one liquid-absorbent material; wherein such shield, when engaged on the locking collar, does not obstruct connection when the male distal tip is being connected the compatible female connector; wherein such medical device system, when engaged about such locking collar, absorbs liquids while assisting shielding such male distal tip from contamination when such male distal tip is being connected to the compatible female connector.

In addition, it provides such a medical device system wherein such shield is removable from such medical device system. And, it provides such a medical device system wherein such shield is flexible. Further, it provides such a medical device system wherein such shield comprises at a longitudinal split. Even further, it provides such a medical device system wherein such shield comprises a spiral.

Even further, it provides such a medical device system wherein such shield comprises at least one projecting grip. Even further, it provides such a medical device system wherein such shield is elliptical. Moreover, it provides such a medical device system wherein such shield is transparent. Even further, it provides such a medical device system wherein such shield is retractable. In accordance with a preferred embodiment hereof, this invention provides each and every novel feature, element, combination, step and/or method disclosed or suggested by this patent application. A primary object and feature of the present invention is to provide such a system improving healthcare provider and patient safety by reducing touch contamination risks leading to complications, including vascular-access associated infection, by providing a guide to improve first pass connection success, providing shielded connection of the connector tip in the fluid path, and by providing a platform to reduce connector misconnects by visual and tactile means.

It is a further object and feature of the present invention to provide such a system comprising fluid connectors for intravascular use comprising a shield positioned to protect the tip of a male Luer connector and adapted for intravascular use and a standard male Luer lock connector.

An additional object and feature of the present invention is to provide such a system providing universal connectivity to female Luer-like connectors that accept male Luer-lock connectors.

It is a further object and feature of the present invention to provide such a system comprising fluid connectors for intravascular use comprising a shield positioned to protect the tip of a female Luer connector.

Another object and feature of the present invention is to provide such a system meeting current International Organization for Standardization (ISO) regulatory standards for these products.

Another object and feature of the present invention is to provide such a system that allows existing manufacturers to easily adopt the new technology with little or no tooling changes of existing Luer products, including male Luer locks.

It is a further object and feature of the present invention to provide such a system comprising shields having an opening size, at the protected tip, larger than the bore diameter of the locking Luer collar.

An additional object and feature of the present invention is to provide such a system providing method of bulk application.

A further primary object and feature of the present invention is to provide such a system that is efficient, inexpensive, and handy. Other objects and features of this invention will become apparent with reference to the following descriptions.

According to a further example embodiment, the present invention relates to an apparatus for improved assembly, disassembly and protection of a standard male Luer-lock including a circumferential collar with an inner surface that surrounds a proximal portion of a male Luer-lock conical connector. The inner surface is configured to receive a female Luer-lock profile. The apparatus includes a female connector with a proximal end and a distal end. The female connector proximal end is configured to removably secure within the standard male Luer-lock circumferential collar and around the standard male Luer-lock male conical connector. The apparatus includes a male conical connector including a proximal end and a distal end. The male conical connector proximal end is proximal to the female connector distal end. The apparatus also includes a substantially-circumferential shield including a proximal end and a distal end. The male conical connector distal end extends to a position within the substantially-circumferential shield between the proximal end and the distal end.

According to a further example embodiment of the invention, the present invention relates to a unitary construction apparatus for improved assembly, disassembly and protection of a standard male Luer-lock including a circumferential collar with an inner surface that surrounds a proximal portion of a male Luer-lock conical connector. The inner surface is configured to receive a female Luer-lock profile. The apparatus includes a shielded male Luer-type connecting means for releasably connecting to the female Luer-lock profile. The shielded male Luer-type connecting means includes a removable male shielding means for assisting shielding a distal tip portion of the male Luer-type connecting means to reduce contact contamination potential while such distal tip portion is exposed for connection to the compatible female connectors. The apparatus also includes a removable female Luer-type connecting means for releasably connecting to the male Luer-lock conical connector. The apparatus further includes a fluid conducting means for valveless fluid communication between the shielded male Luer-type connecting means and the female Luer-type connecting means. The male shielding means includes a tip surrounding means for at least partially circumferentially surrounding the distal tip portion.

According to a still further example embodiment, the present invention relates to a system to supply fluid through a standard female Luer-lock profile. The system includes a medical device with a standard male Luer-lock with a circumferential collar that surrounds a proximal portion of a male Luer-lock conical connector. The inner surface is configured to receive the female Luer-lock profile. The system also includes a removable shield to removably receive the standard male Luer-lock. The removable shield includes a proximal end and a distal end. The standard male Luer-lock conical connector distal end extends to a position within the removable shield between the proximal end and the distal end. The removable shield is configured to receive the standard female Luer-lock profile.

According to another example embodiment, the present invention relates to a method, relating to assisting shielding of unshielded male Luer-type connectors from contact contamination while the unshielded male Luer-type connectors are exposed for connection to compatible female connectors. The method includes providing a first bulk quantity of medical devices, each including a male Luer-type connector having a male distal tip extending longitudinally and to be protected from contamination while the male Luer-type connector is exposed for connection to compatible female connectors. The method also includes providing a second bulk quantity of contamination shields, each configured to be removably placeable upon a such medical device in a position to reduce contamination of a such male distal tip when being connected to the female Luer-type connectors. The method also includes removably placing each of the second bulk quantity upon each of such first bulk quantity to provide a third bulk quantity of combined elements. The method further includes packaging and sterilizing each of the third bulk quantity to provide a fourth bulk quantity of sterile packages. The method further includes making the fourth bulk quantity of sterile packages available for use in patient treatment. Each one of the medical connector devices consists essentially of at least one shielded male Luer-type connector with at least one male shield, and is configured to be releasably connectable to the compatible female connector and at least one female Luer-type connector configured to be releasably connectable to a compatible male Luer-type connector. The medical connector device includes at least one fluid path configured to provide valveless fluid communication between the shielded male Luer-type connector and the female Luer-type connector. The shielded male Luer-type connector includes a male conical fitting having a longitudinal axis and a distal tip portion. The distal tip portion includes a fluid outlet in fluid communication with said at least one fluid path. The at least one male shield is configured to assist shielding the distal tip portion to reduce contact contamination potential while the distal tip portion is exposed for connection to a compatible female connector. The at least one male shield, at least partially, surrounds said distal tip portion circumferentially.

BRIEF DESCRIPTION OF THE DRAWINGS

FIGS. 7-19 show side, top, cross-sectional and perspective views of male Luer-engaged reduced-touch contamination devices, according to a several contemplated example embodiments of the present invention.

FIGS. 20-49 show side, top, cross-sectional and perspective views of attachable collar-type reduced-touch contamination devices, according to a several contemplated example embodiments of the present invention.

FIGS. 50-74 show side, top, cross-sectional and perspective views of male Luer-engaged reduced-touch contamination devices, according to several further contemplated example embodiments of the present invention.

DETAILED DESCRIPTION OF EXAMPLE EMBODIMENTS

It is to be understood that this invention is not limited to the specific devices, methods, conditions, or parameters described and/or shown herein, and that the terminology used herein is for the purpose of describing particular embodiments by way of example only. Thus, the terminology is intended to be broadly construed and is not intended to be limiting of the claimed invention. For example, as used in the specification including the appended claims, the singular forms "a," "an," and "one" include the plural, the term "or" means "and/or," and reference to a particular numerical value includes at least that particular value, unless the context clearly dictates otherwise. In addition, any methods described herein are not intended to be limited to the sequence of steps described but can be carried out in other sequences, unless expressly stated otherwise herein.

Preferred devices of the present system provide Luer-like connectors designed to improve healthcare provider and patient safety by reducing touch contamination risks leading to medical complications, including infections associated direct vascular-access. Preferred devices of the present system are preferably configured to provide a guide to improve first-pass connection success, a shielded connection of the connector tip in the fluid path, and a platform to reduce connector misconnects by visual and tactile means.

Preferred embodiments of the present system are further configured to provide the above-described feature while maintaining full compatibility with current ISO regulatory standards for these products. Preferred embodiments of the present system allow existing manufacturers to adapt the present technology to existing Luer-based products, including male Luer locks.

Female Luer like connectors are defined herein to include standard small bore female Luer connectors, female small bore Luer access valves, and needleless injection sites that accept standard small bore male Luer lock connectors.

Figure 1A:
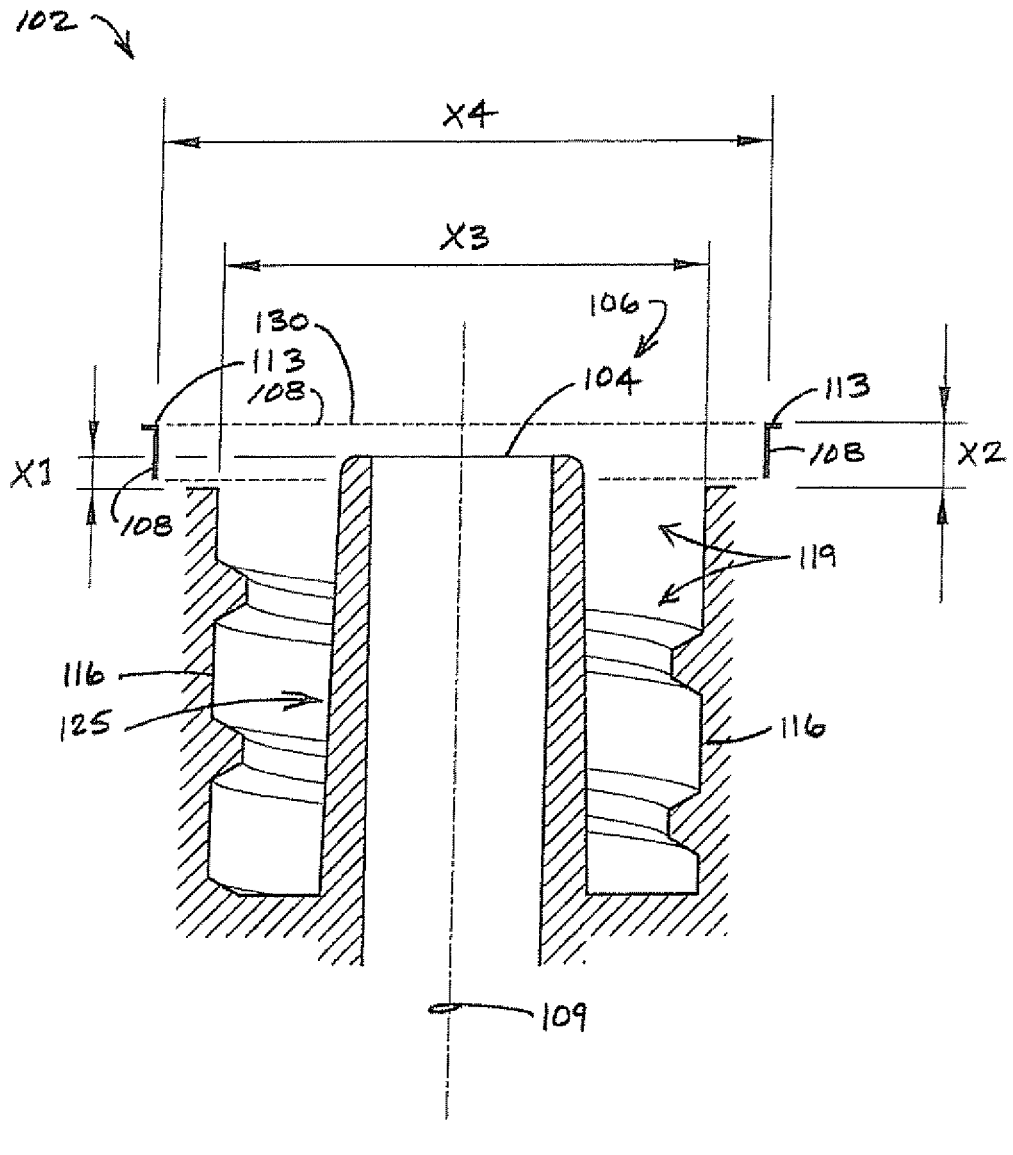
FIG. 1A shows a diagrammatic sectional view, illustrating an example geometric configuration of an example male Luer-type connector.

Referring to the accompanying illustrations, Applicant has developed a comprehensive range of preferred protective apparatus, identified generally herein as reduced-touch contamination devices. FIG. 1A shows a diagrammatic sectional view, illustrating a preferred geometric configuration of an example male Luer-type connector 100. As depicted, male Luer-type connectors 100 include a male Luer-lock-type connector 106 having a Luer locking collar 116 and a male 6% conical fitting 125 with a male distal tip 104 extending along longitudinal axis 109. The male Luer-type connector 106 preferably includes an ISO standard male Luer-lock-type connector matching ISO 594 standards; thus, the male distal tip 104 projects beyond the internally-threaded bore 119 a standard distance X1 of 2.1 millimeters (mm), as shown. As depicted, with a conventional ISO-standard Luer fitting, the male distal tip 104 is to be protected from contamination when in an exposed arrangement prior to being connected to a compatible female connector. As depicted, the male distal tip 104 includes distal portions of male 6% conical fitting 125 extending distance X1 beyond an internally-threaded bore 119 of Luer locking collar 116. The male Luer-type connector 100 is preferably constructed of a unitary single-bodied design.

As depicted, a shield 108 comprises a distal terminating periphery 113 defining a distal plane 130 oriented at an angle substantially perpendicular to longitudinal axis 109, as shown. The shield 108 is preferably circumferential and extends from the distal edge of the collar 116. Distal terminating periphery 113 of shield 108 is preferably arranged to substantially surround longitudinal axis 109 and exposed portions of male distal tip 104 extending beyond Luer locking collar 116 a distance X2 of between about 2.1 mm and about 3.6 mm (see also FIG. 5A), thus reducing fluid-path contamination potential. Preferably, male distal tip 104 does not pass through distal plane 130, as shown. This preference places male distal tip 104 at or below the level of shield 108, thereby reducing the potential of contact with non-sterile surfaces.

Preferably internally-threaded bore 119 comprises an inner bore diameter X3 matching matching ISO 594 standards. Shield 108 preferably comprises an opening dimension X4 at least equal to X3. More preferably, shield 108 comprises at an opening dimension X4 larger than X3, as shown. In example embodiments of the present system, the distal shield opening X3 is greater than about 8.1 mm, thus assisting targeting of the female connector to the male conical fitting and reducing interference issues during connection.

Figures 1B, 2:
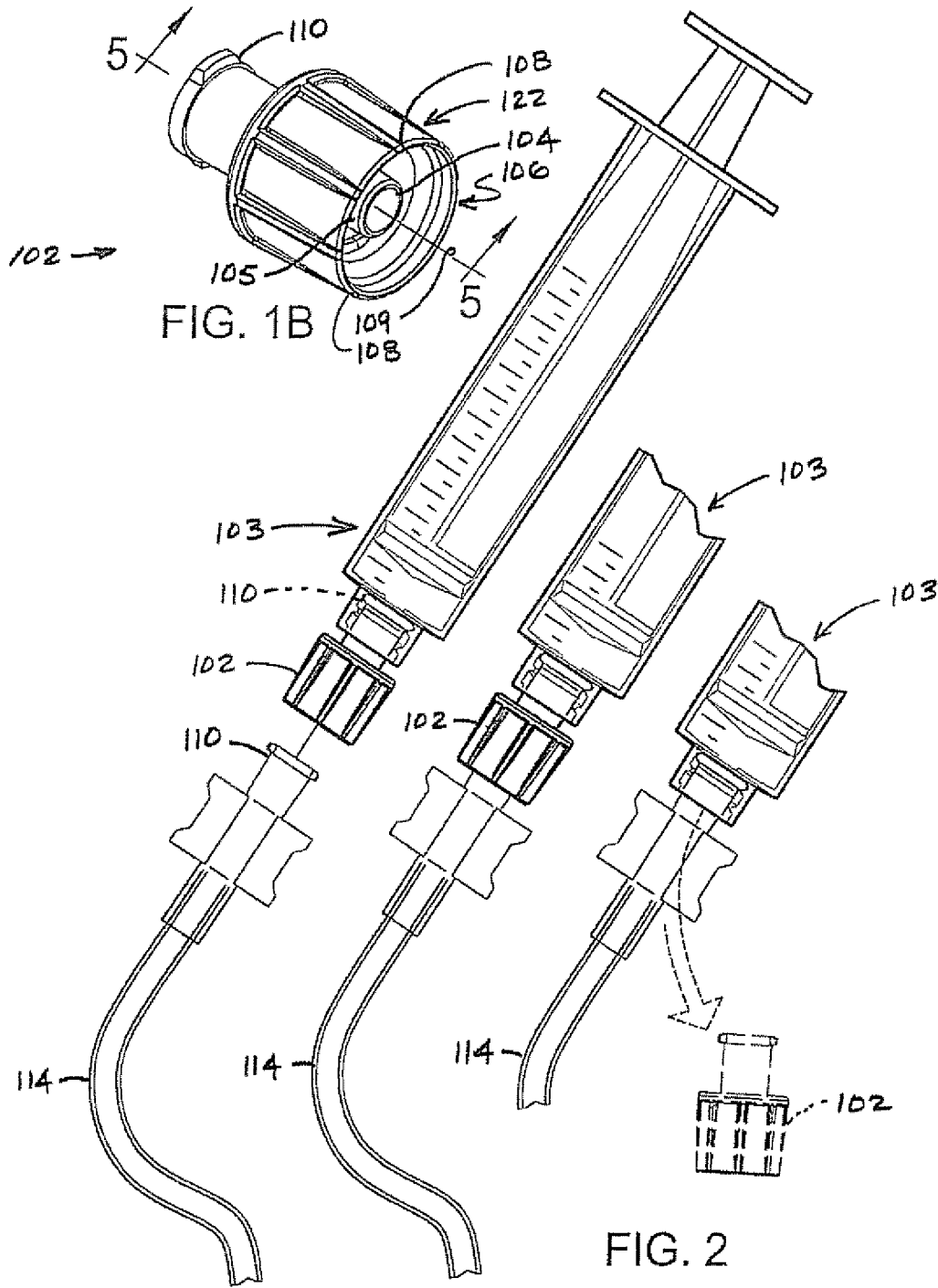
FIG. 1B shows a perspective view of a reduced-touch contamination device, according to a first example embodiment of the present invention.
FIG. 2 shows a group of side views, illustrating different example connection options of the reduced-touch contamination device shown in FIG. 1B to an existing medical product with the Luer-type connector shown in FIG. 1A.

FIG. 1B shows a perspective view, illustrating an example reduced-touch contamination device 102 of the preferred range, according to one preferred embodiment of the present invention. Preferred reduced-touch contamination devices 102 comprise at least one male Luer-type connector 106, as shown. Each reduced-touch contamination device 102 is preferably configured to protect at least the extending male distal tip 104 of a male (and sometimes female) Luer-type connector 106 (for example, IV Luer connector) to prevent touch contamination. Preferably, each reduced-touch contamination device 102 comprises at least one protective shield 108 configured to extend from the distal edge of the collar 116 and at least partially surround and shield an exposed male distal tip 104 of Luer-type connector 106 from unintended contact prior to connection with female Luer-type connector 210 (see FIG. 2). The depicted shield 108 is substantially cylindrical and of unitary construction with the collar 116.

The example arrangement of the shield 108 is preferably configured to protect male distal tip 104 by surrounding distal tip 104, as shown (see also FIG. 4 and FIG. 5A), thus reducing fluid-path contamination potential. The depicted embodiment of the shield 108 is preferably configured to protect the male distal tip 104 by extending distal portions of shield 108 beyond the male distal tip 104, as shown (see also FIG. 4 and FIG. 5A), thus reducing fluid-path contamination potential. Preferably, the shield 108 does not obstruct connection of a compatible Luer-type connector.

In reference to FIG. 1B, an example reduced-touch contamination device 102 is shown comprising a male Luer-type connector 106 having a male distal tip 104 extending along a longitudinal axis 109. Preferably, male Luer-type connector 106 is part of a unitary connector body 122 having a second connector, preferably a second female Luer-type connector 110 that is in fluid communication with male Luer-type connector 106. Female Luer-type connector 110 of the present embodiment is preferably configured to be removably engagable with compatible male locking Luer-type connectors having male 6% conical fittings 125. Male Luer-type connector 106 preferably comprises the shield 108 configured to assist shielding male distal tip 104 to reduce contamination potential when the distal tip is being connected to a compatible female connector.

FIG. 2 shows a group of side views, illustrating a set of preferred connection options utilizing the reduced-touch contamination device 102 of FIG. 1B, according to general preferred embodiments of the present invention. In the example implementation of FIG. 2, the depicted reduced-touch contamination device 102 is connected to an existing medical product 103, for example a medical syringe (empty or pre-filled).

Figures 7, 8:
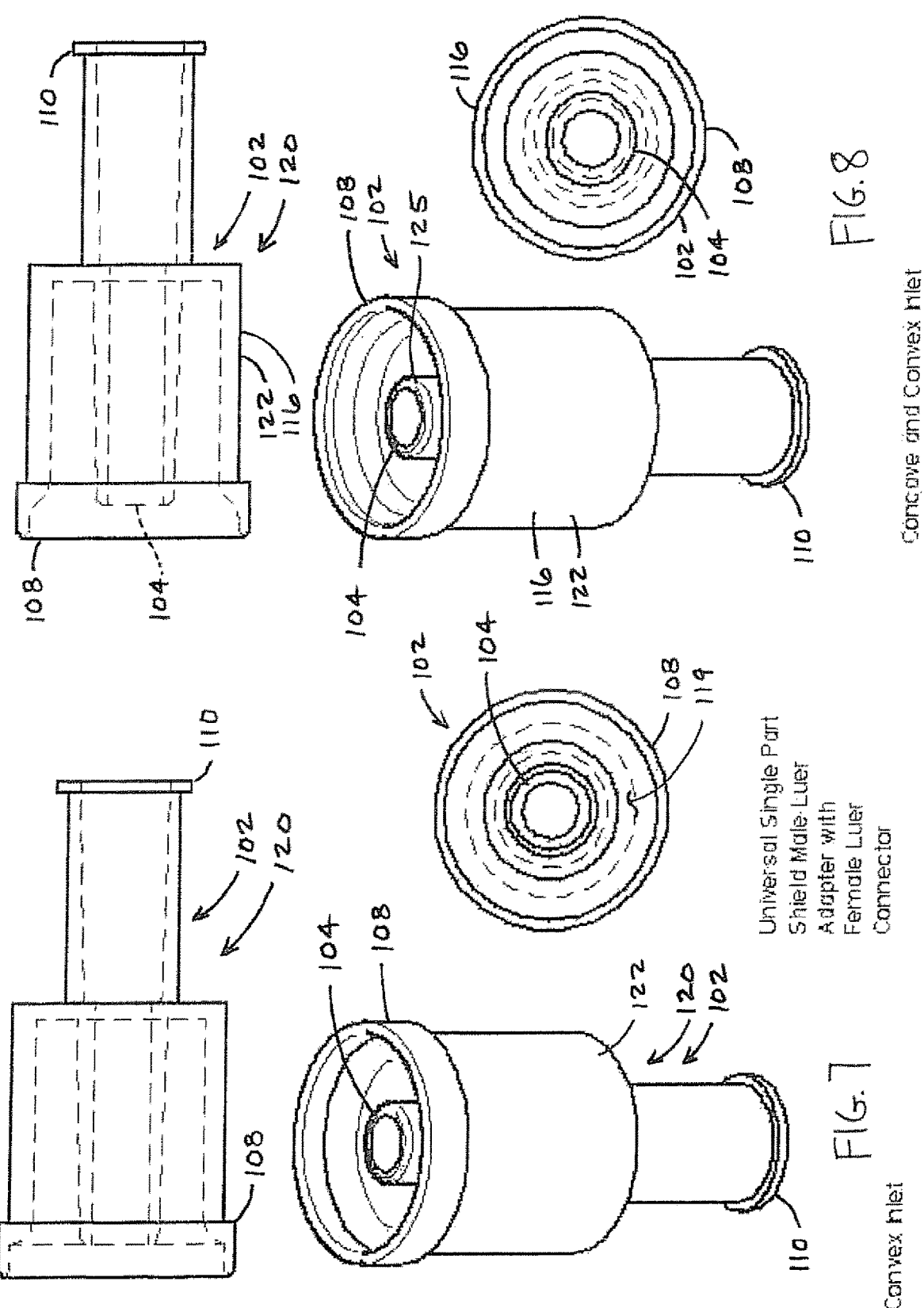
Figures 9, 10, 11, 12, 13:
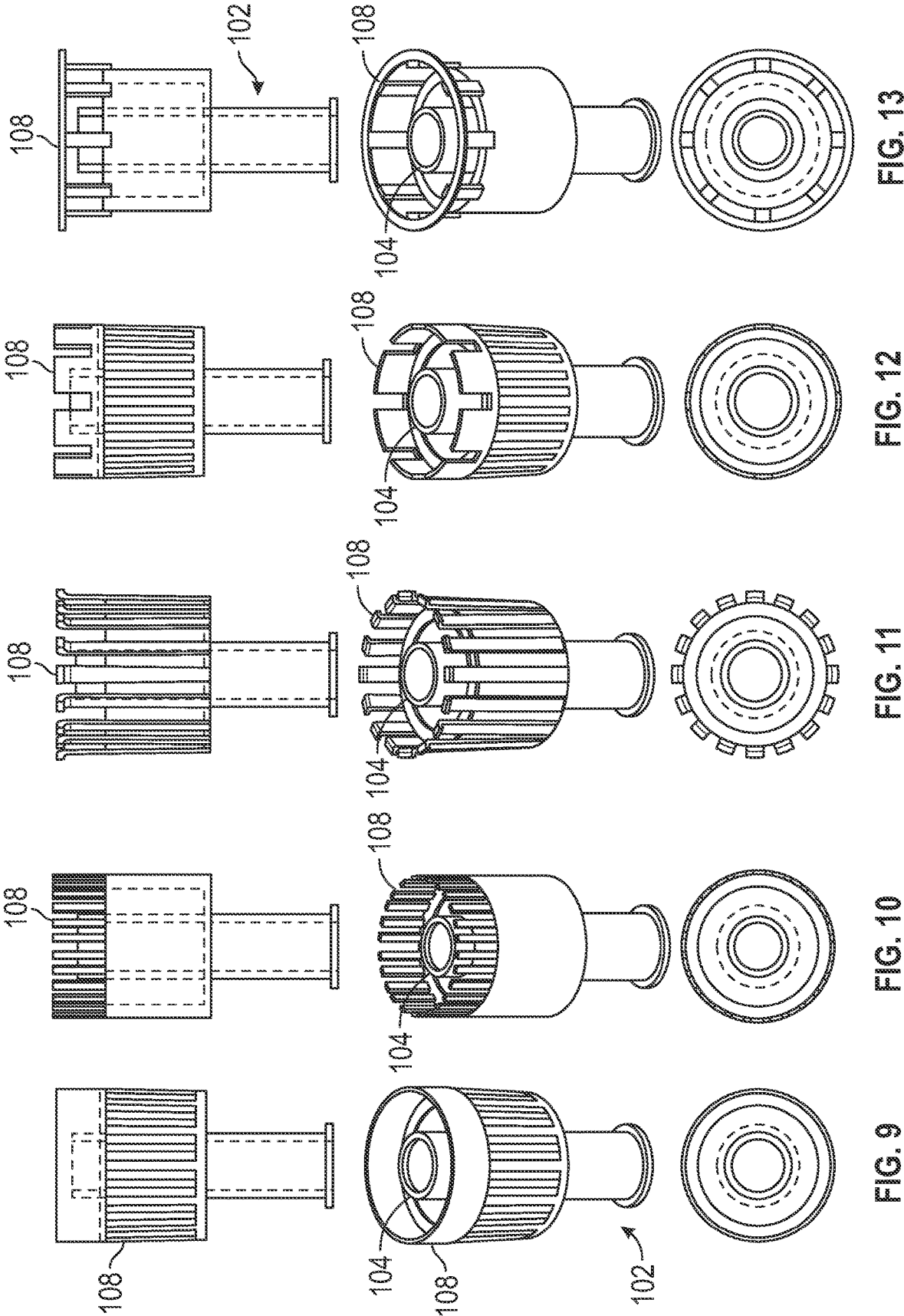
Figures 30, 31, 32A, 32B, 33:
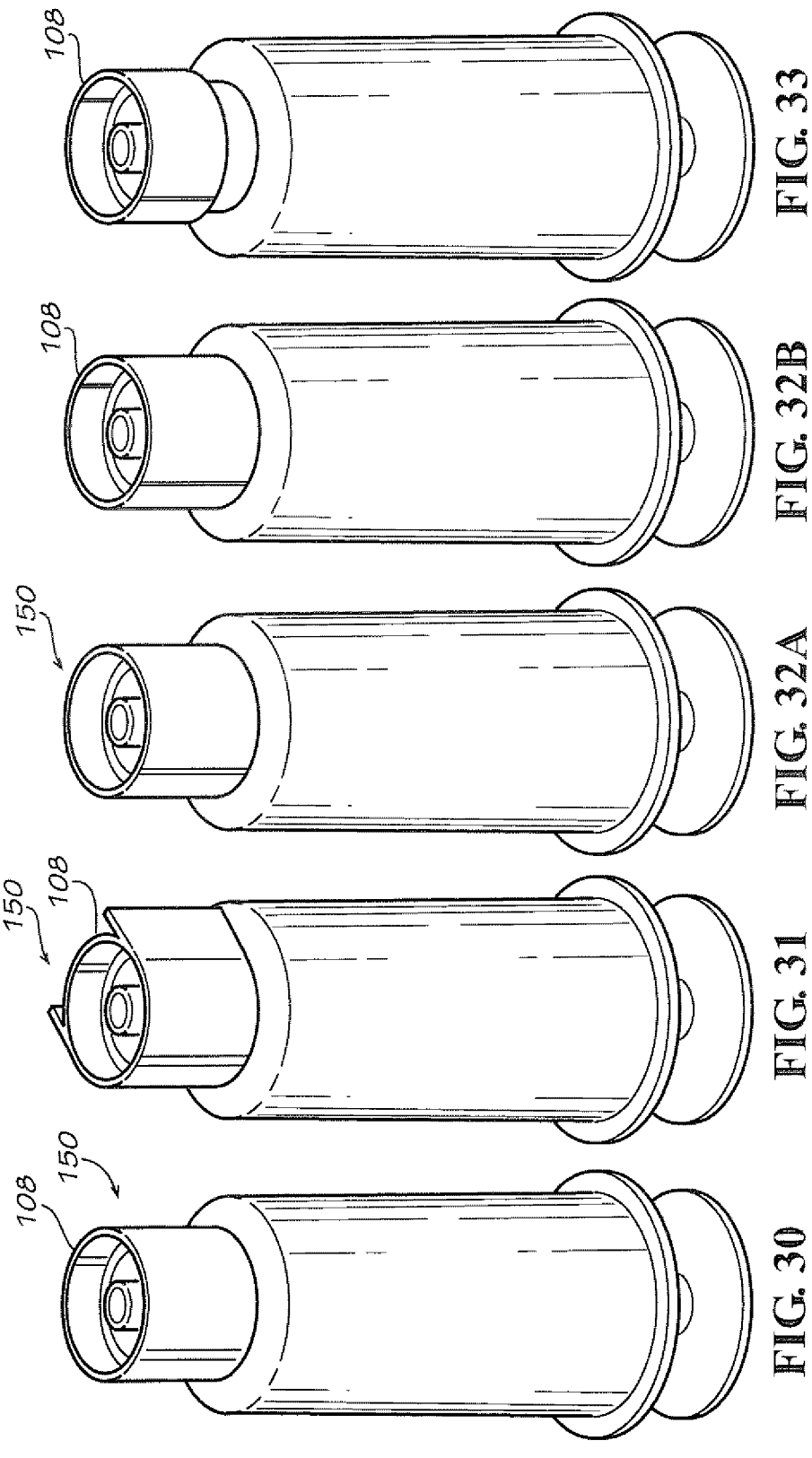
Figure 36:
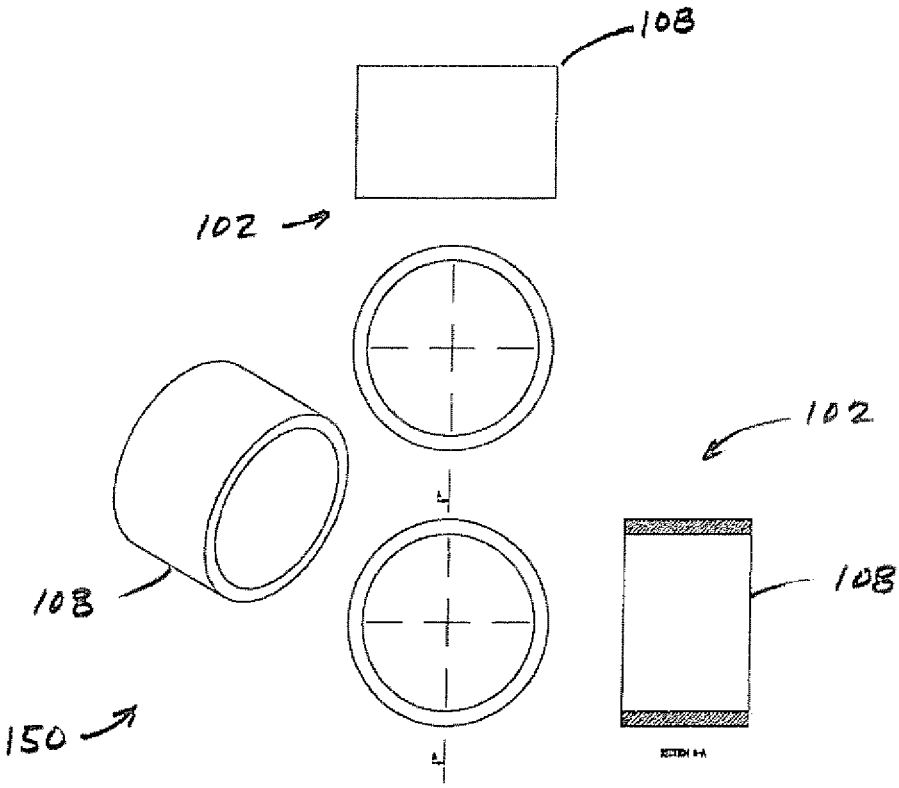
Figure 37:
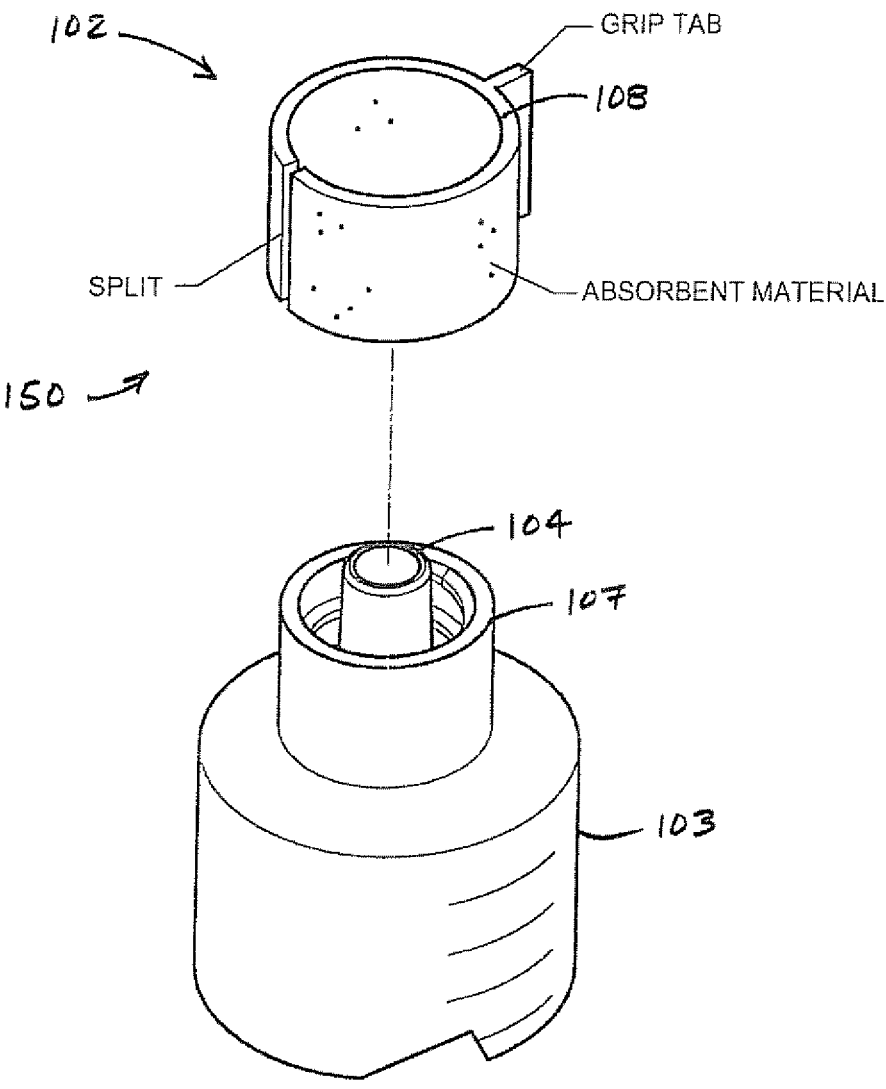
Figures 38, 39:
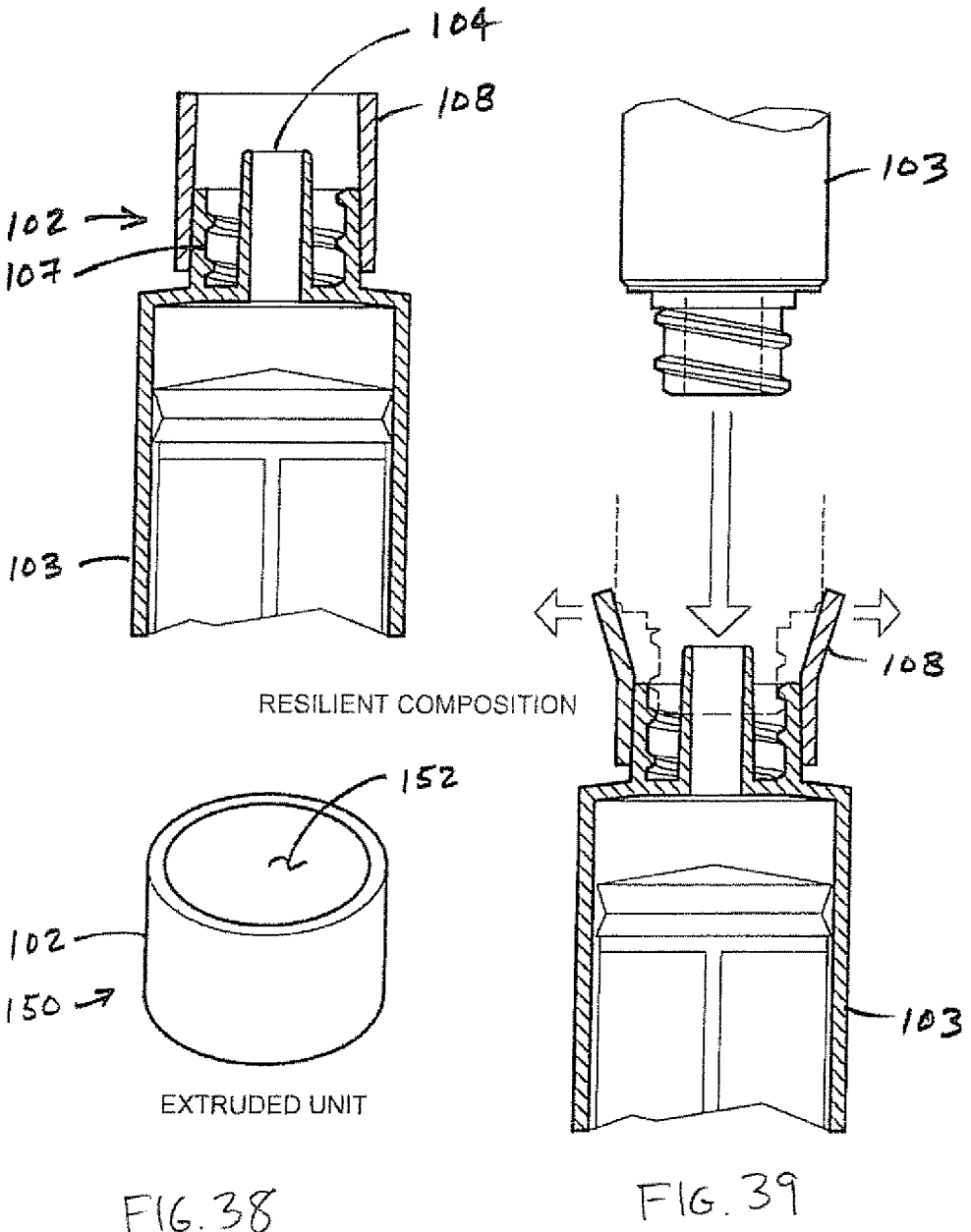
Figure 44:
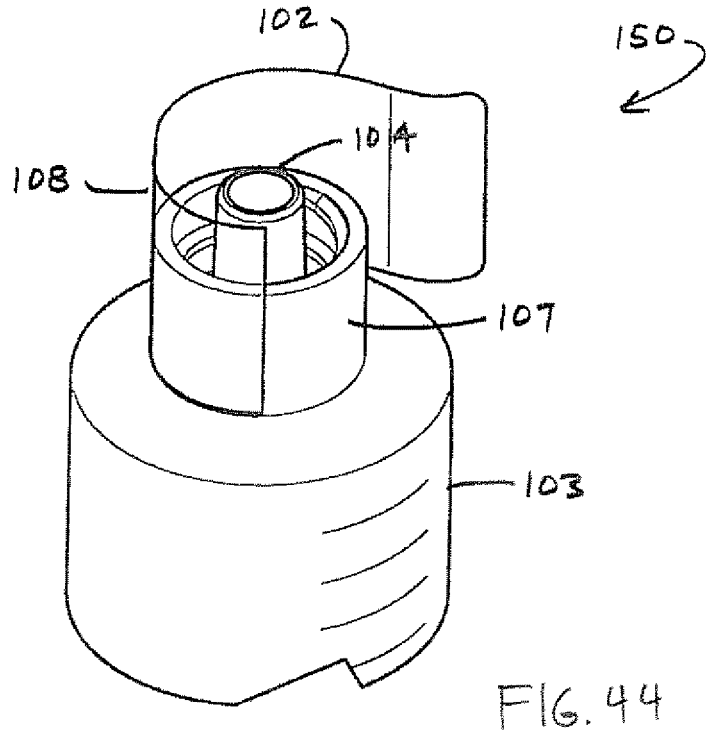
Figure 45:
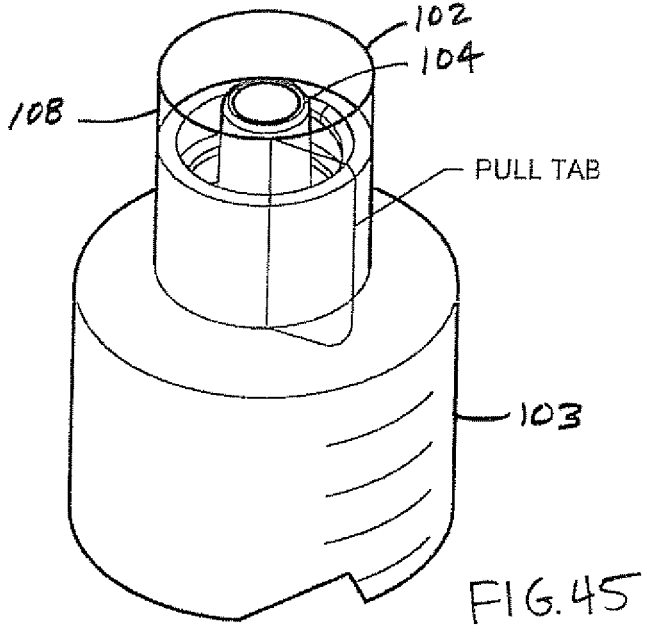
Figure 46:
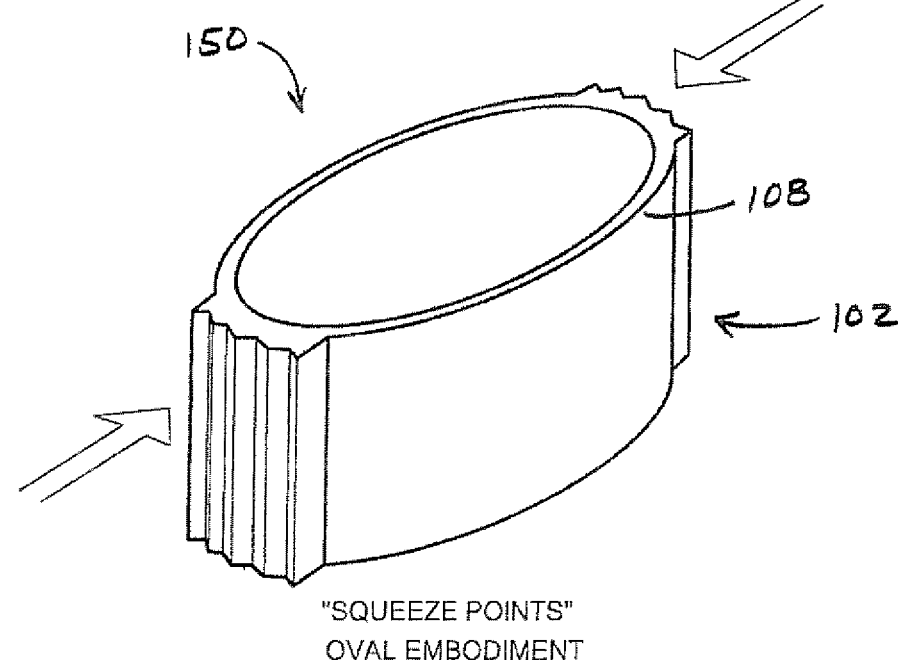
Figure 47:
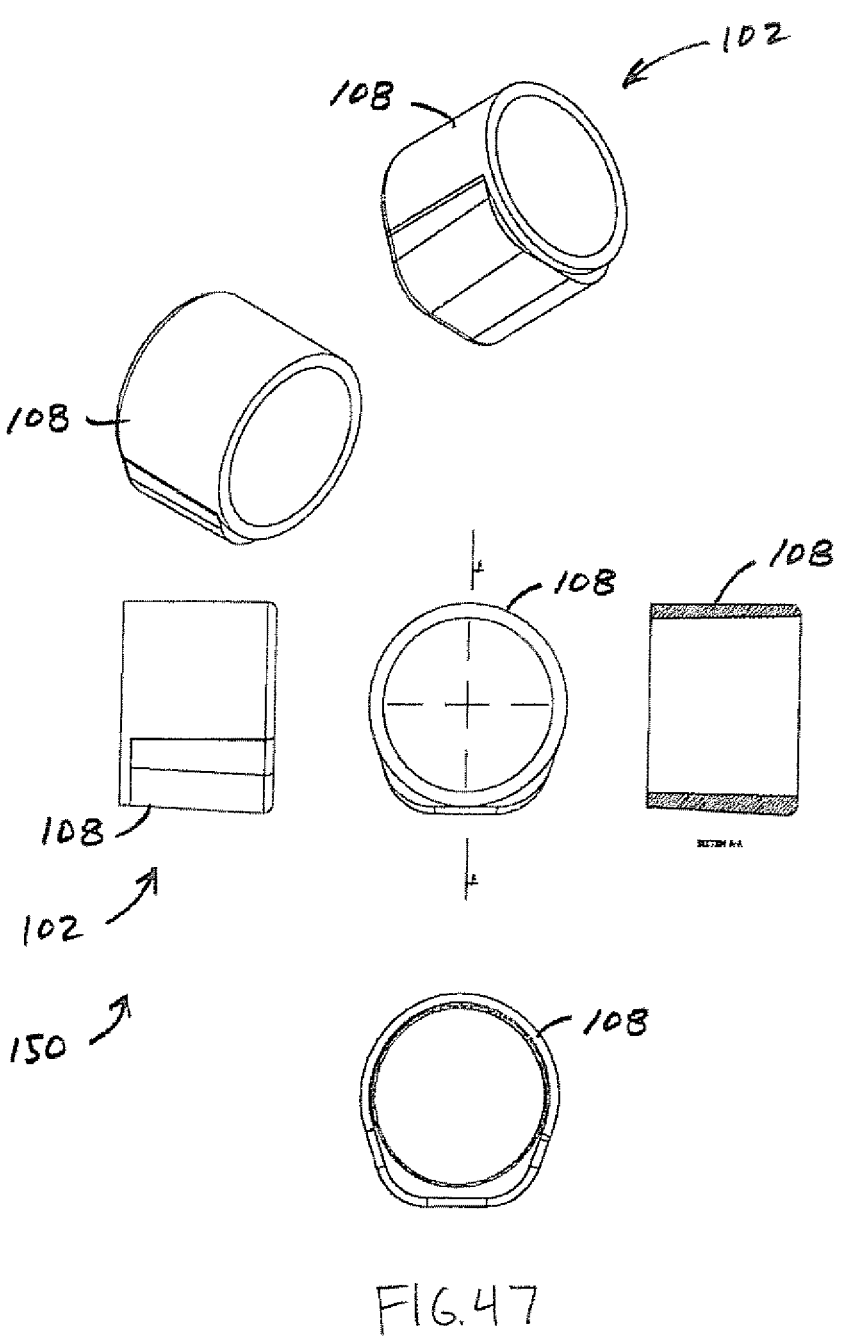
Figure 48:
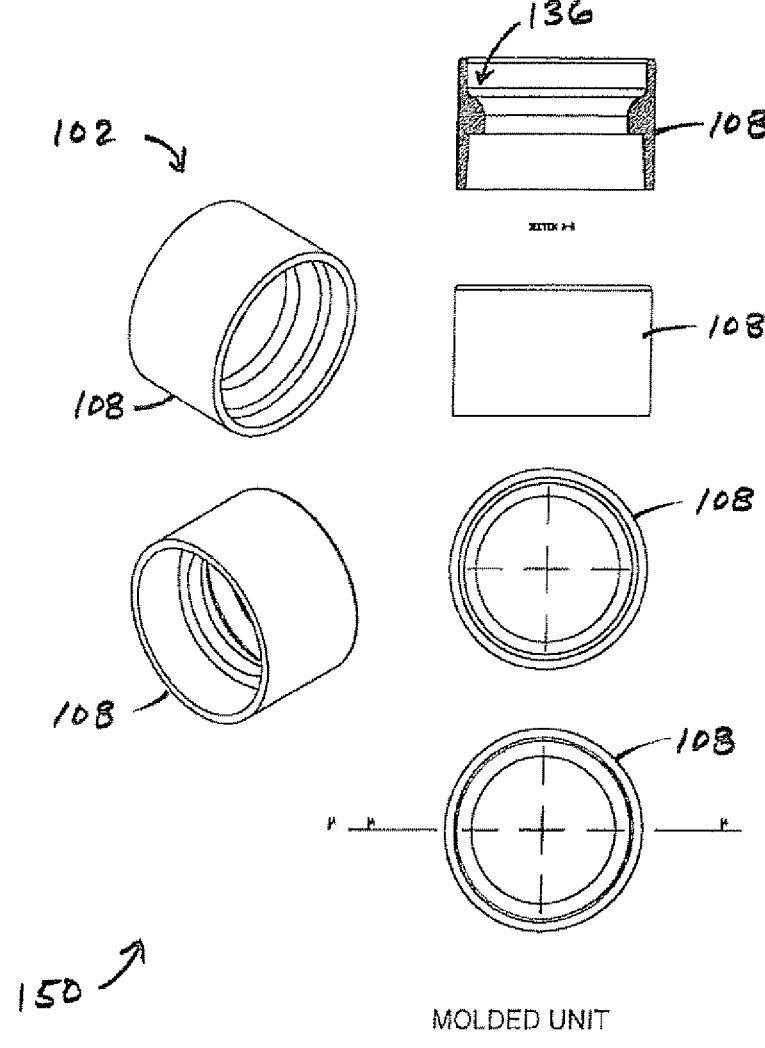
Figure 49:
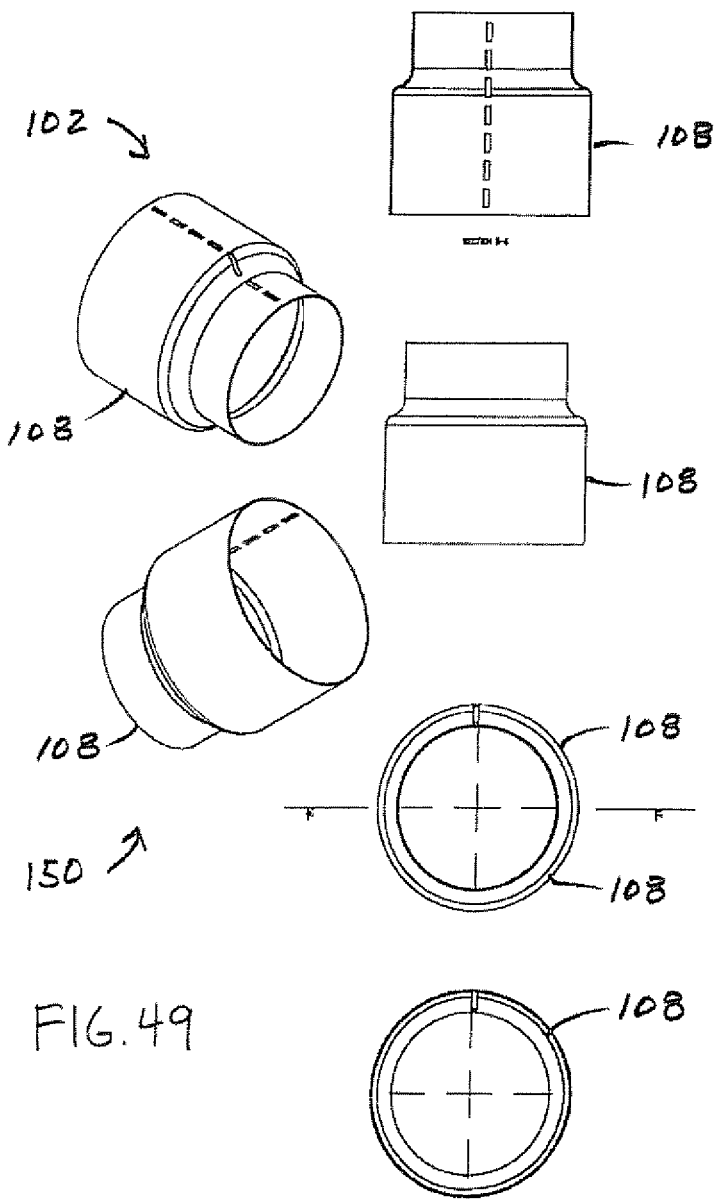
Figure 50:
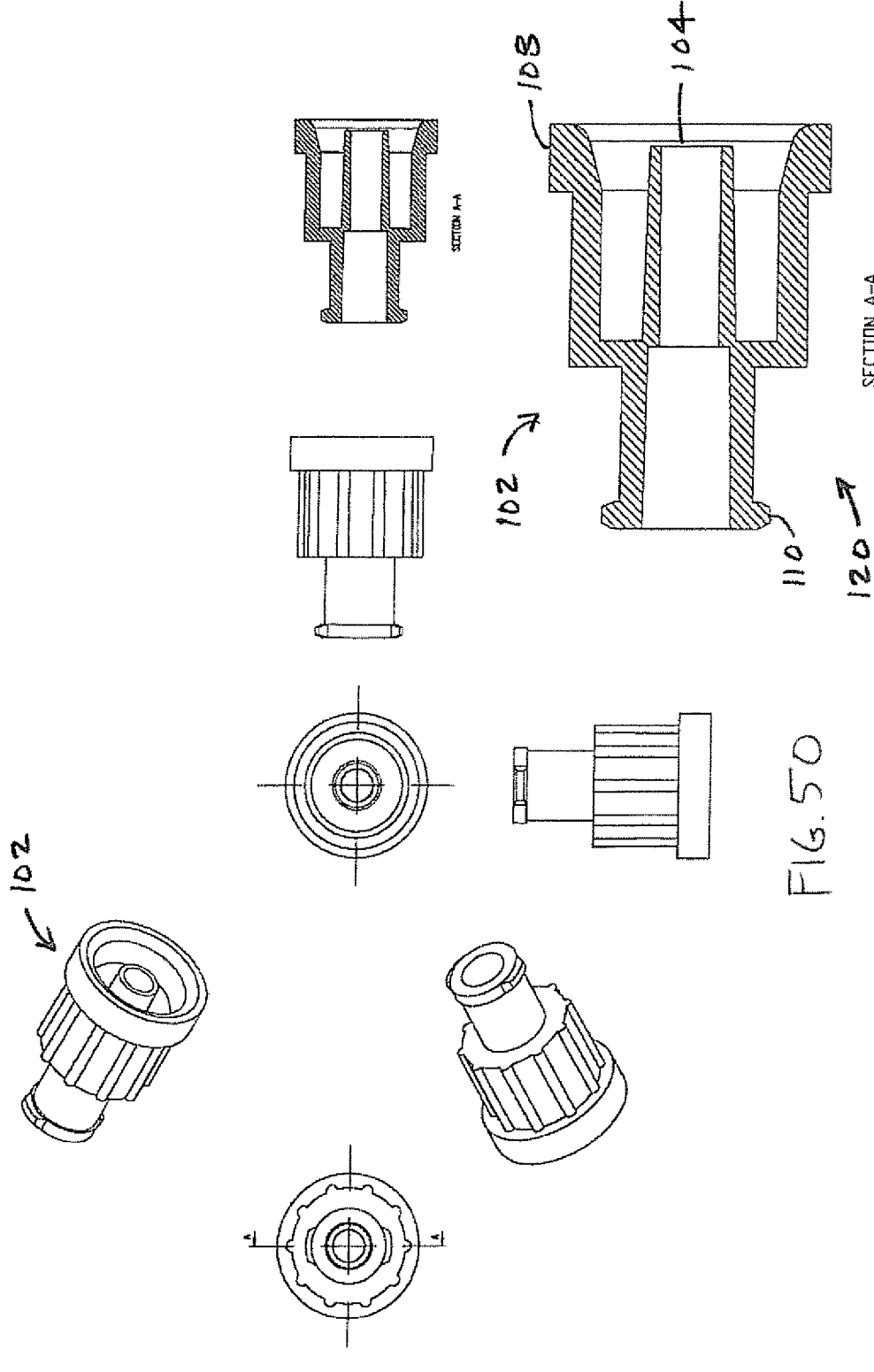
Figure 51:
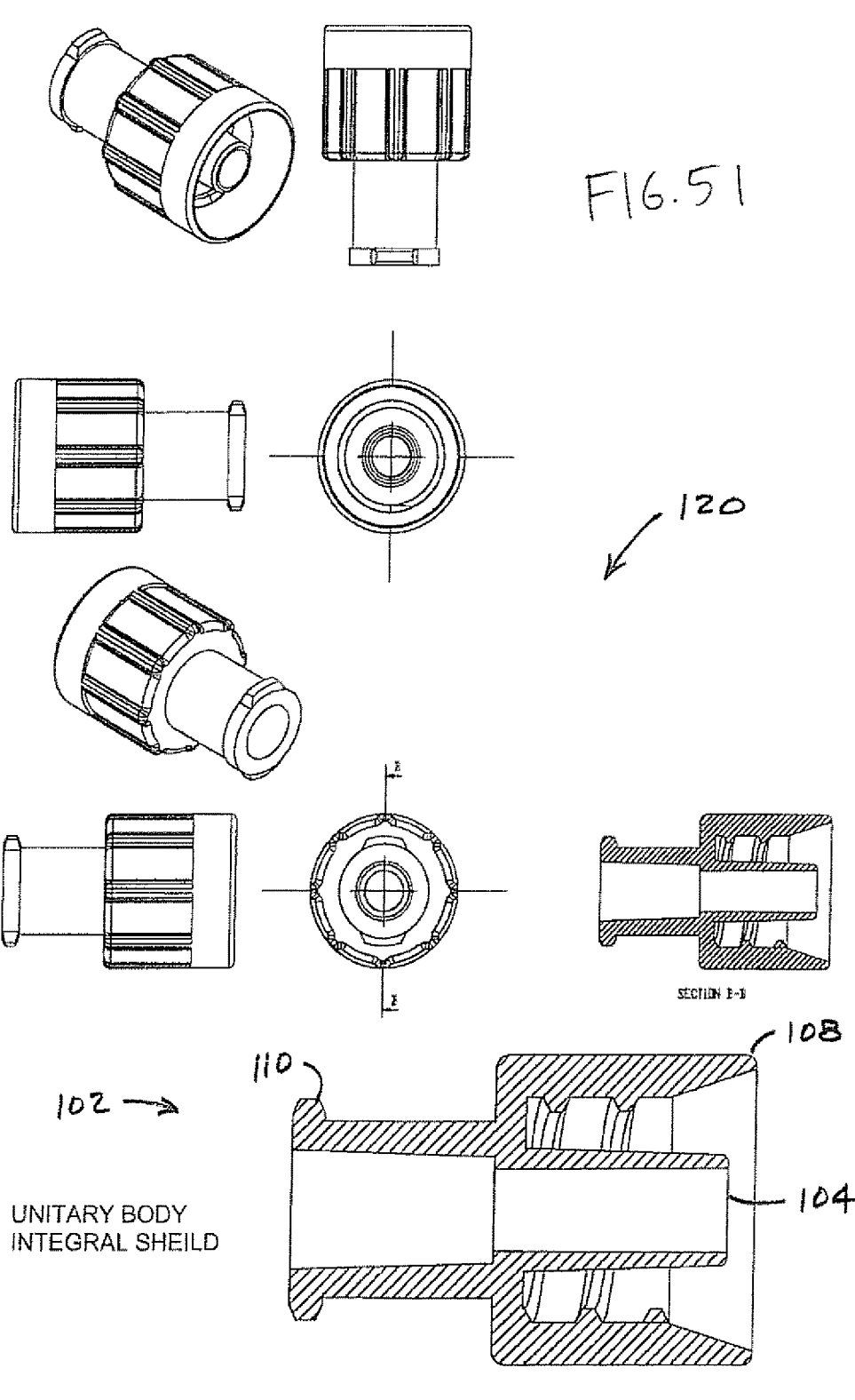
Figure 52:
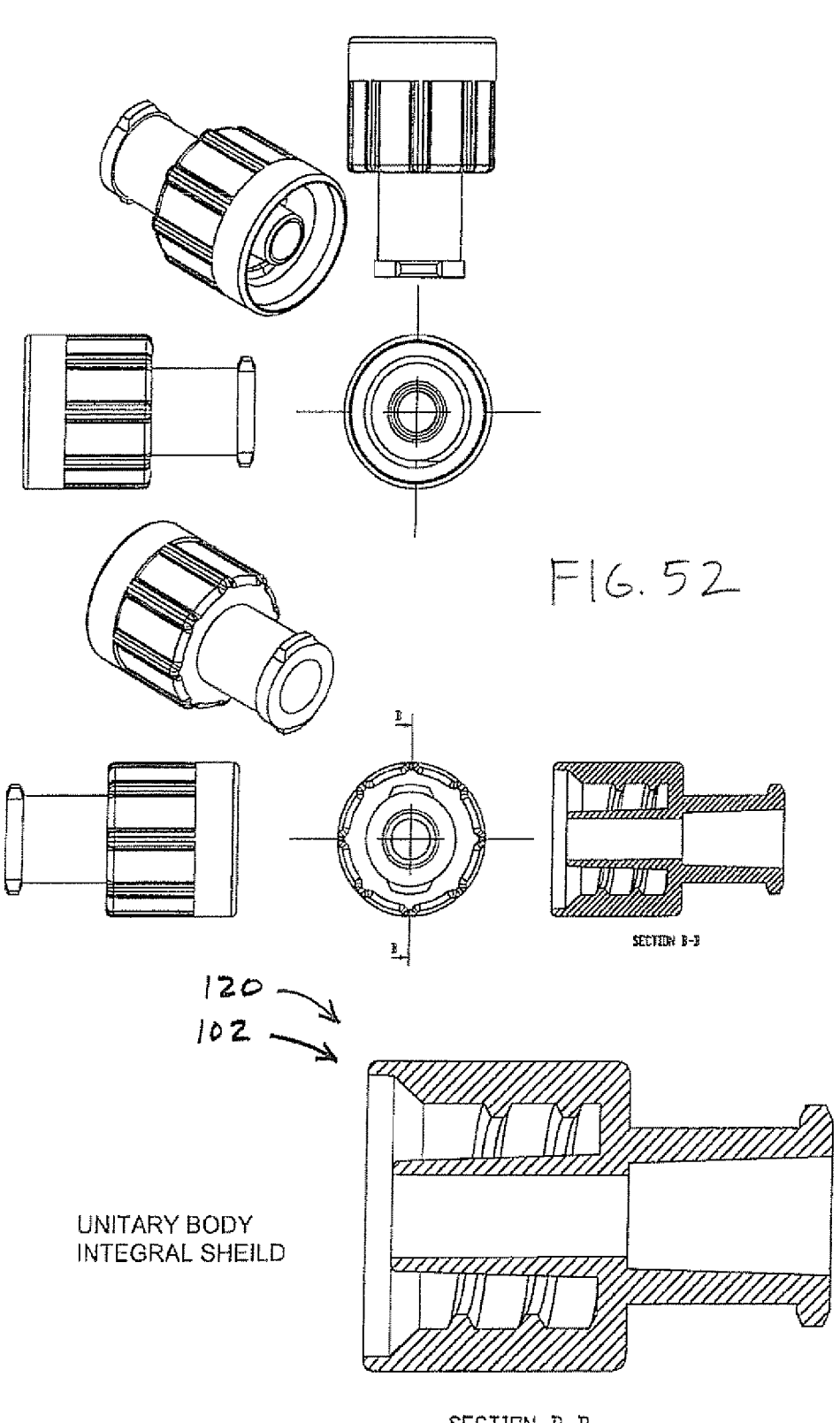
Figure 53:
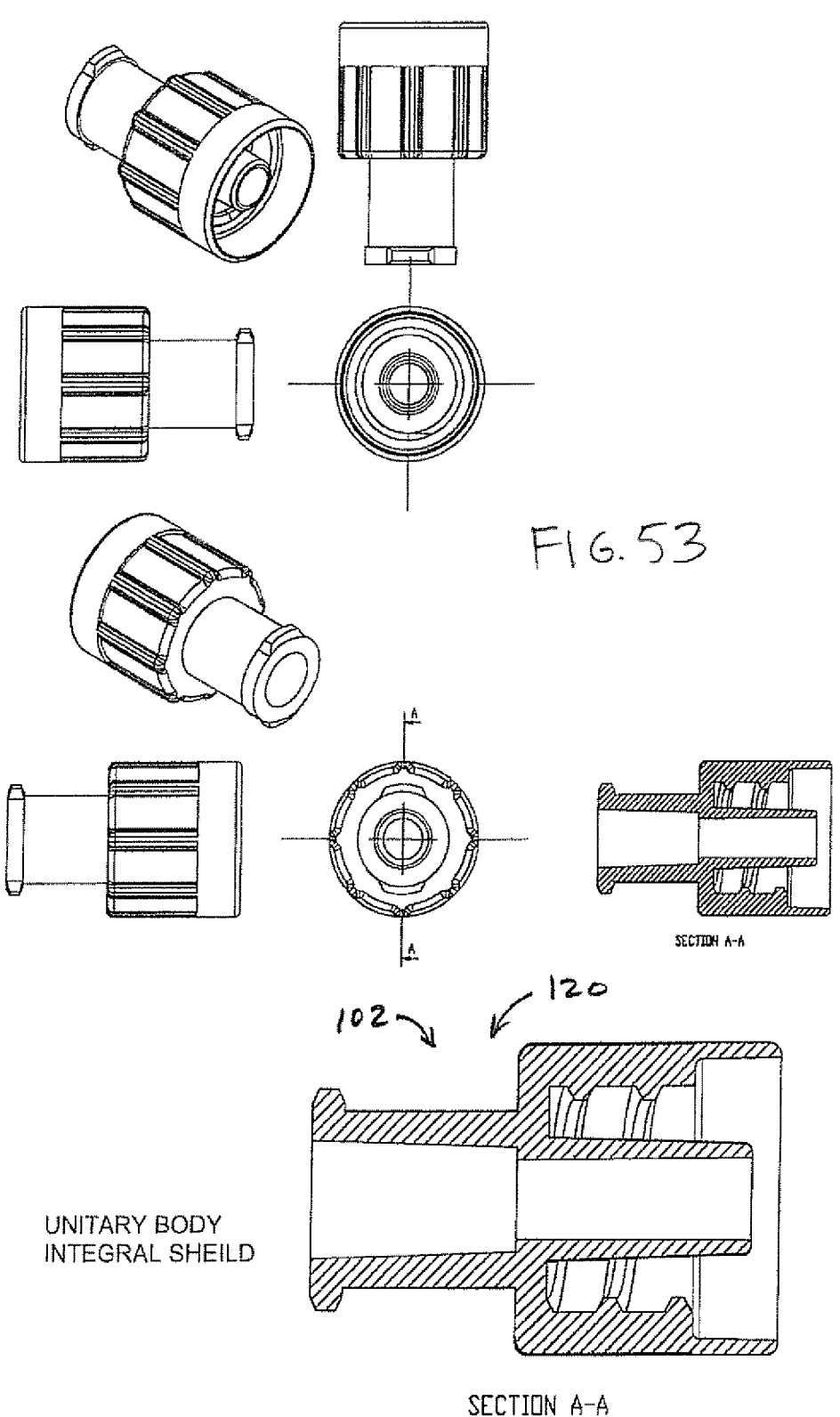
Figure 54:
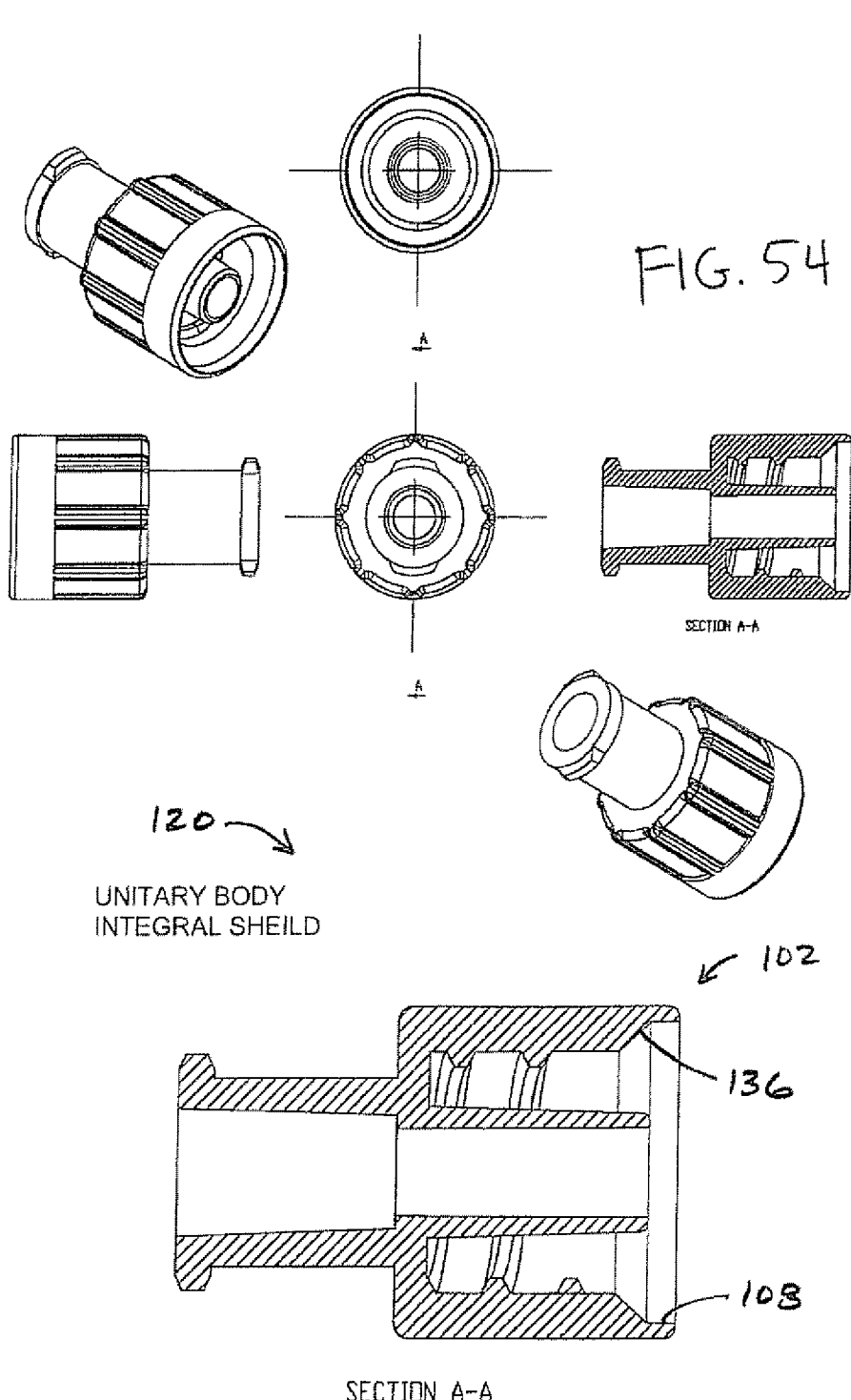
Figure 55:
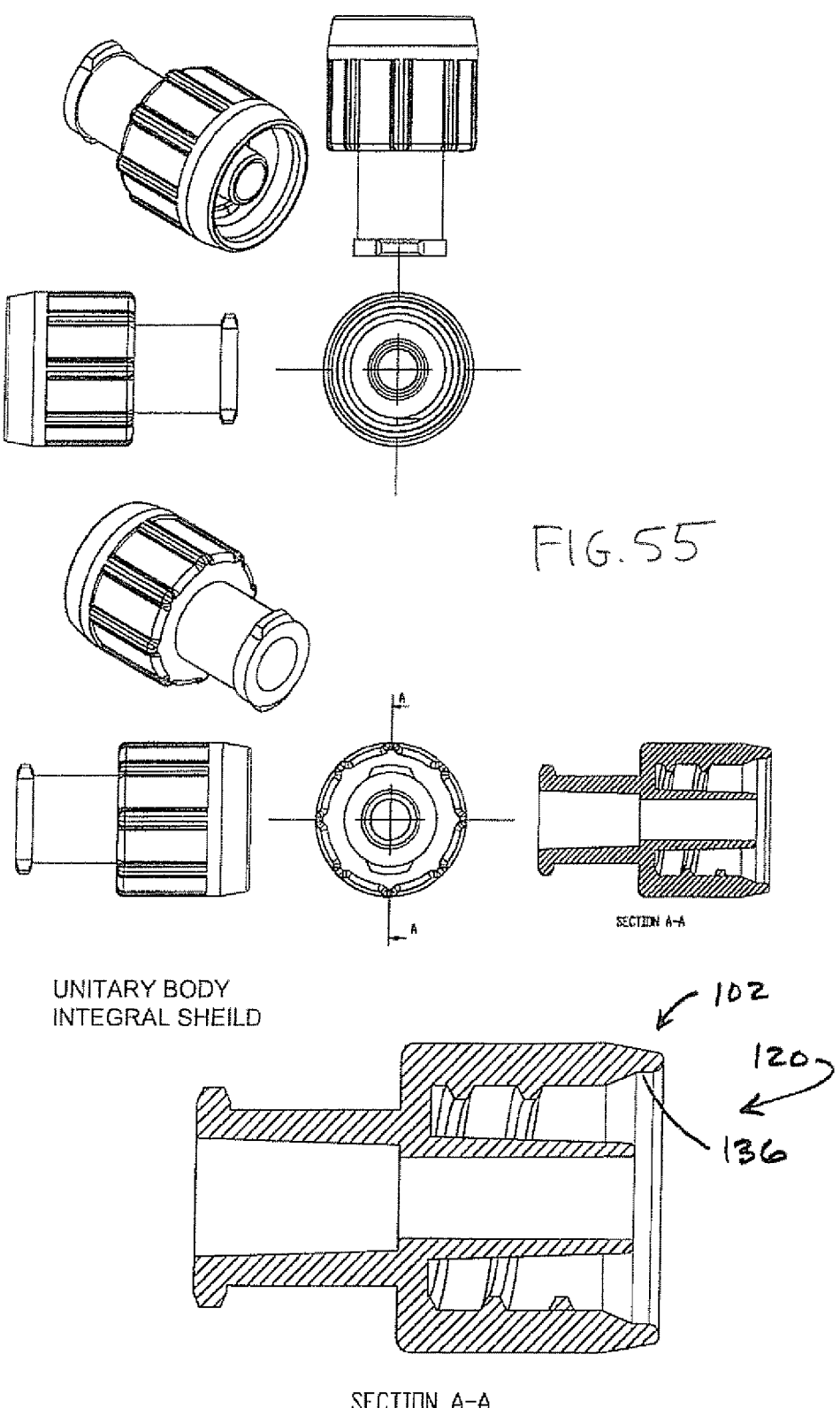
Figure 56:
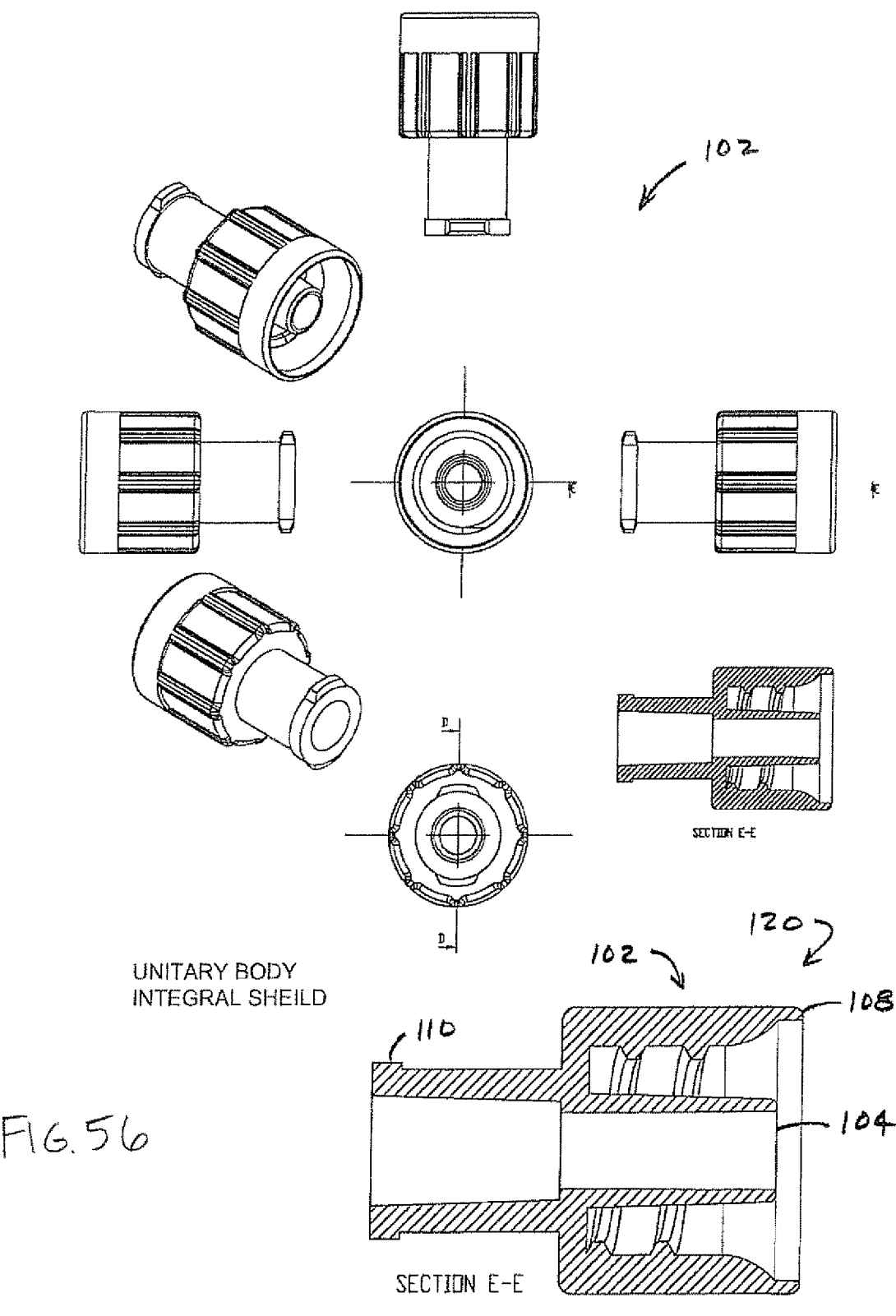
Figure 57:
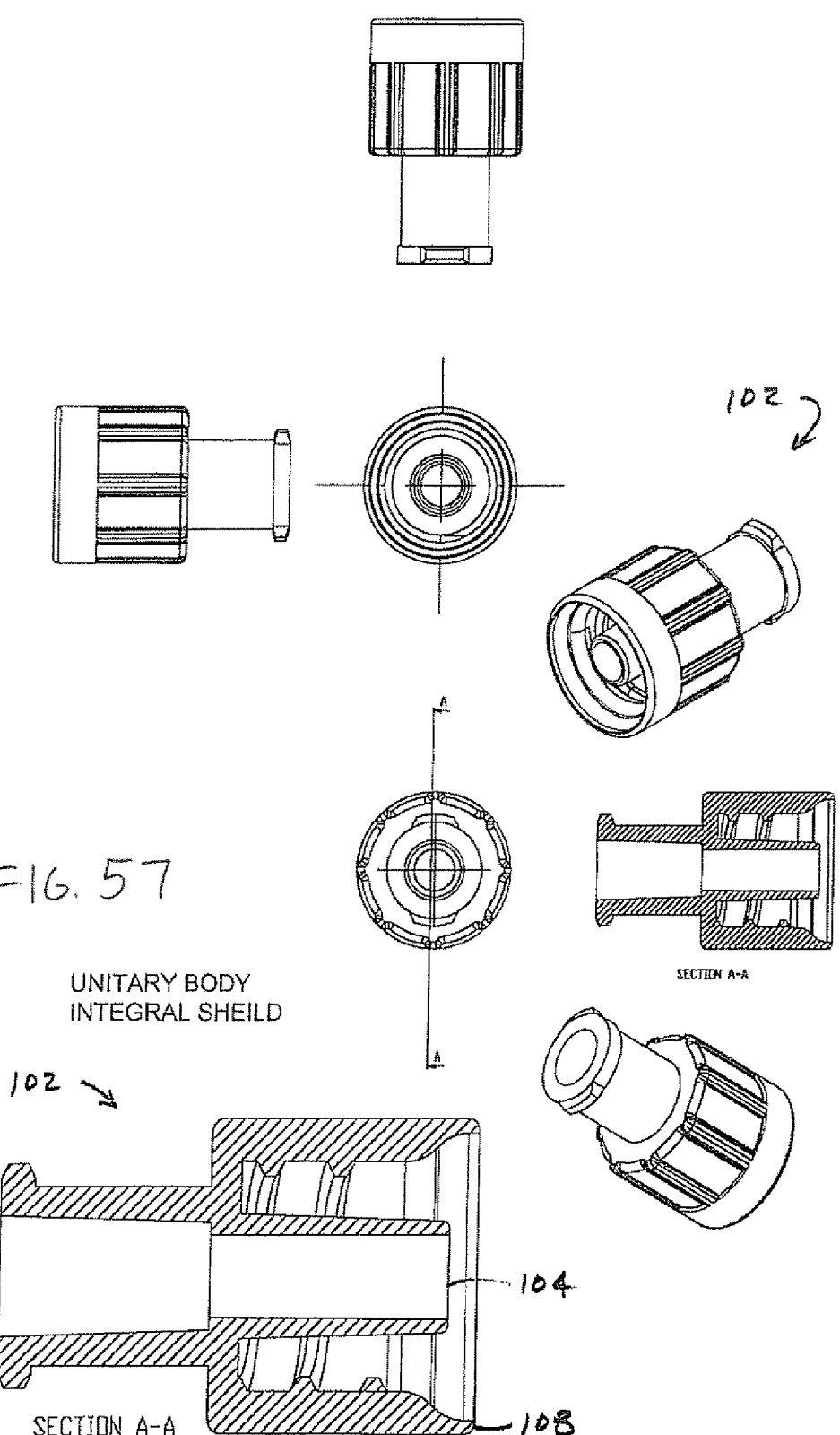
Figure 58:
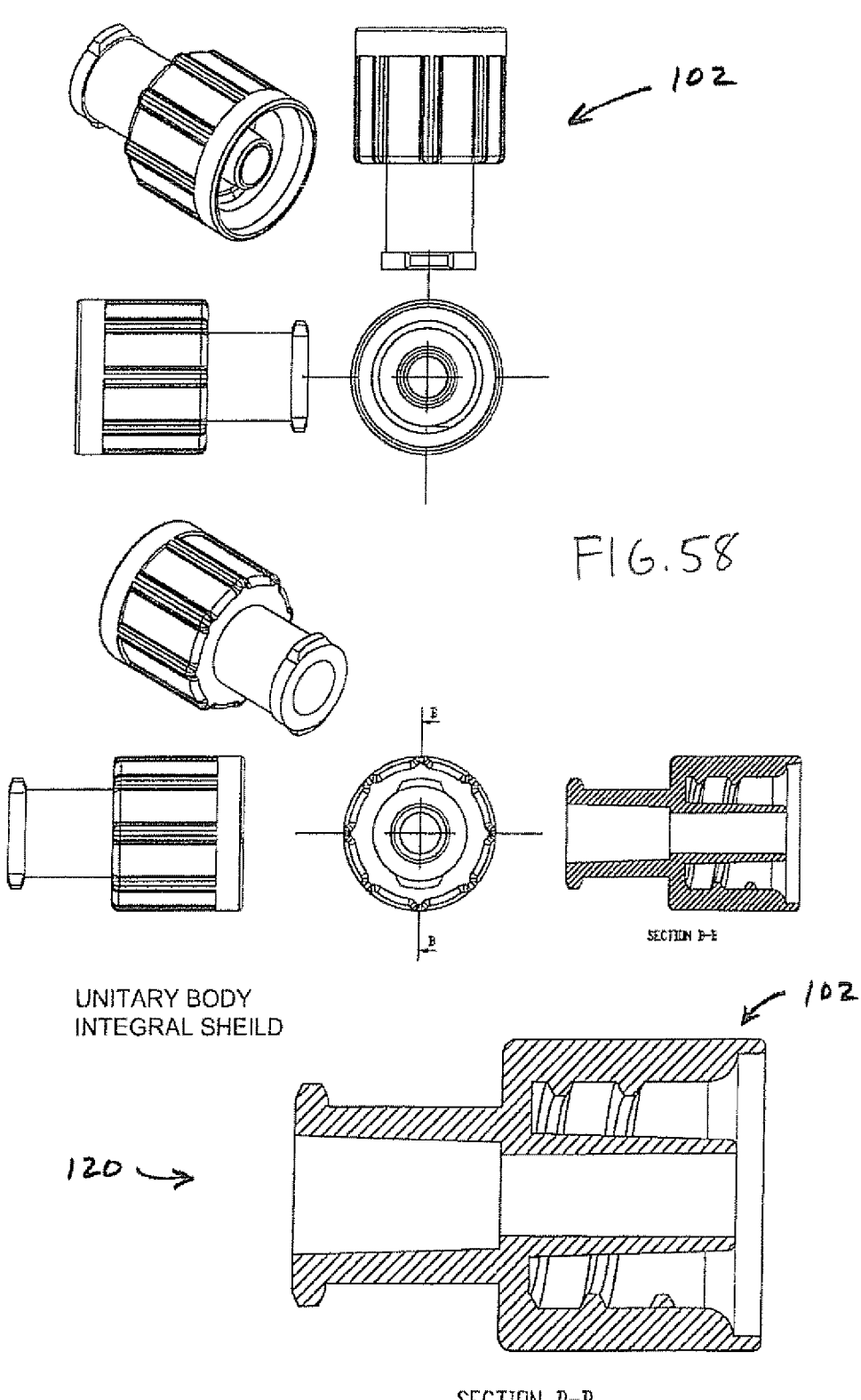
Figure 59:
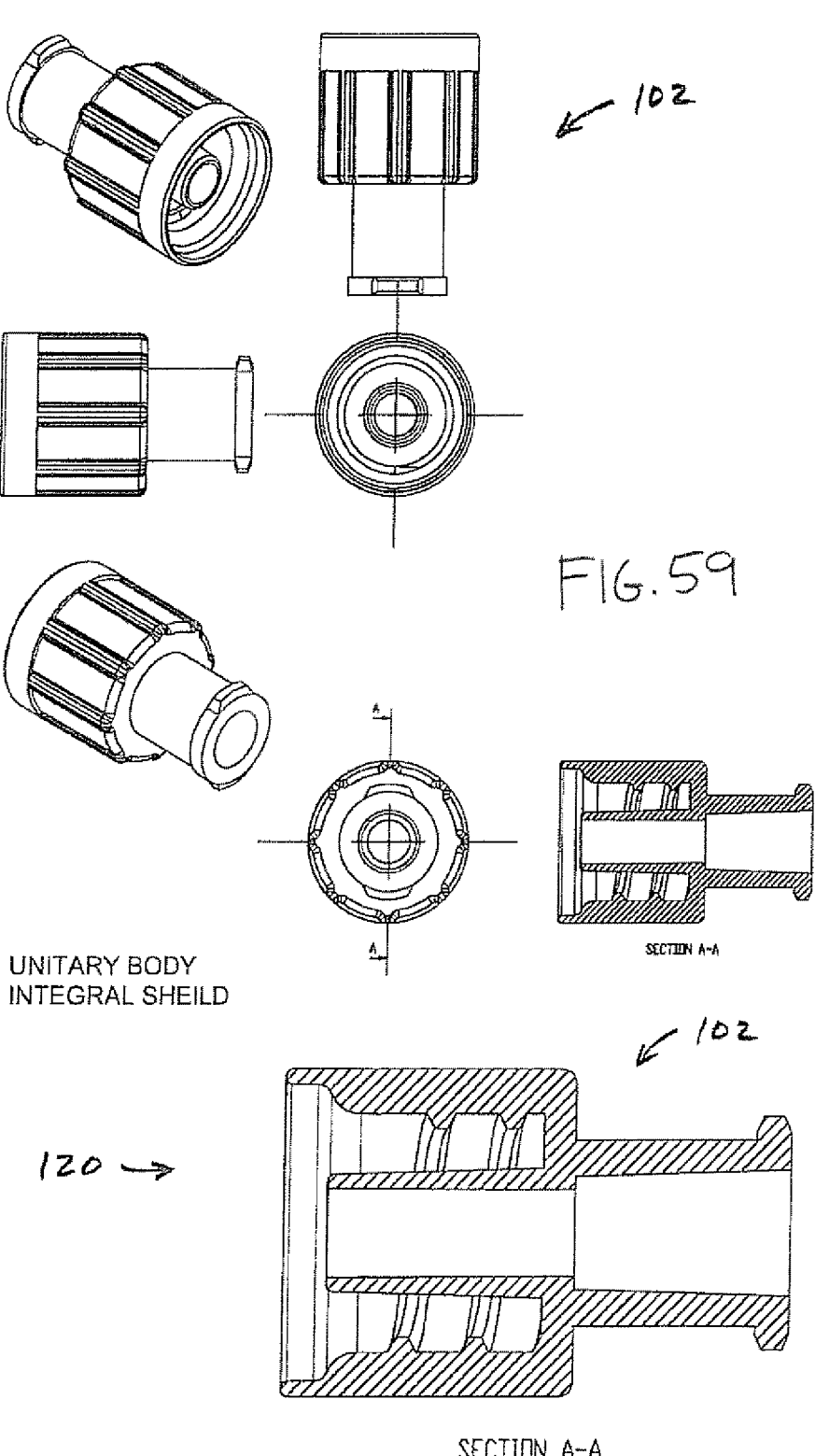
Figure 60:
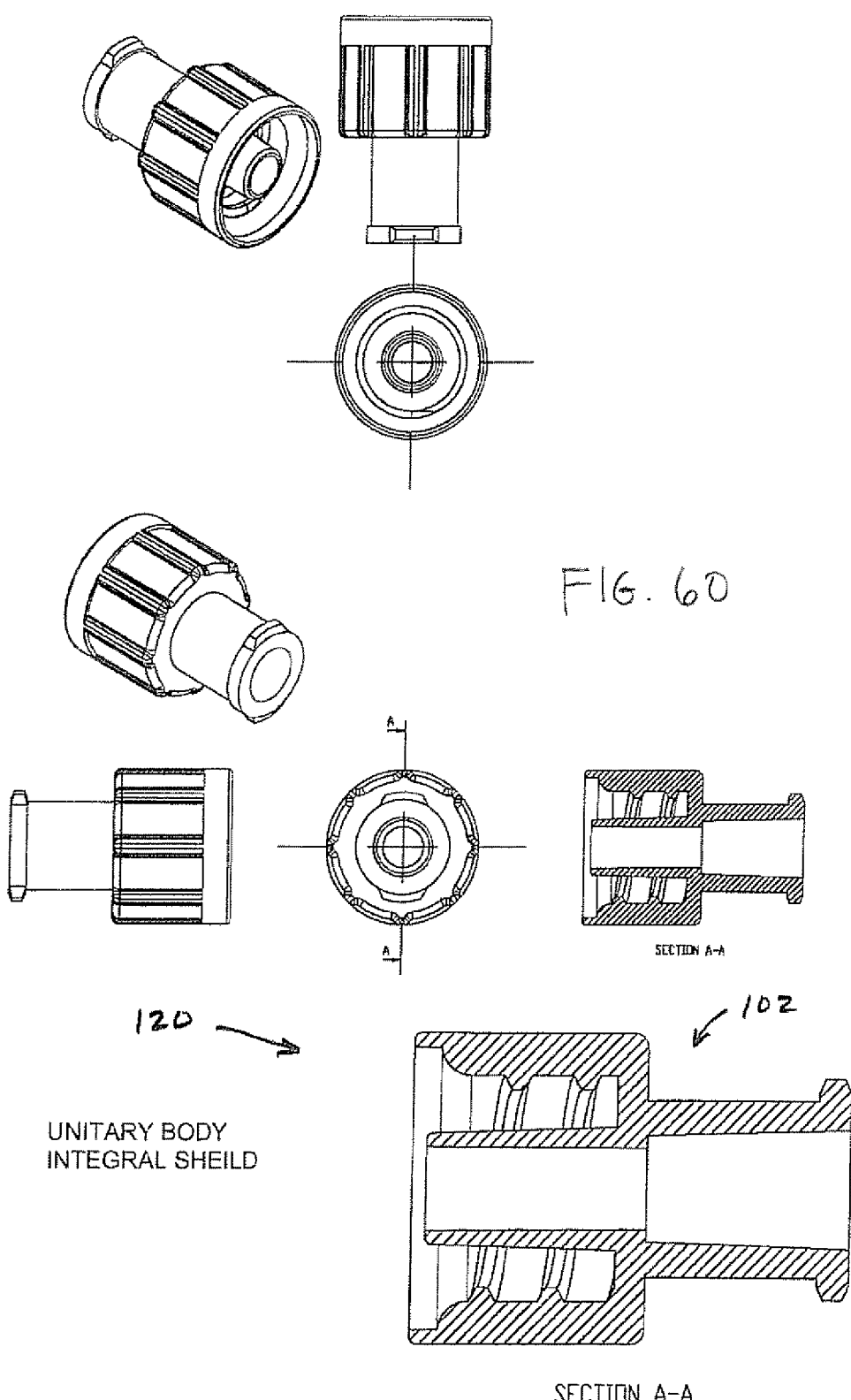
Figure 61:
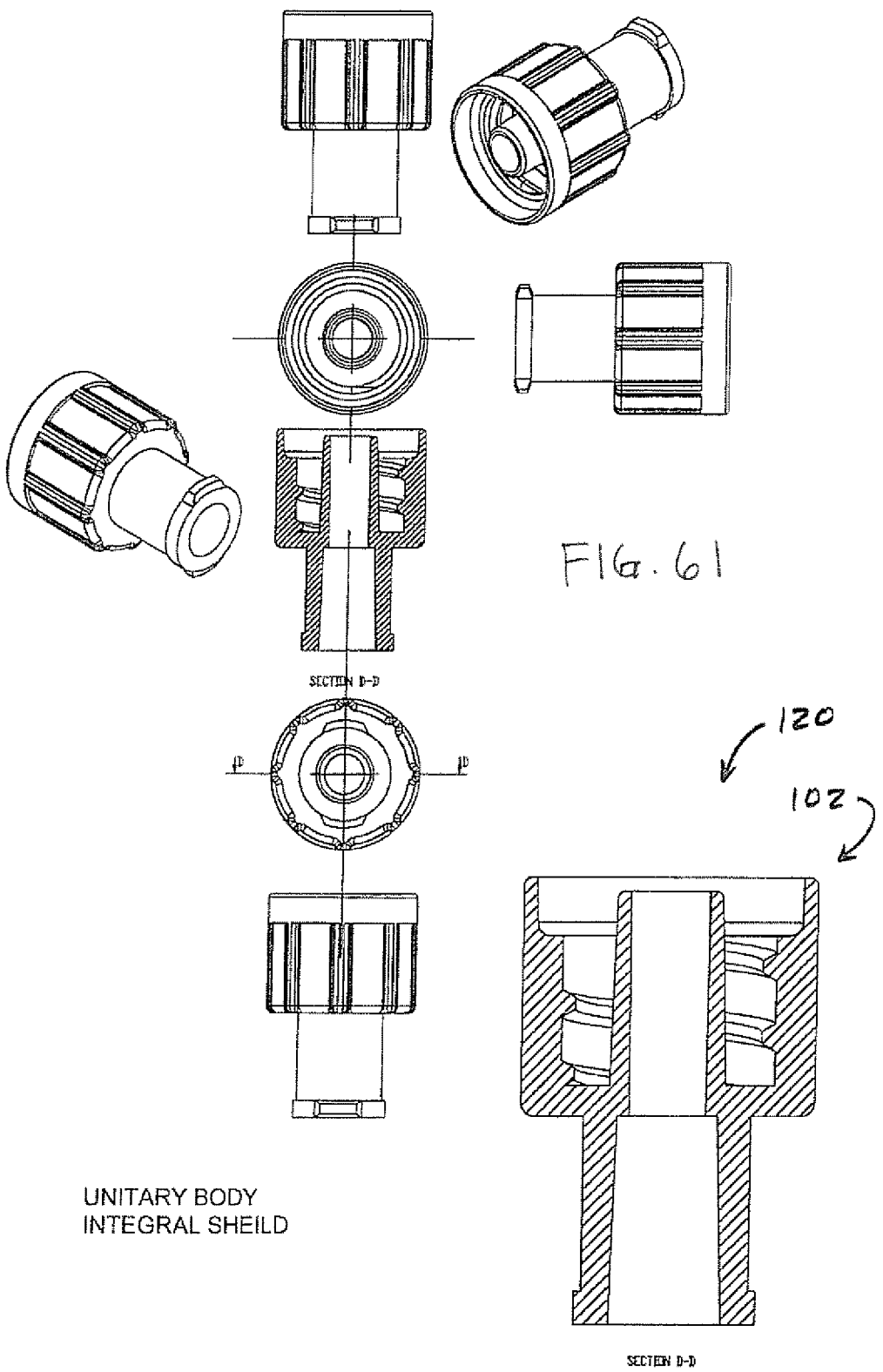
Figure 62:
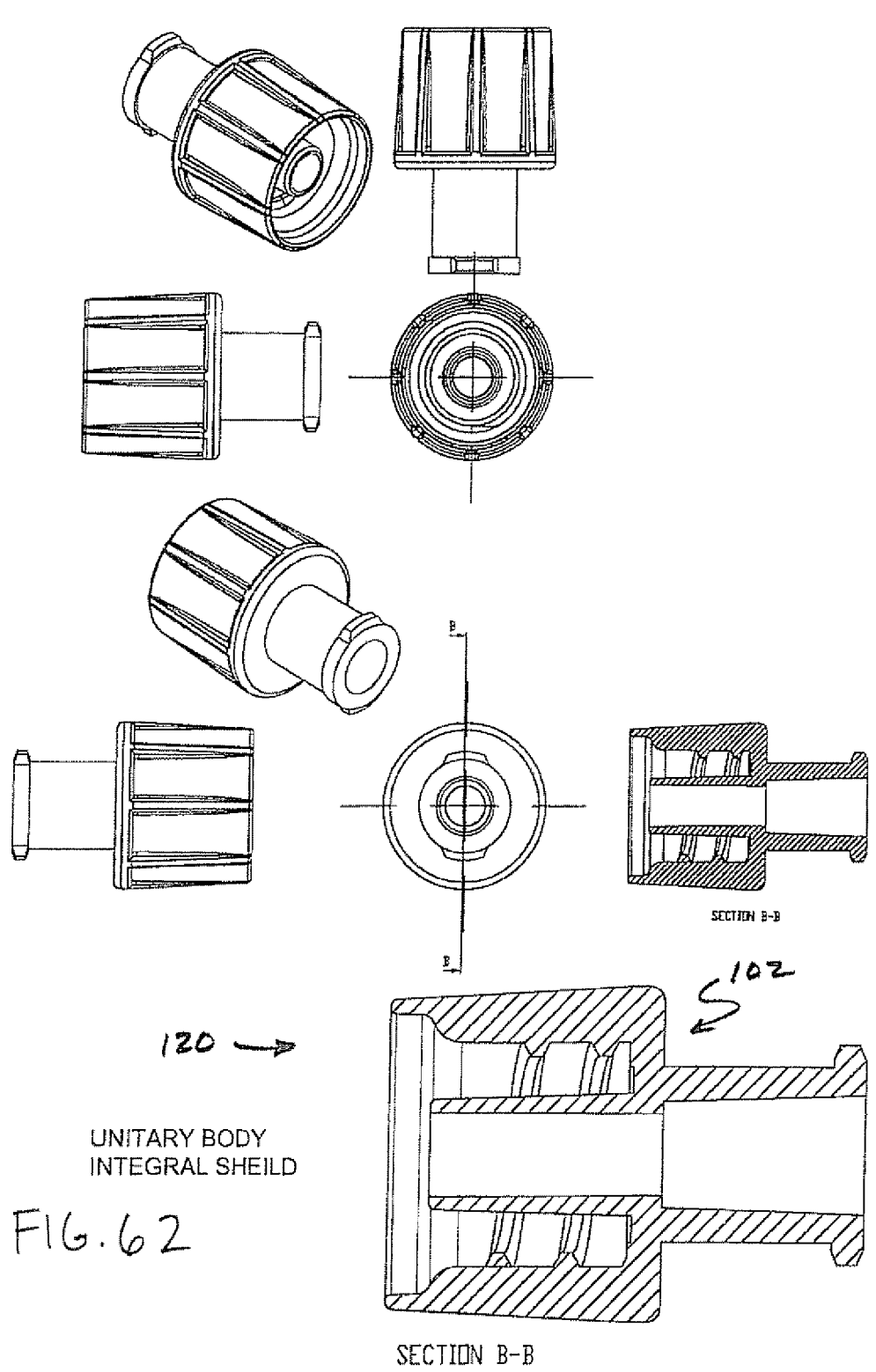
Figure 63:
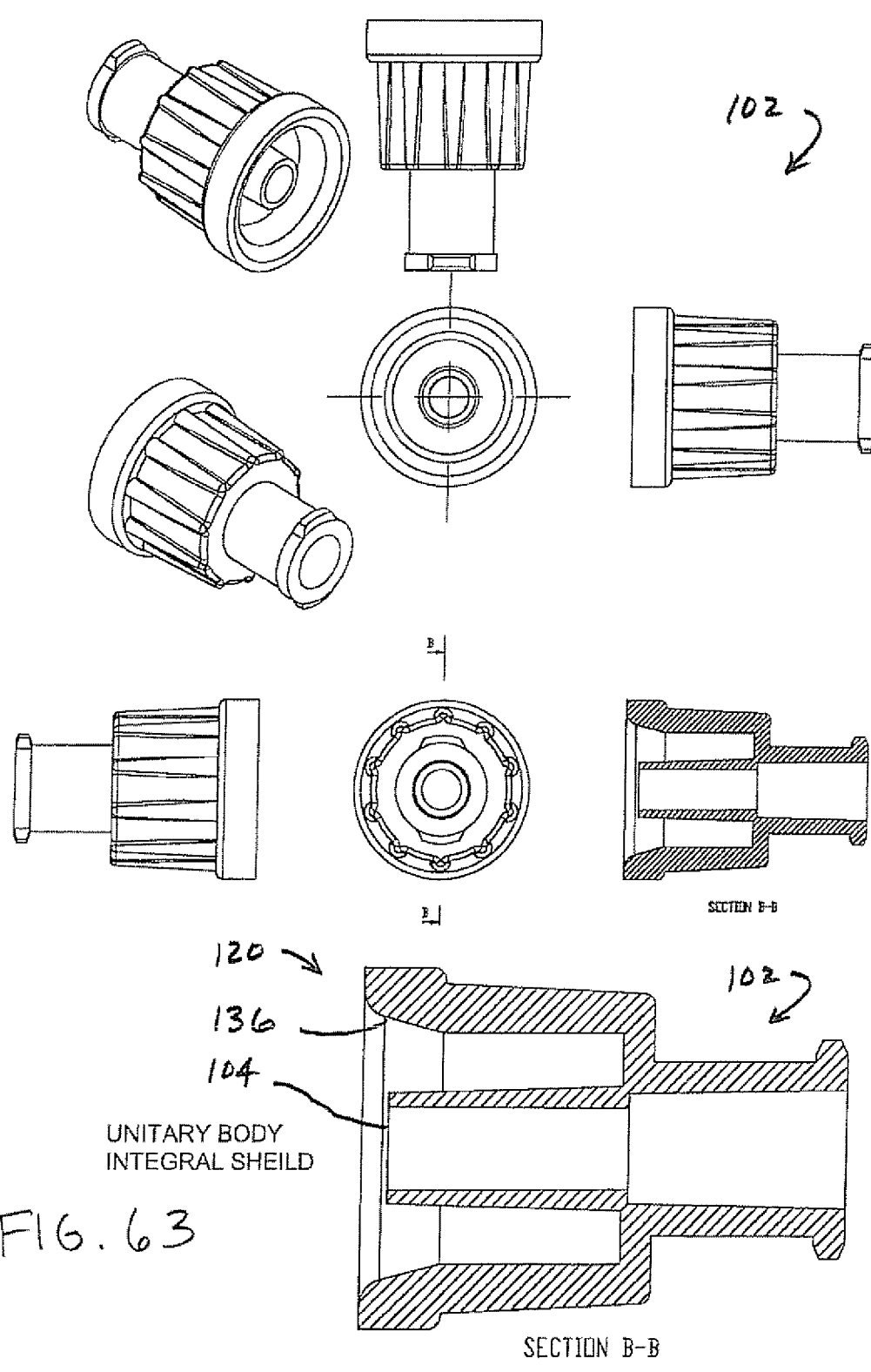
Figure 64:
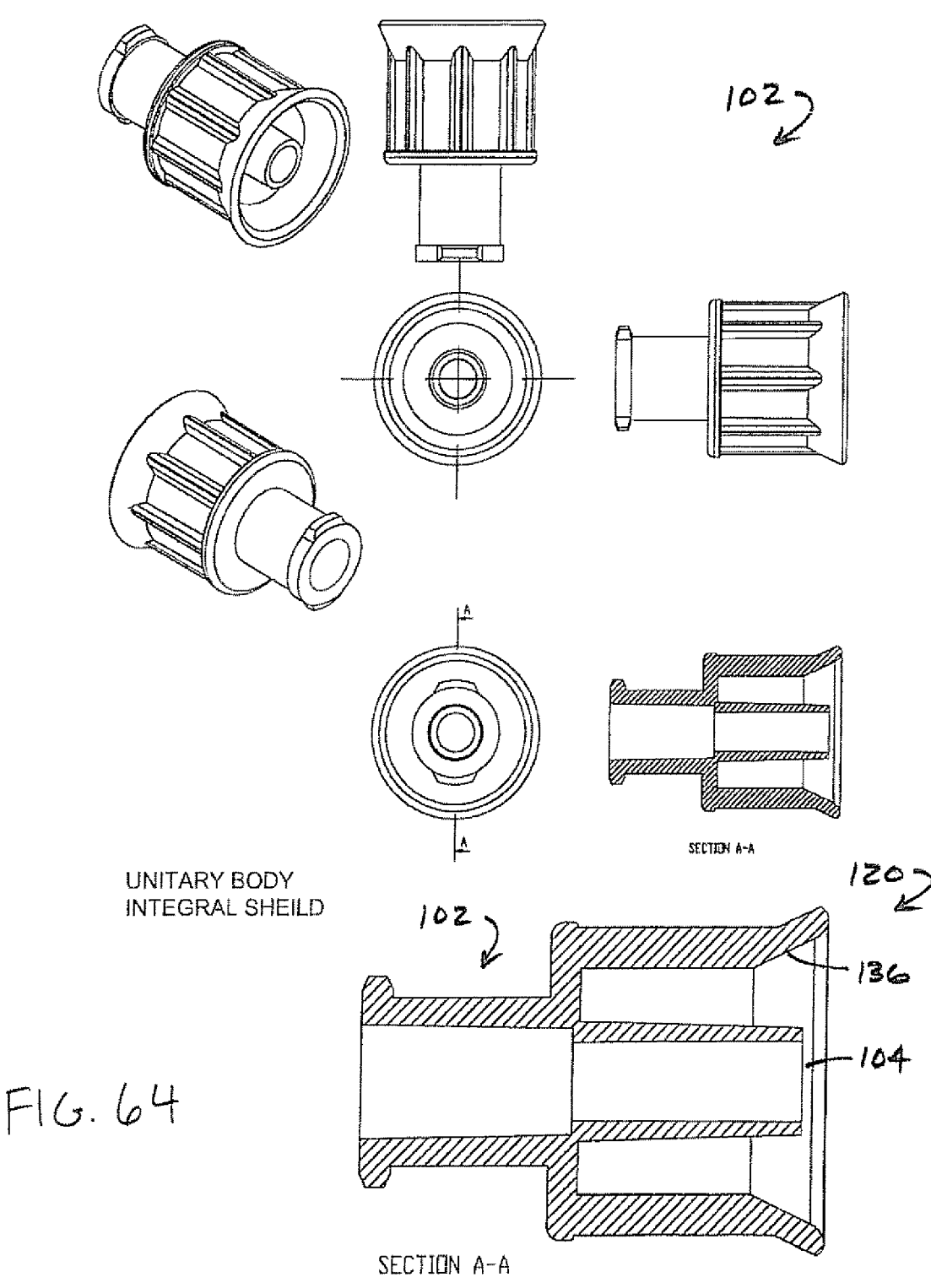
Figure 65:
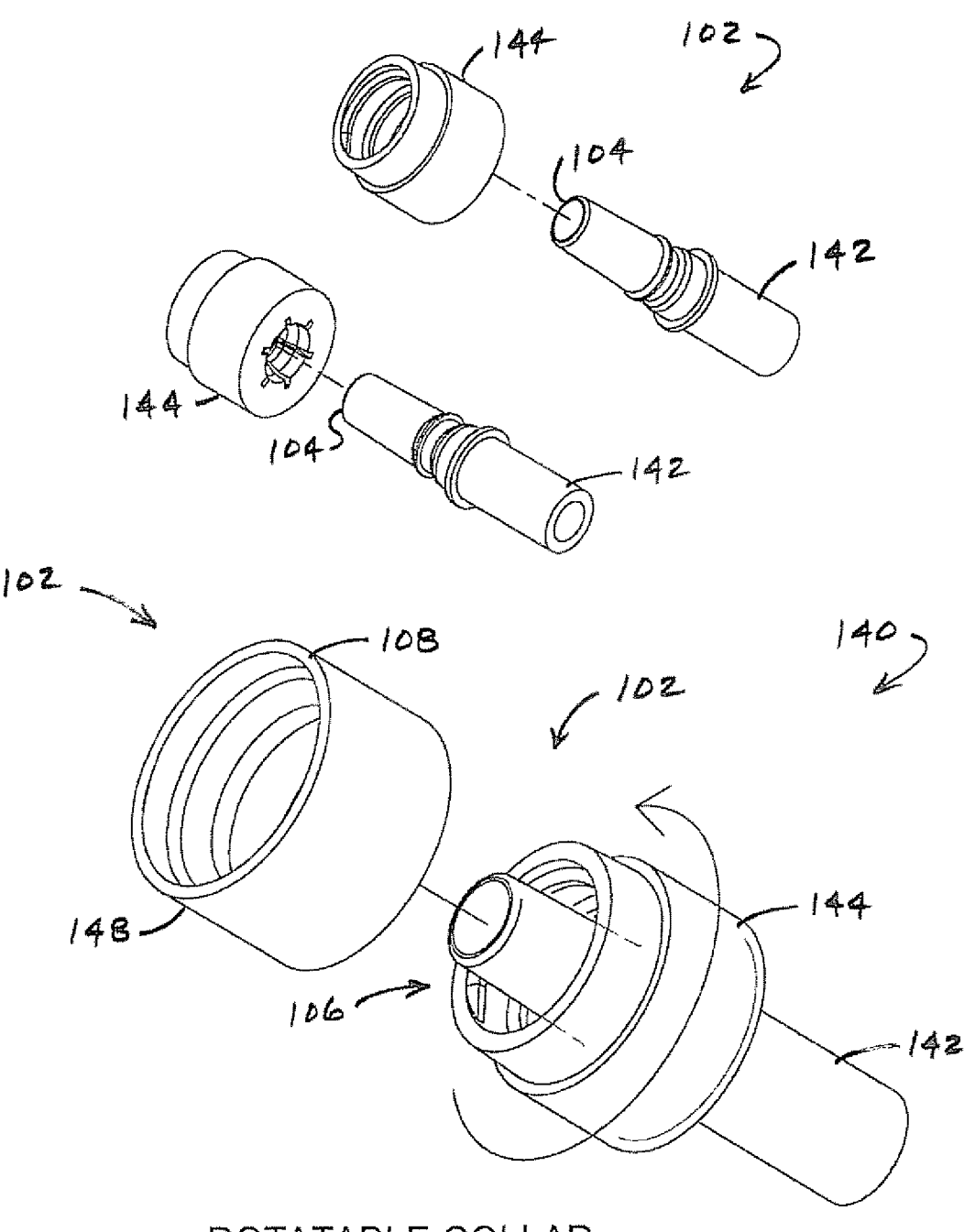
Figure 66:
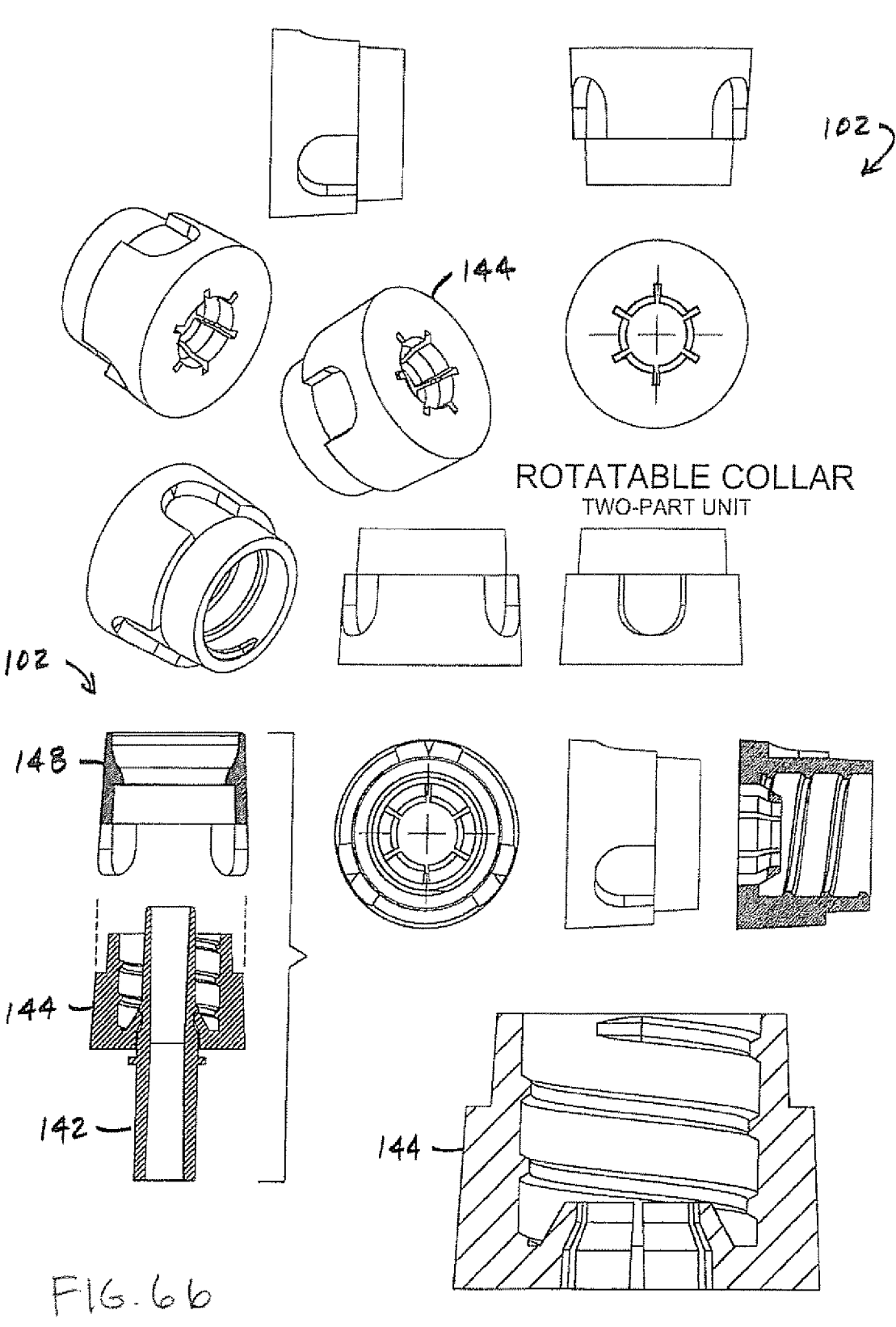
Figure 67:
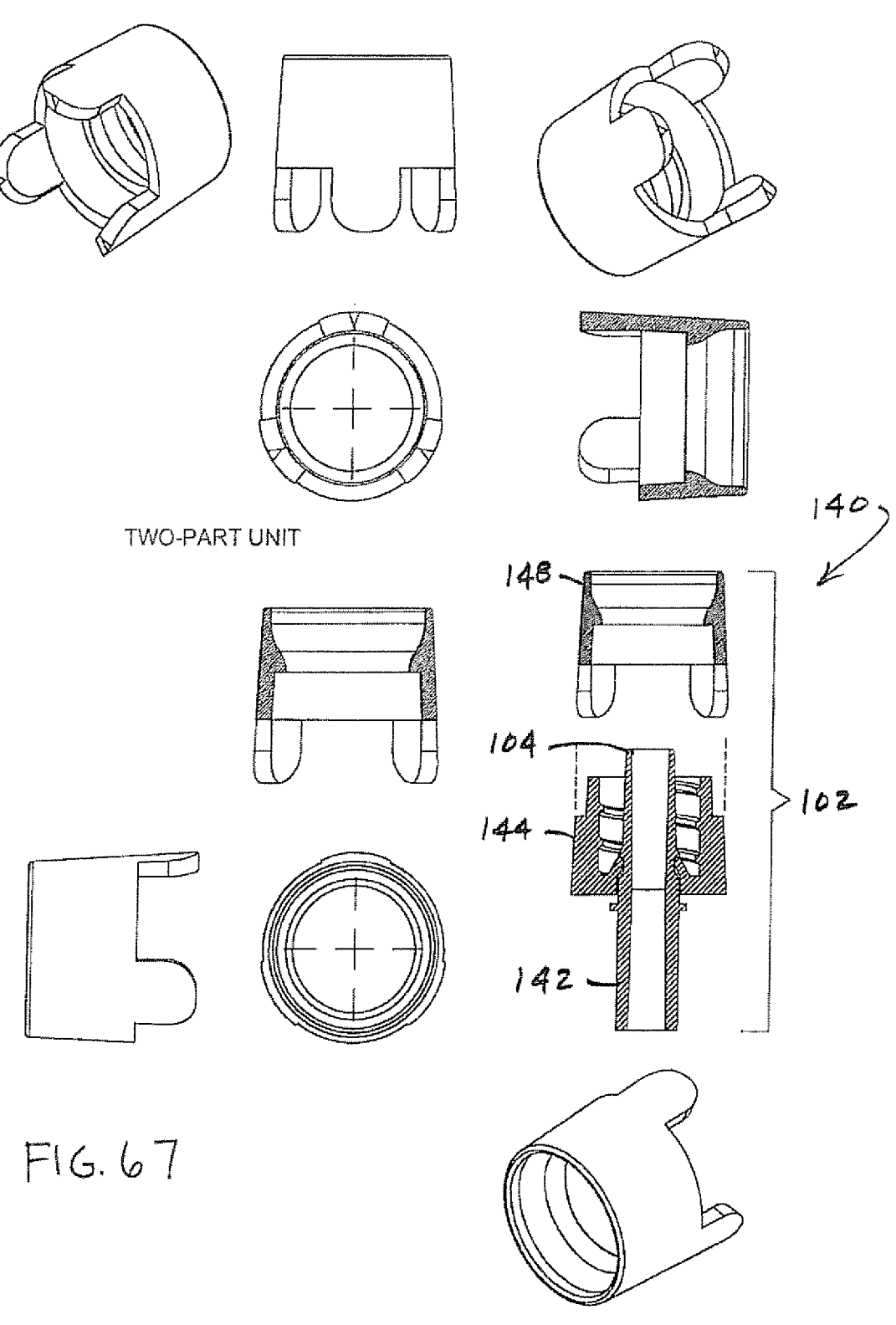
Figure 68:
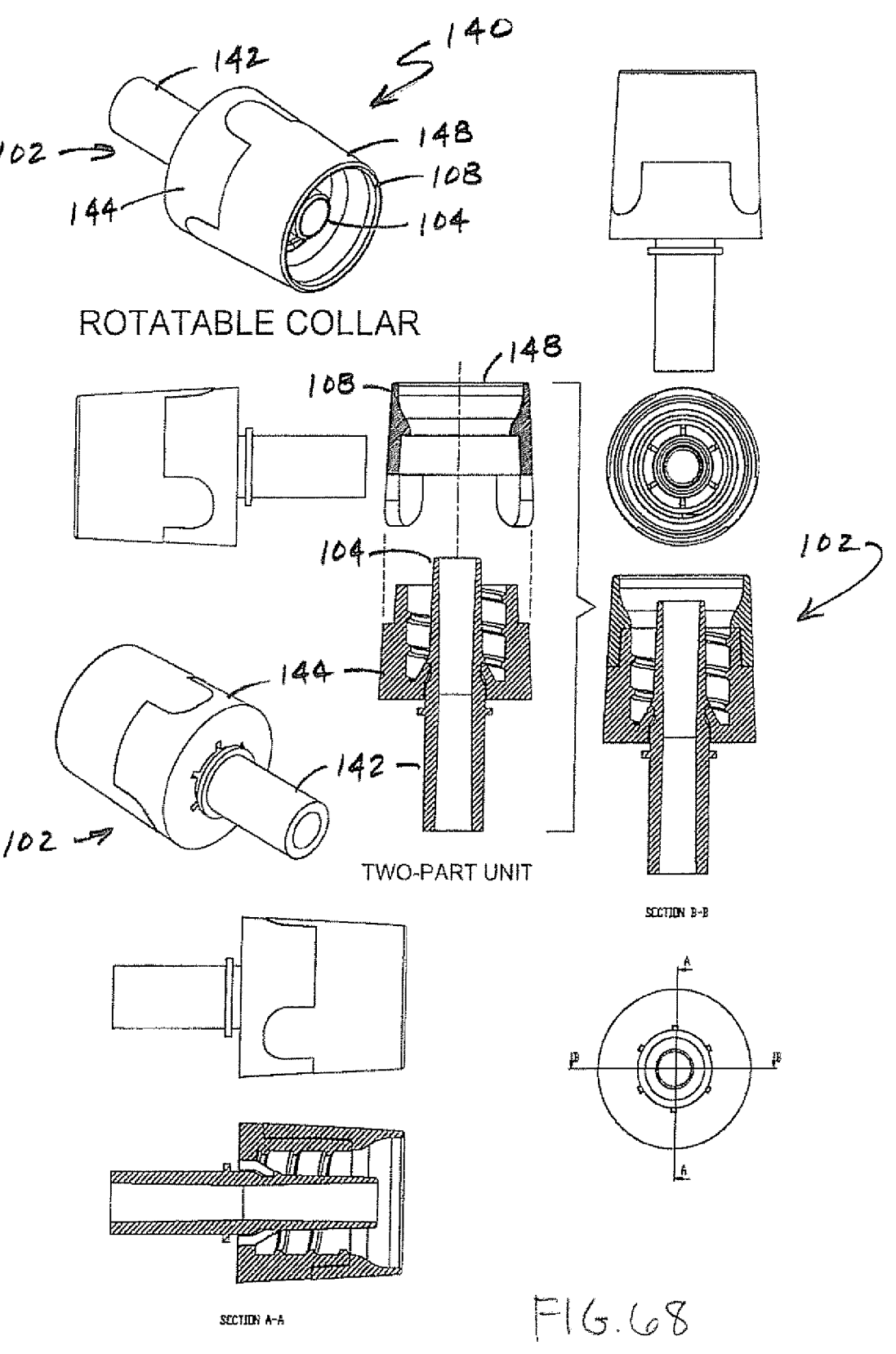
Figure 69:
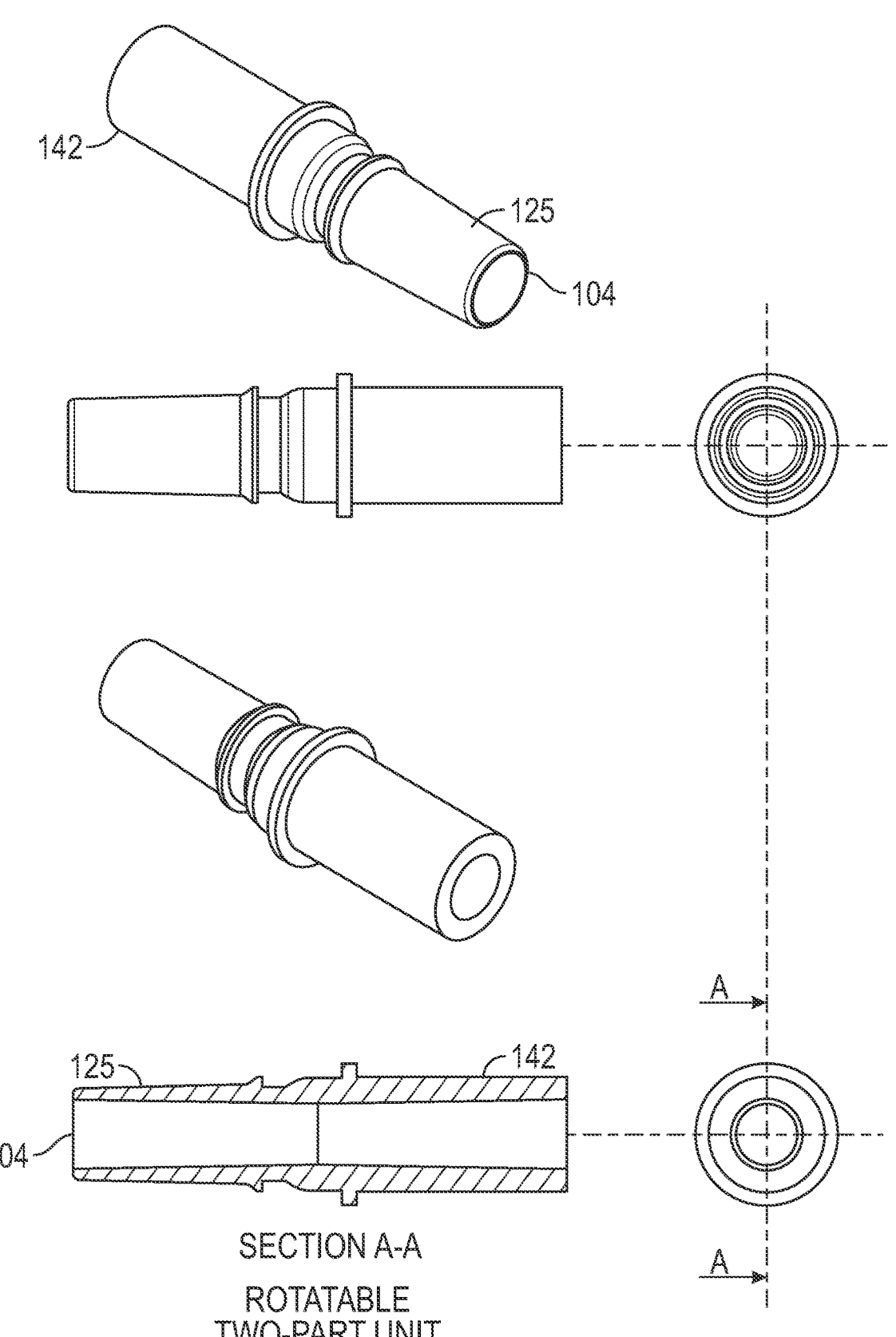
Figure 70:
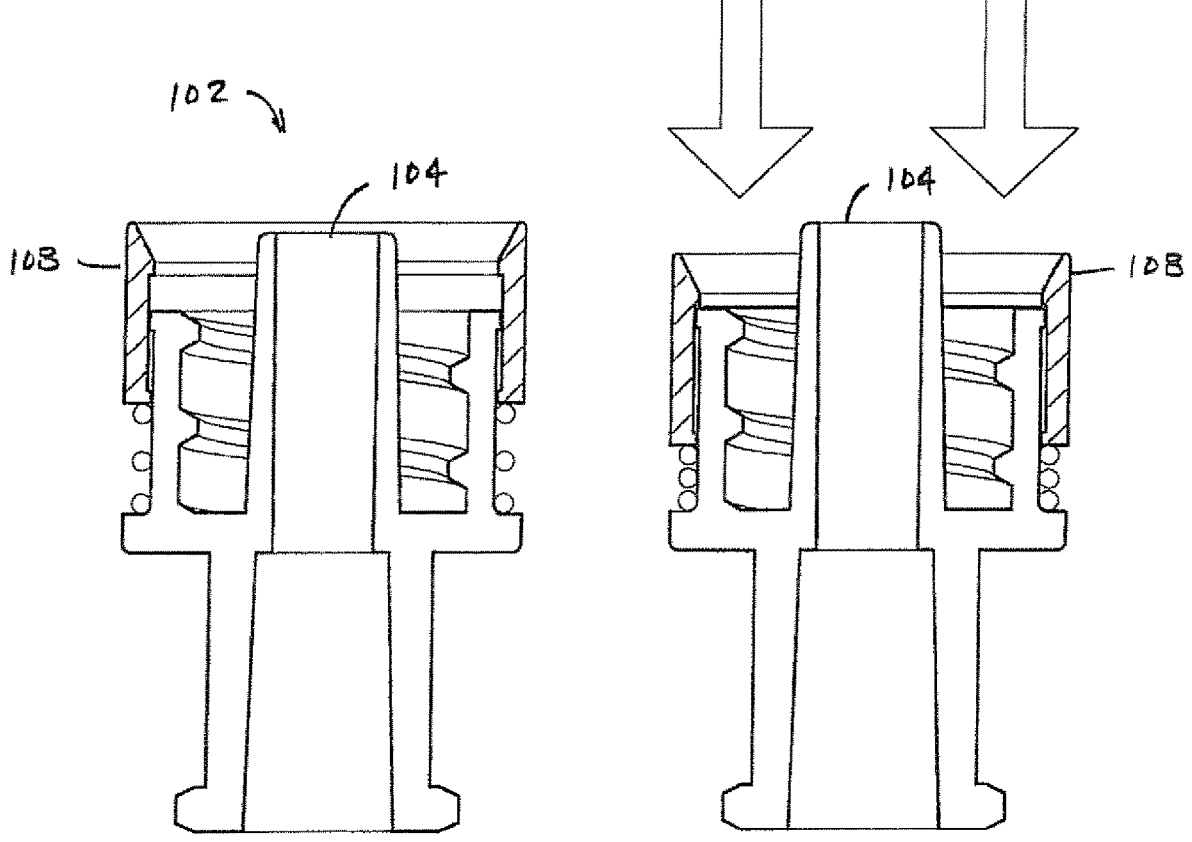
Figure 71:
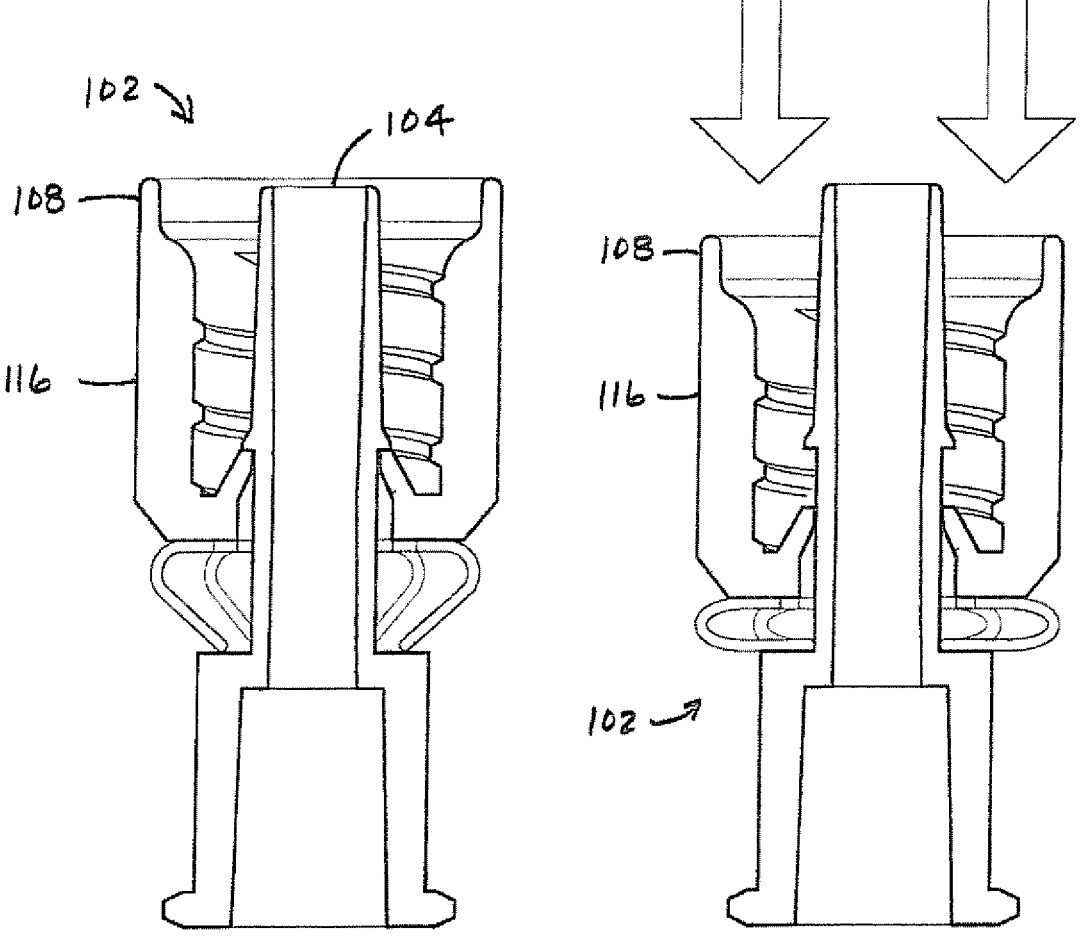
Figure 72:
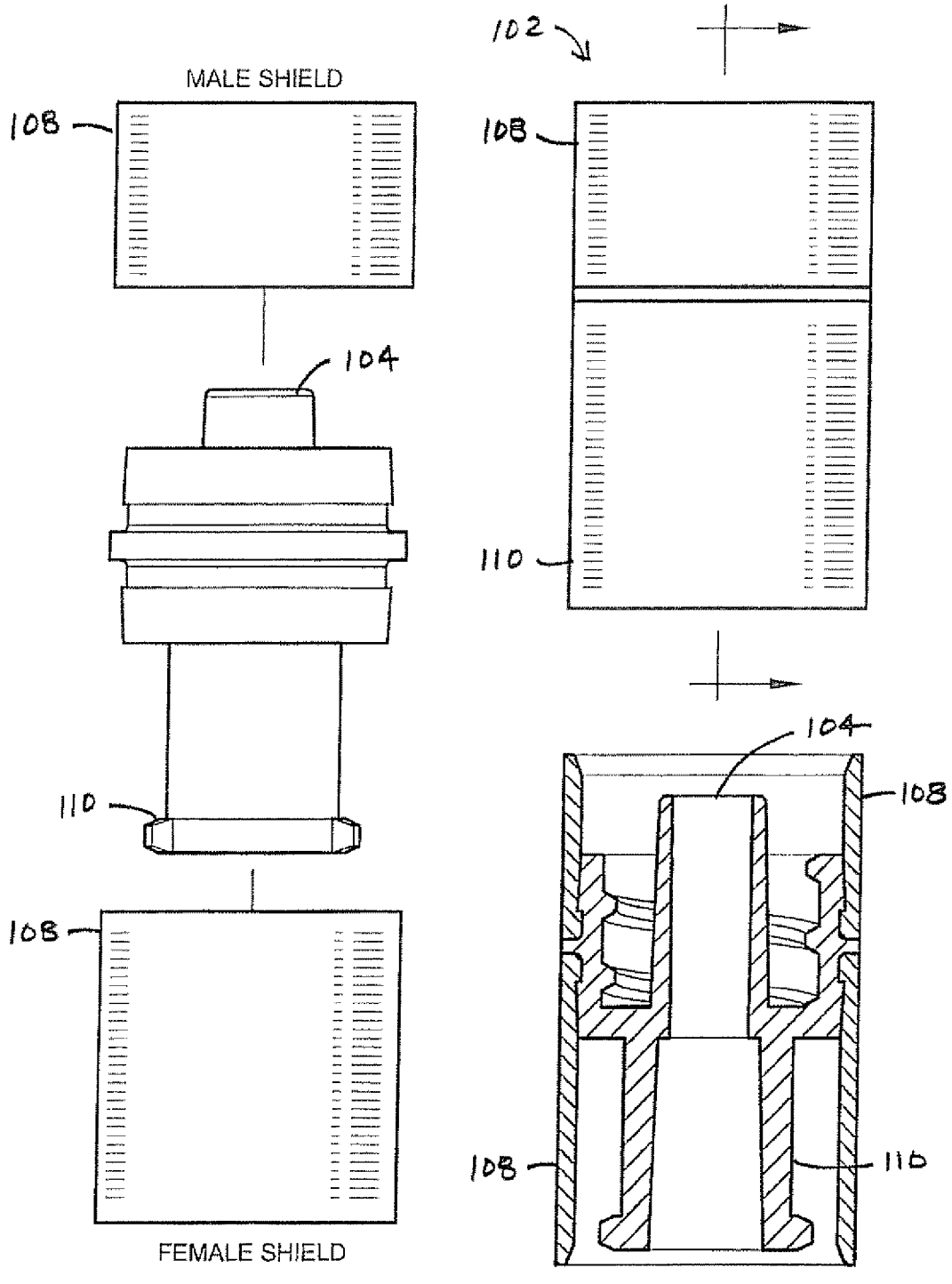
Figure 73:
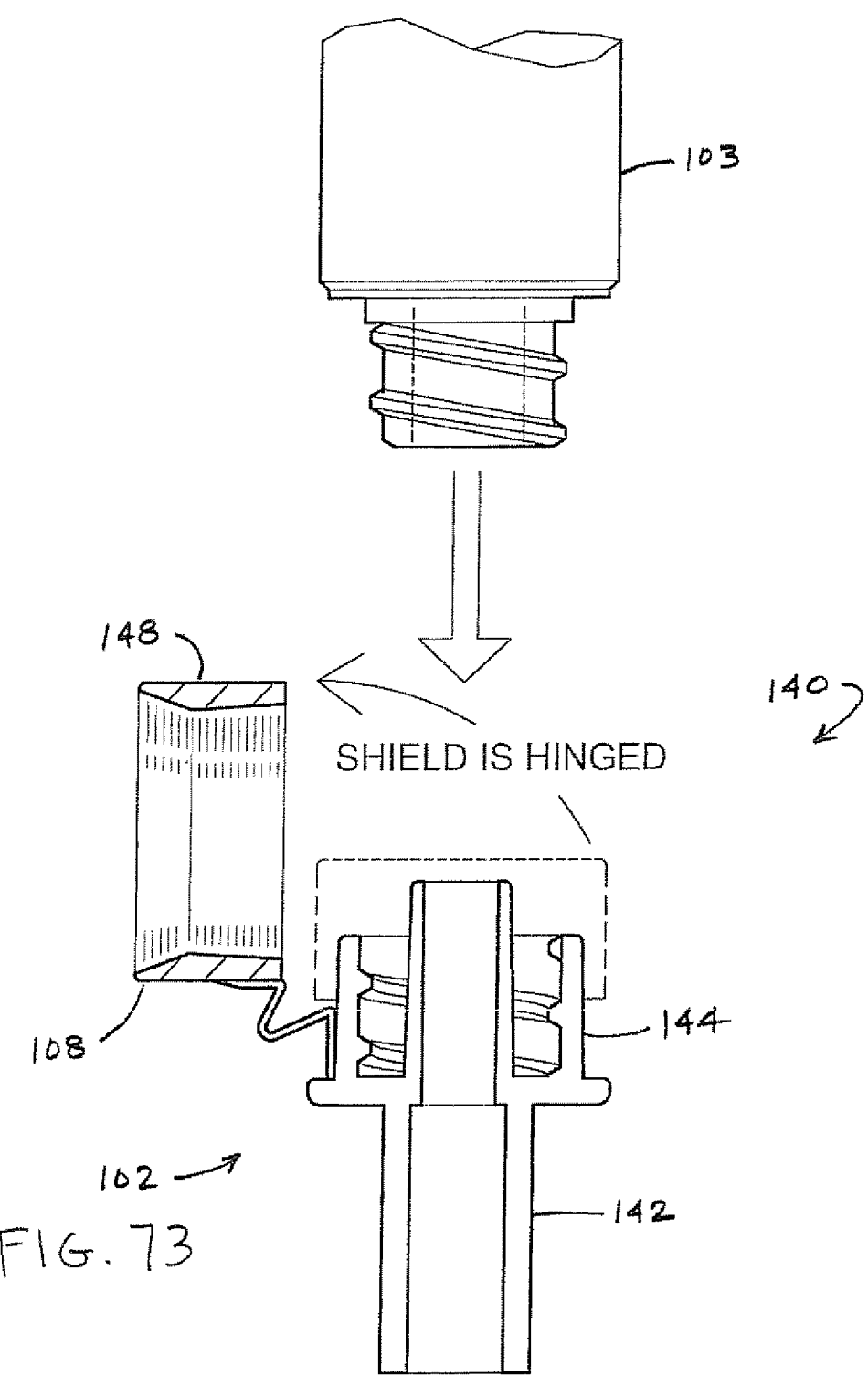
Figure 75:
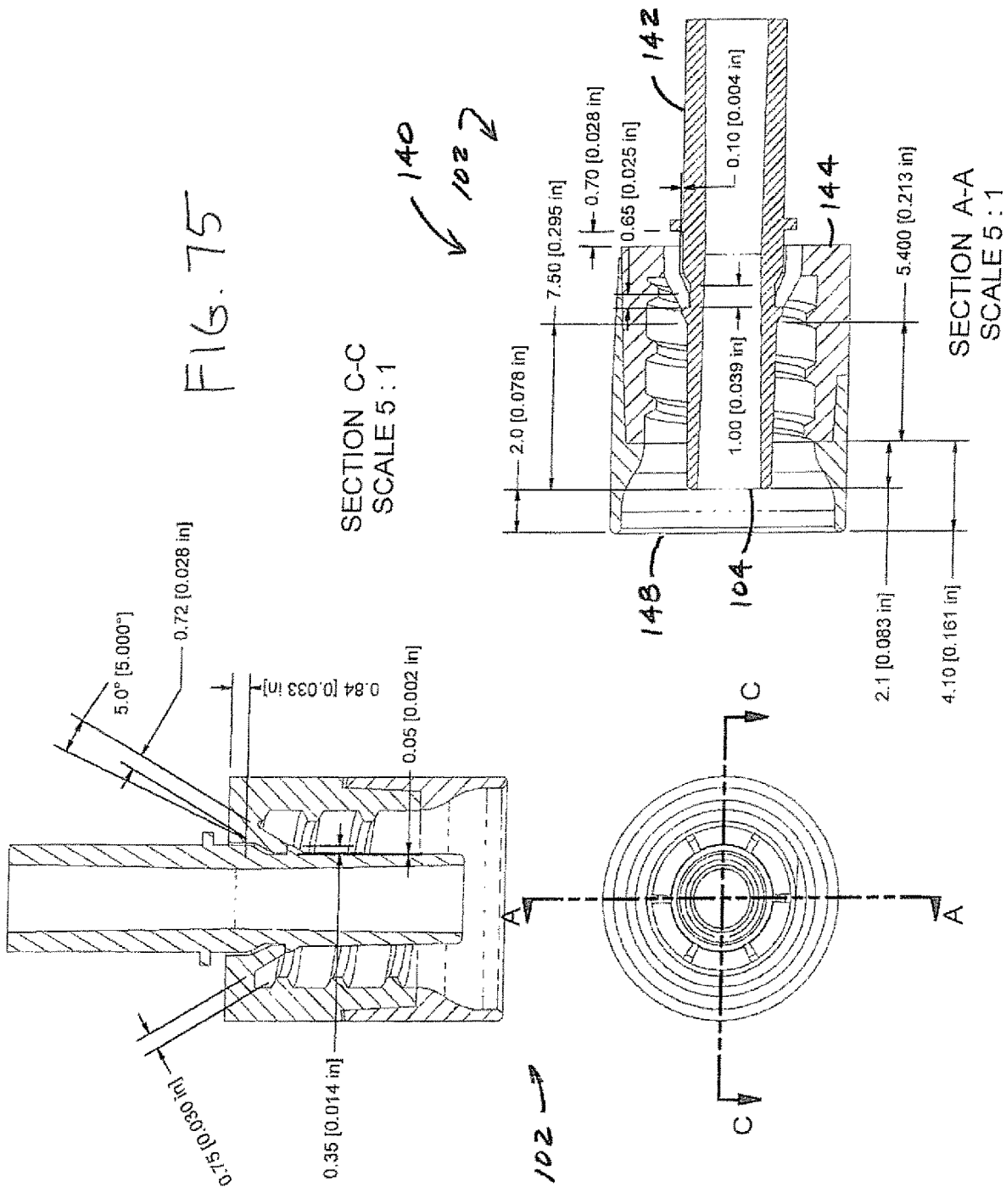
FIGS. 75-97 illustrate side, top, cross-sectional and perspective dimensioned drawings and supporting descriptions of example male Luer-engageable reduced-touch contamination devices, according to contemplated embodiments of the present invention.
Figure 76:
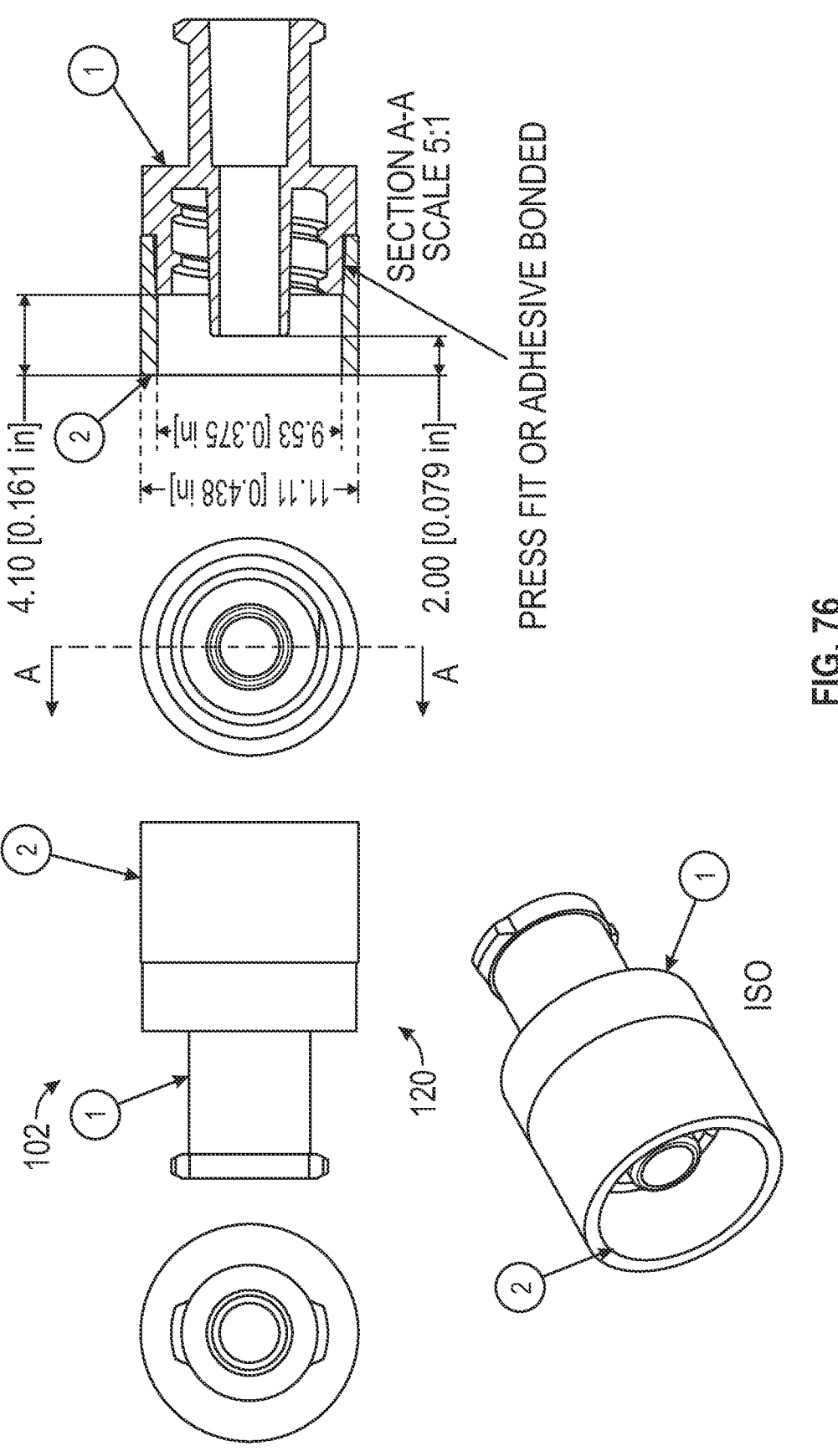
Figure 77:
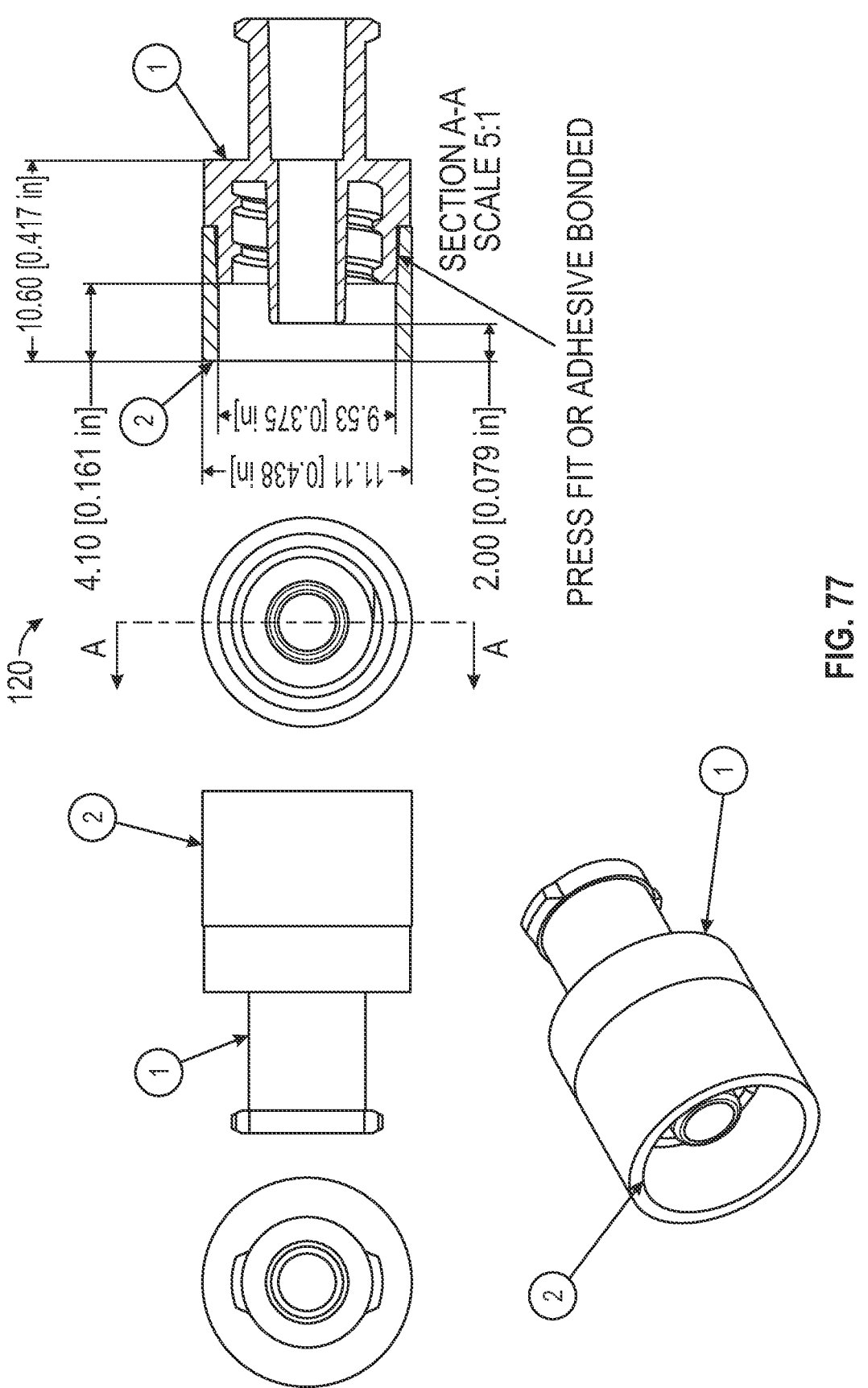
Figure 78:
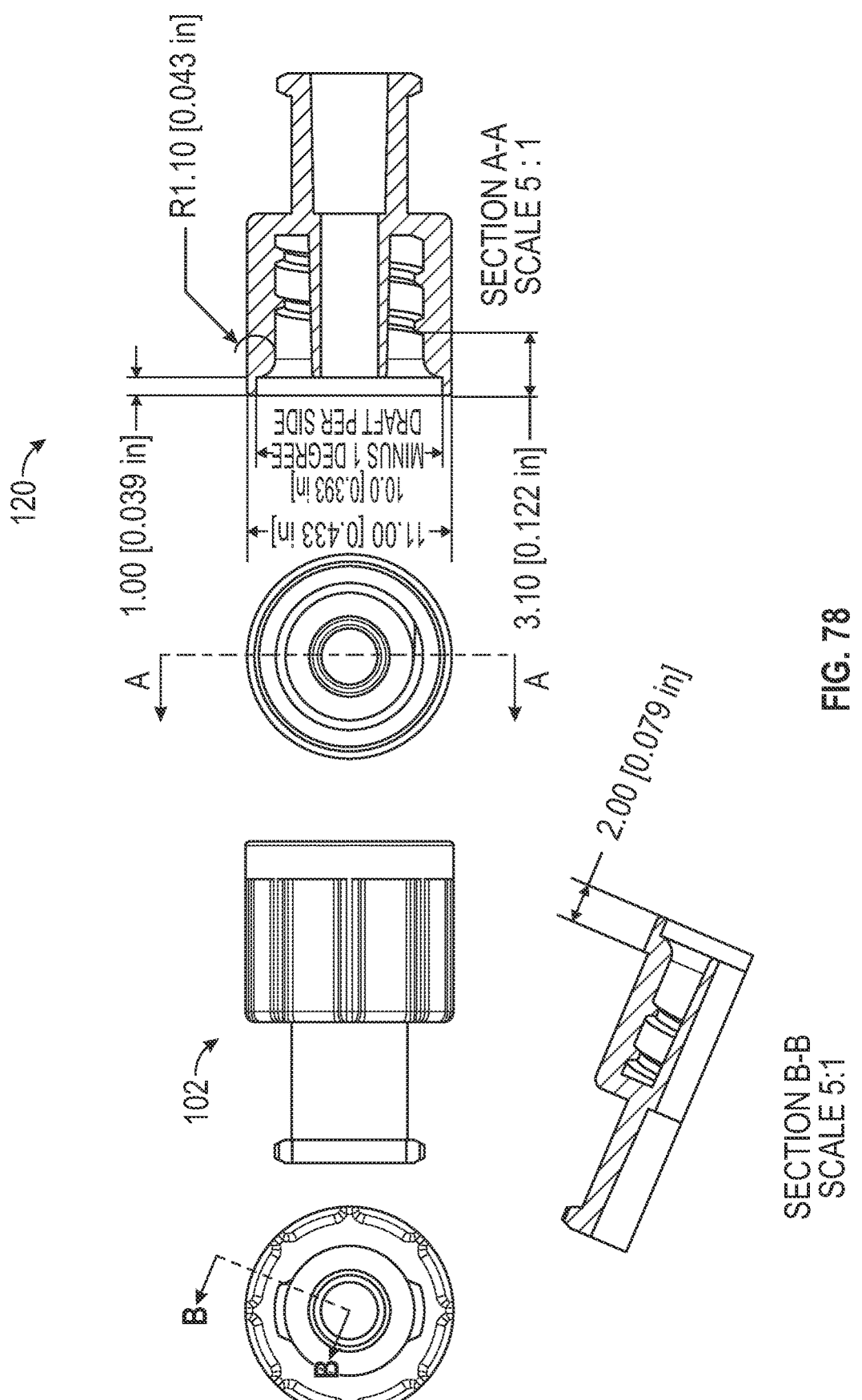
Figure 79:
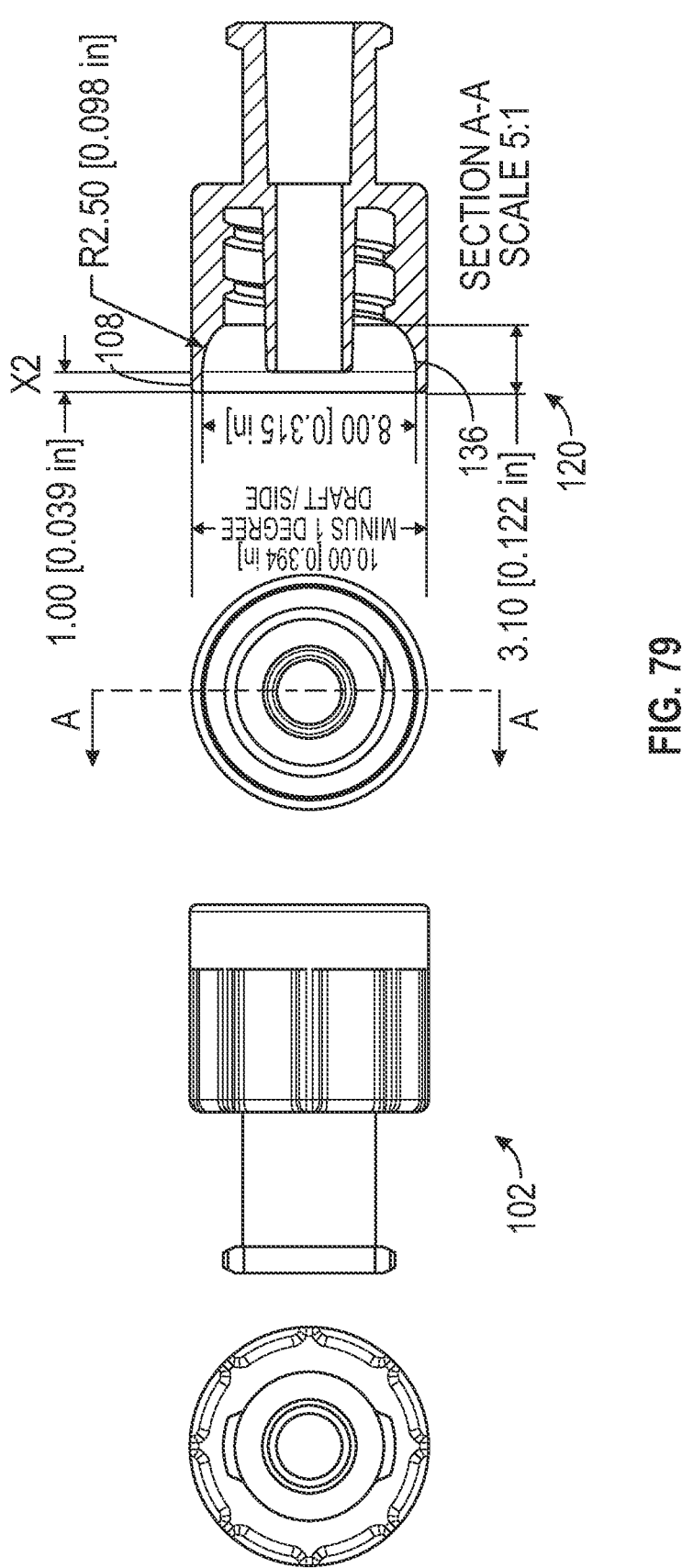
Figure 80:
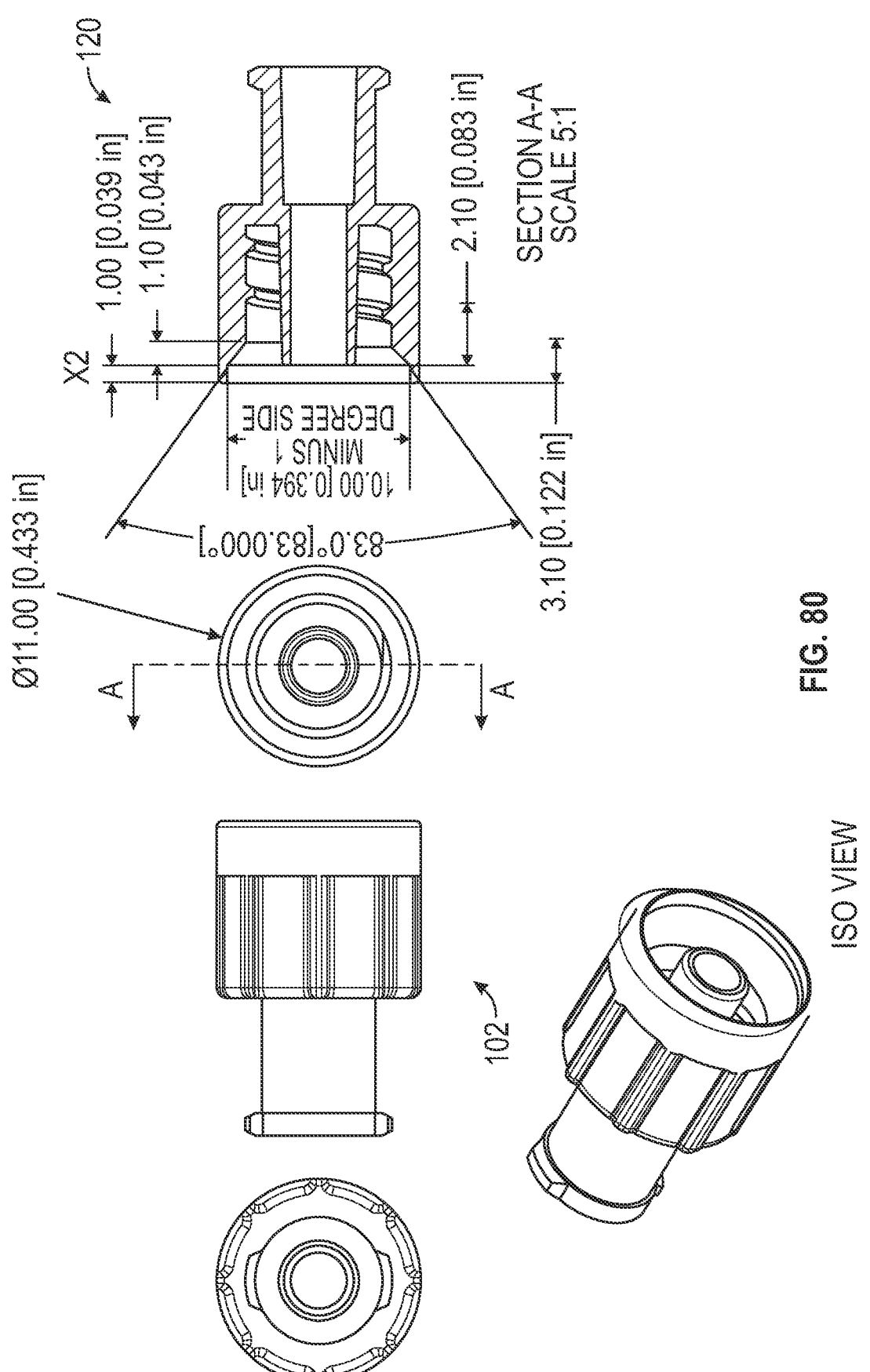
Figure 81:
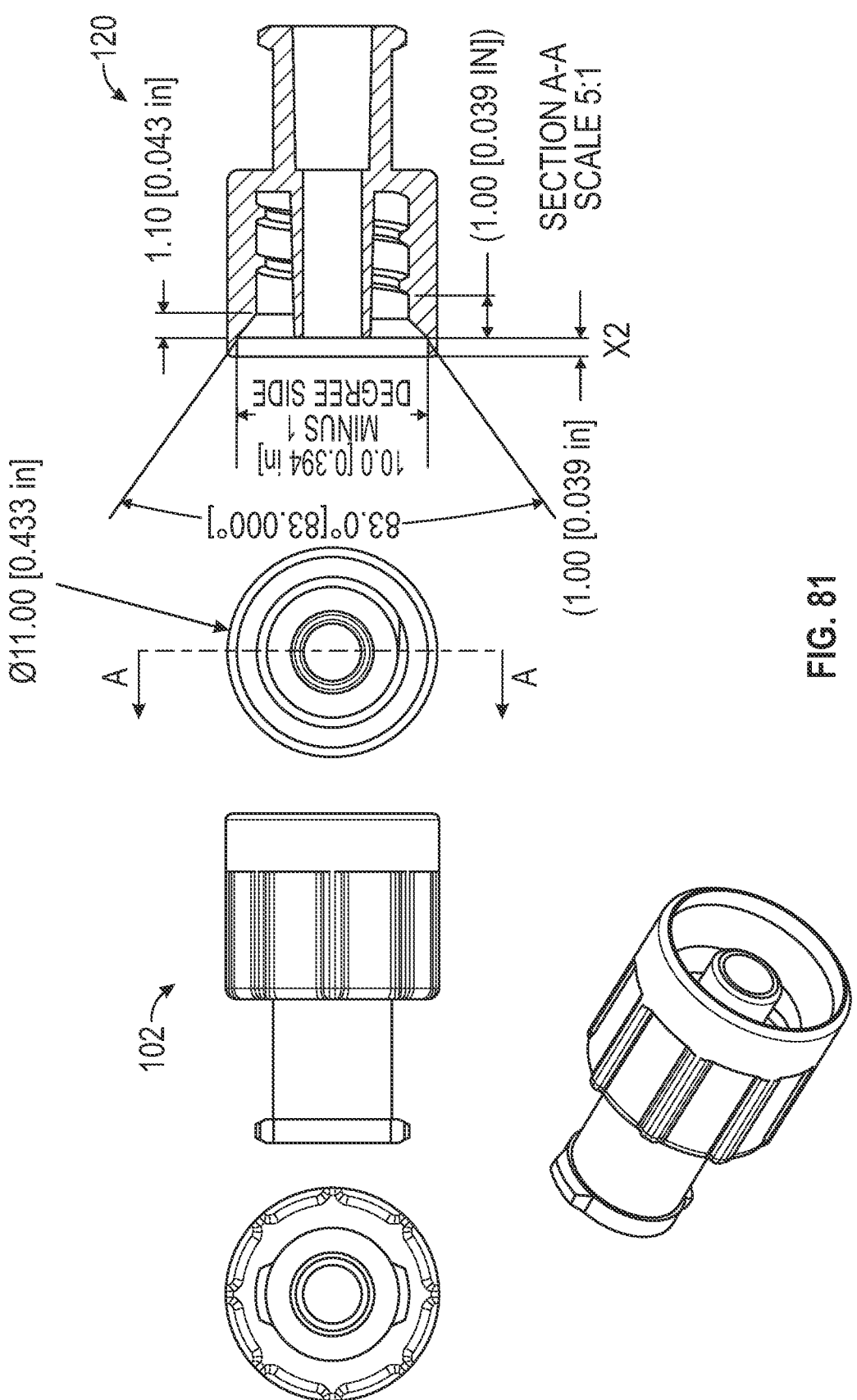
Figure 82:
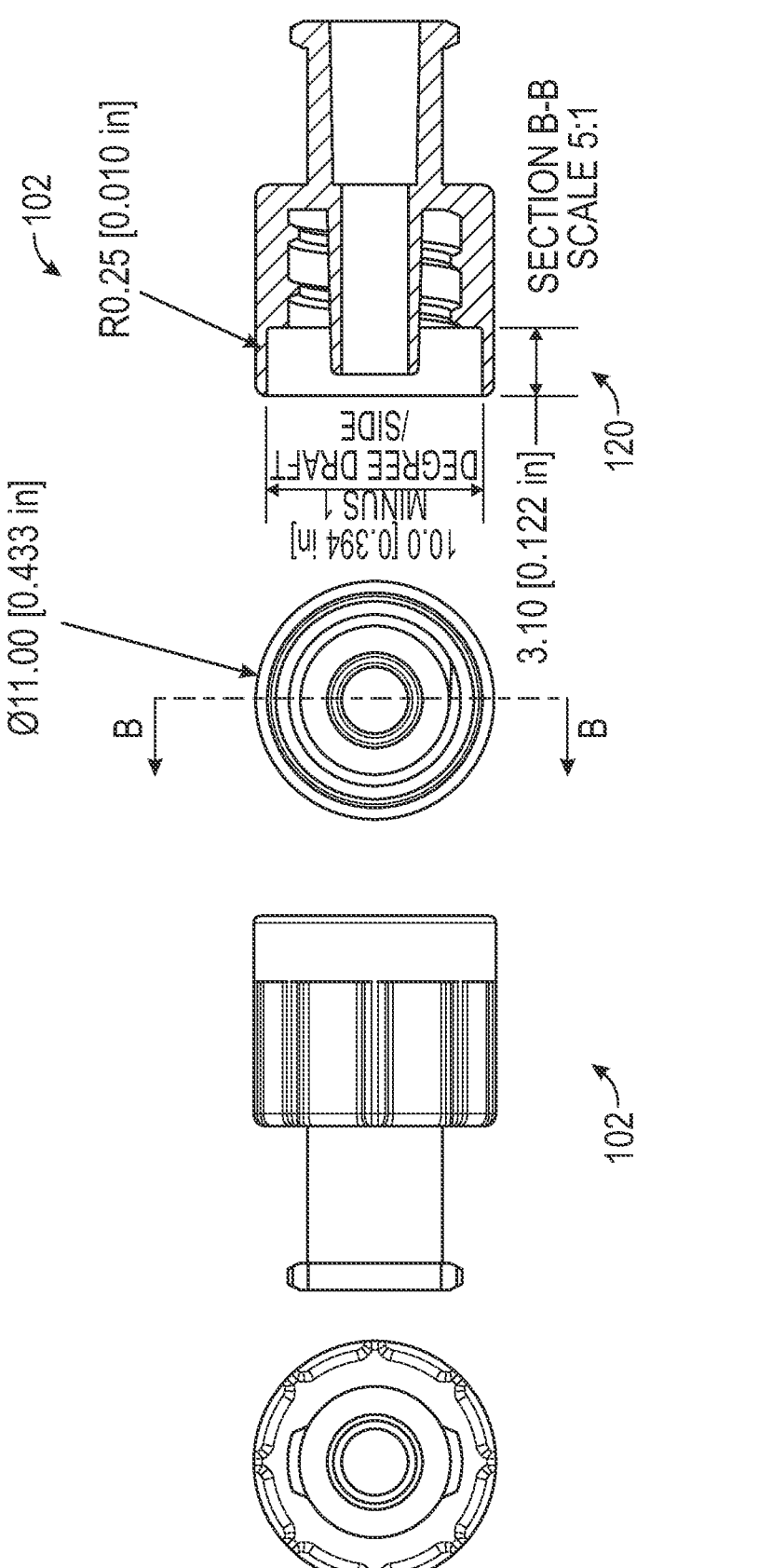
Figure 83:
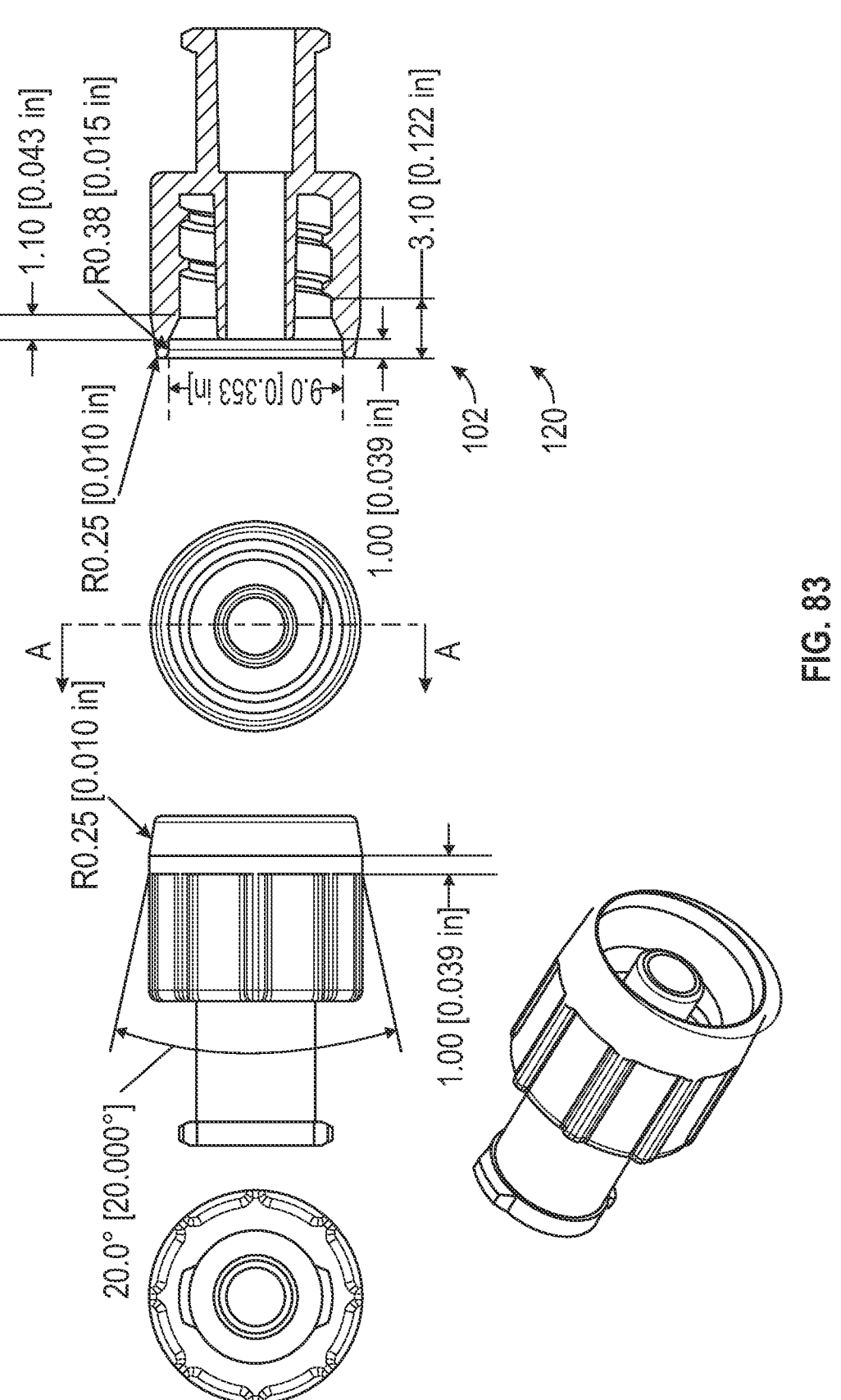
Figure 84:
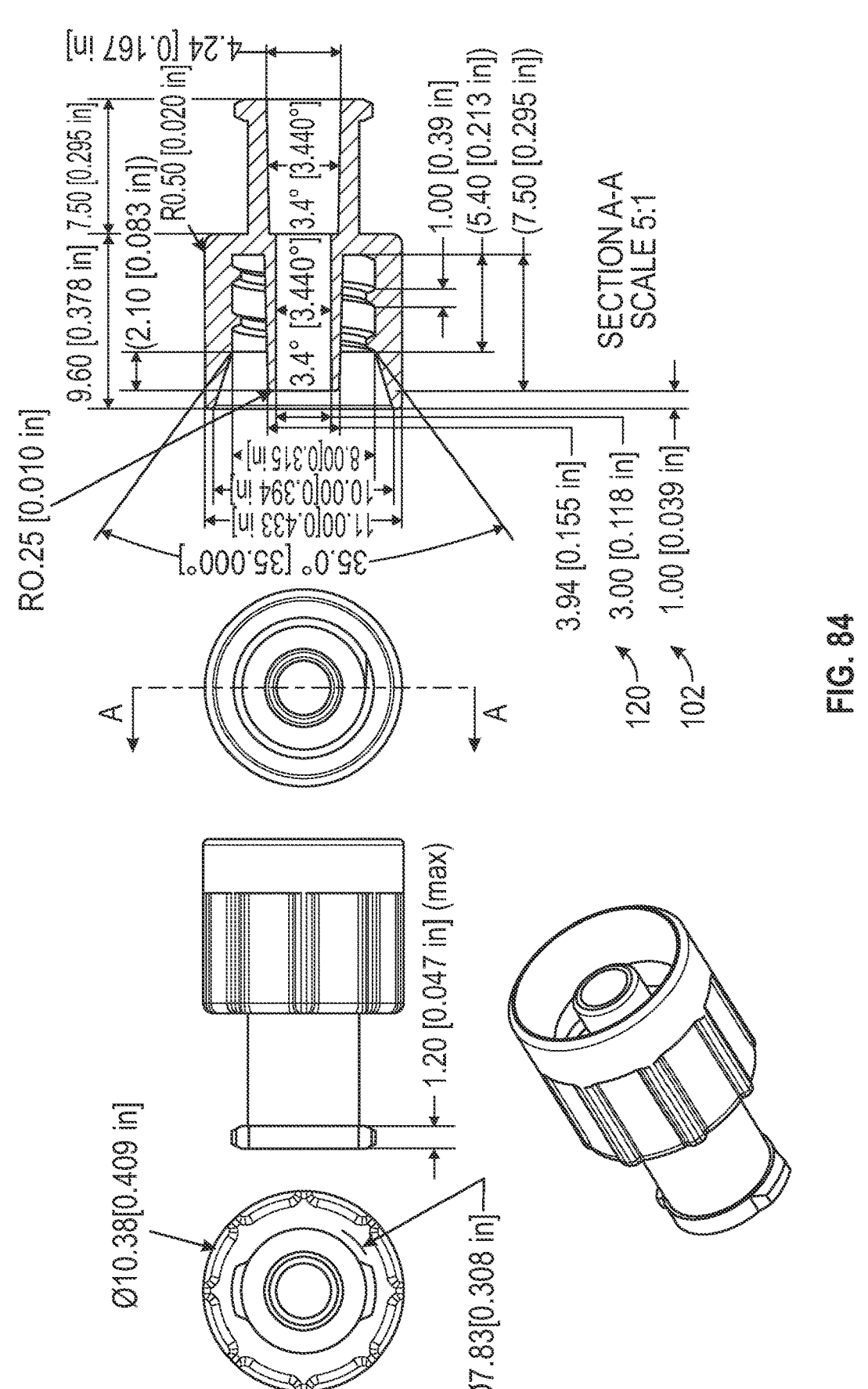
Figure 85:
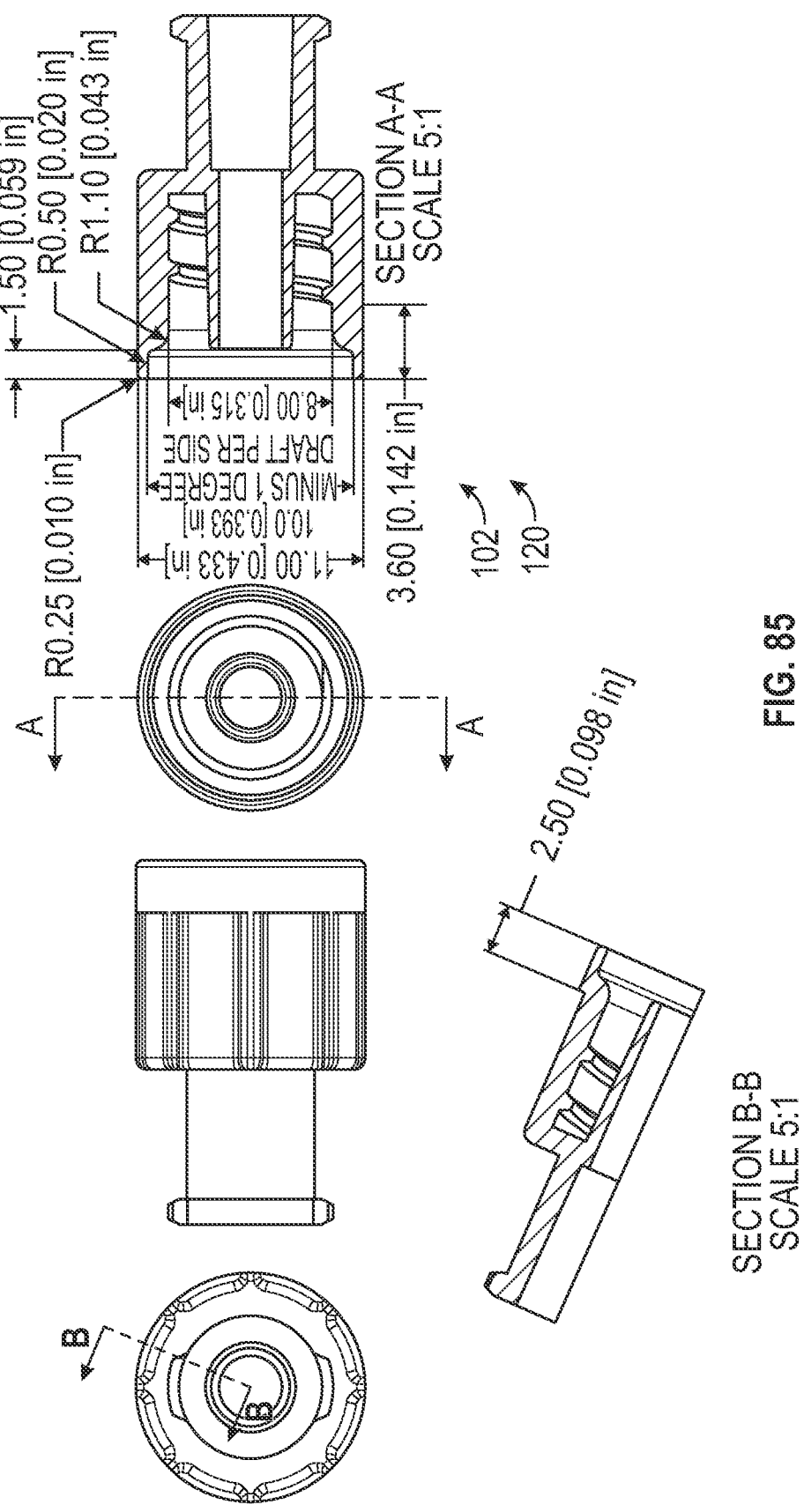
Figure 86:
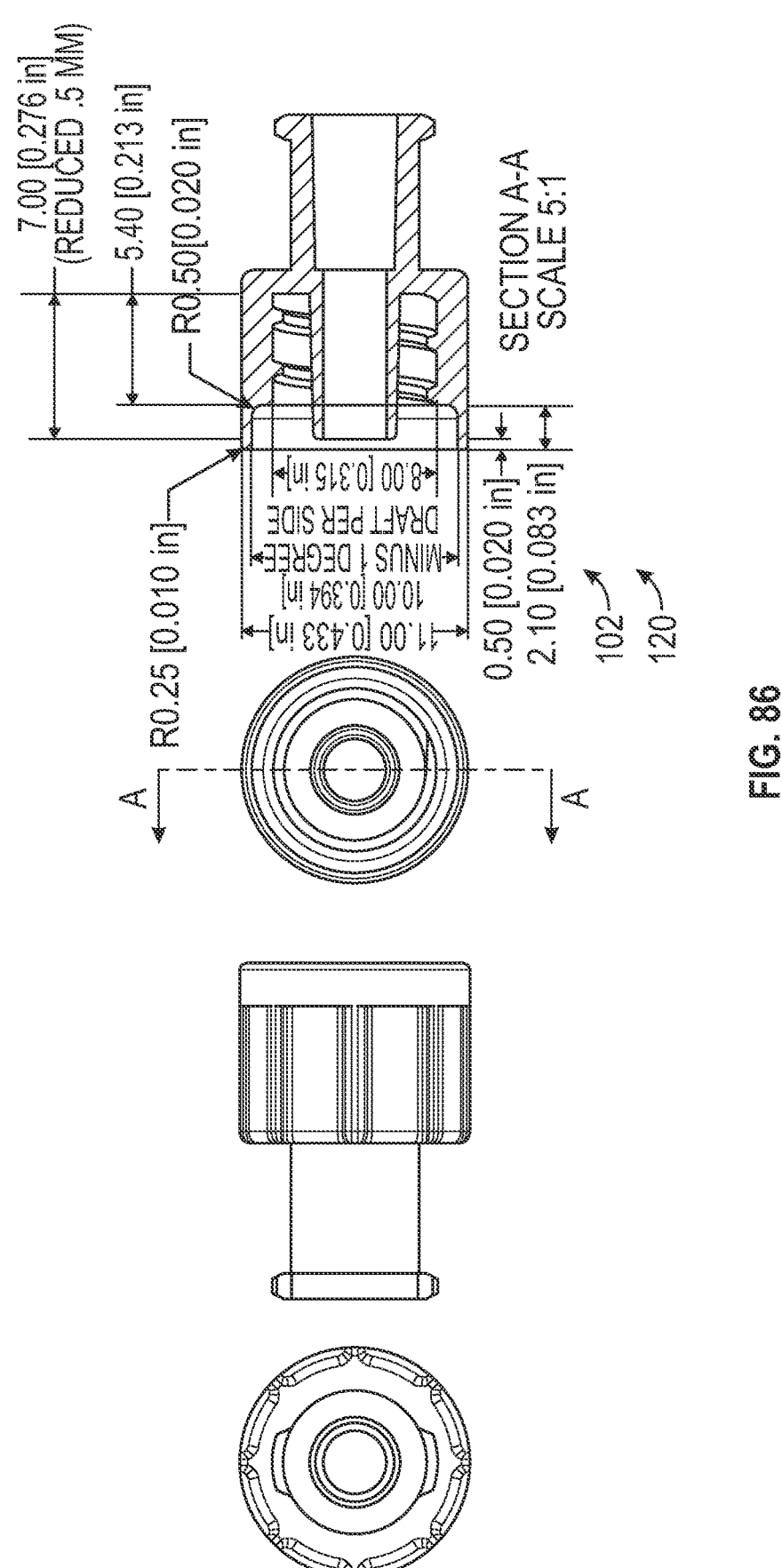
Figure 87:
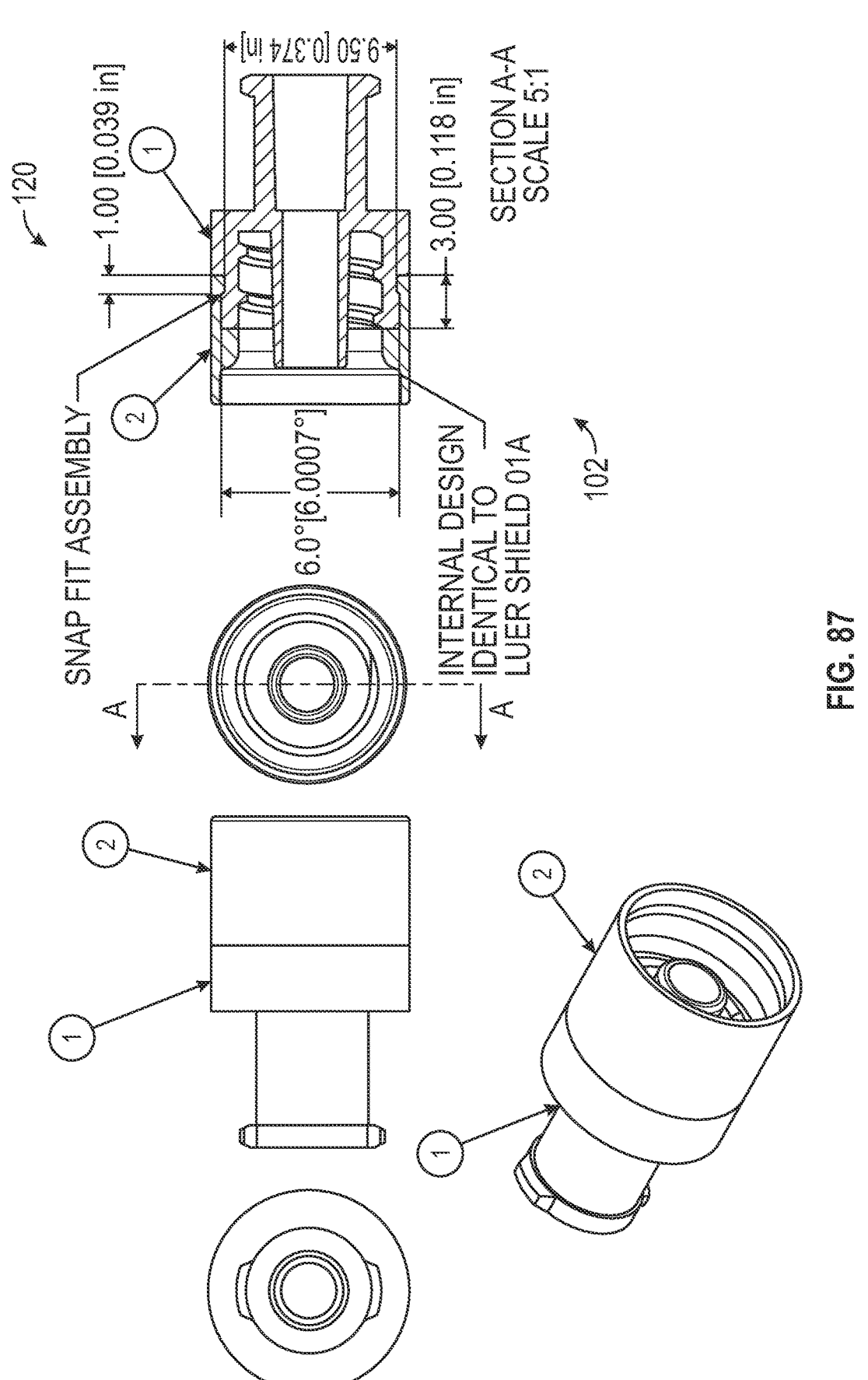
Figure 88:
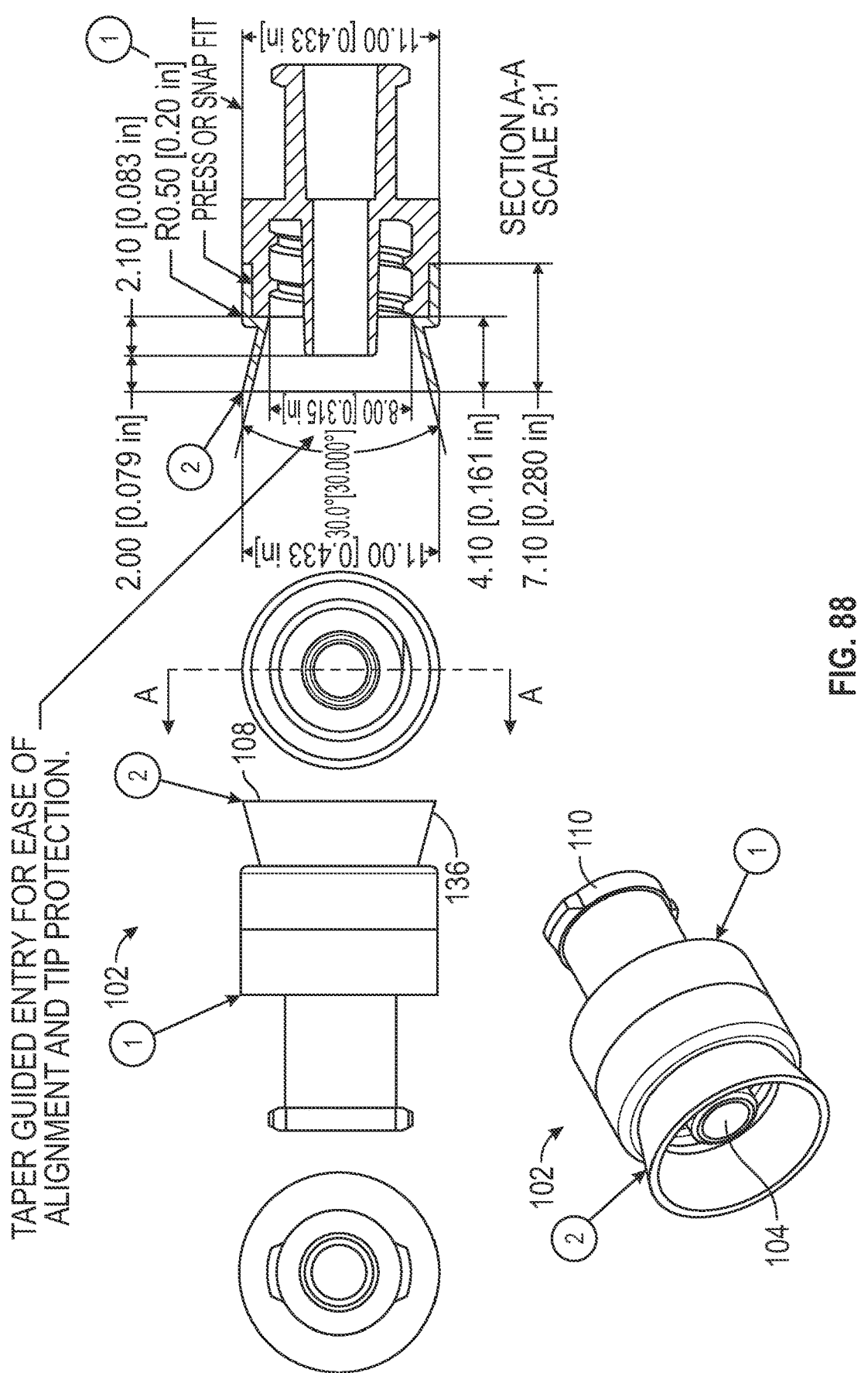
Figure 89:
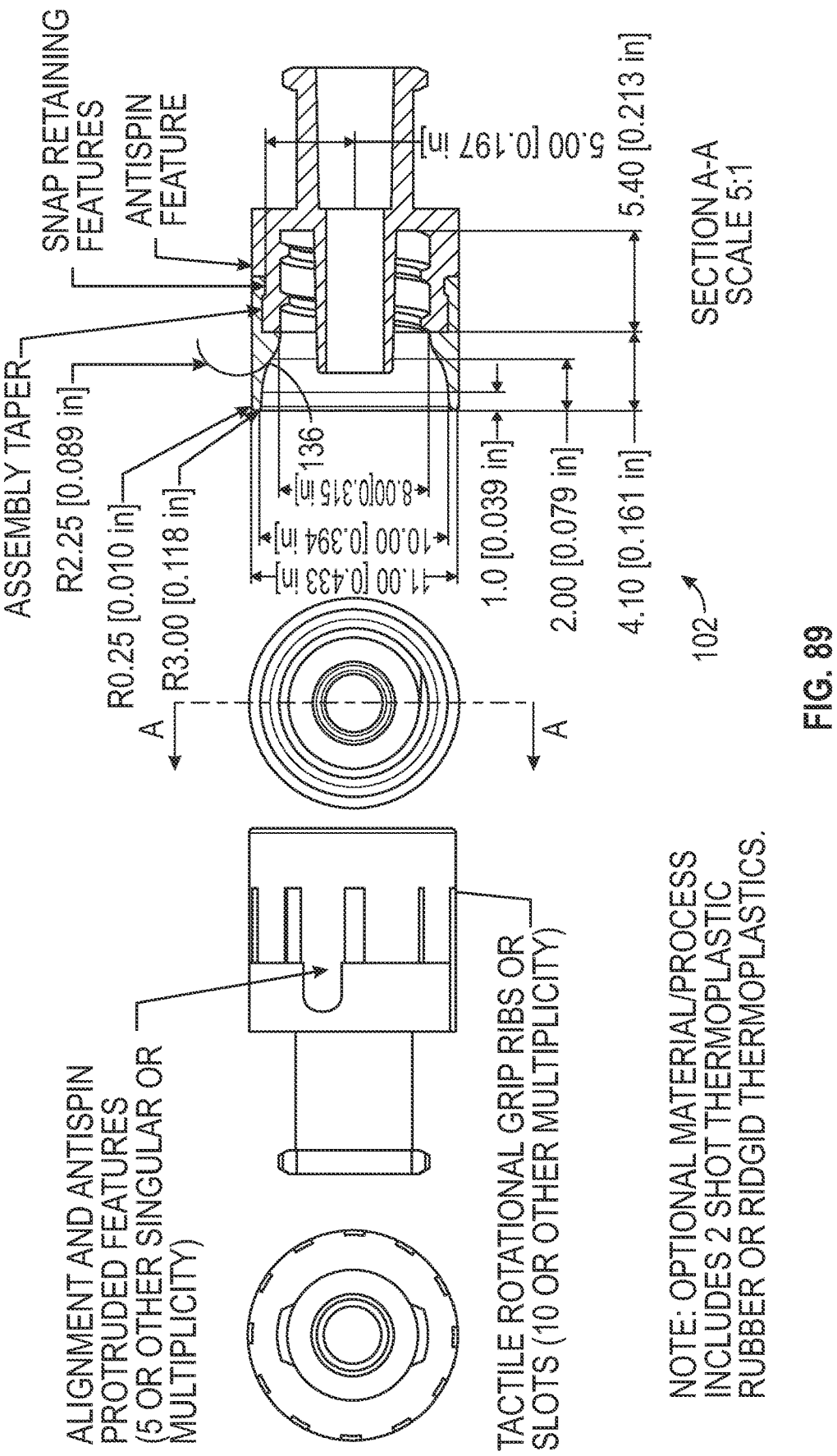
Figure 90:
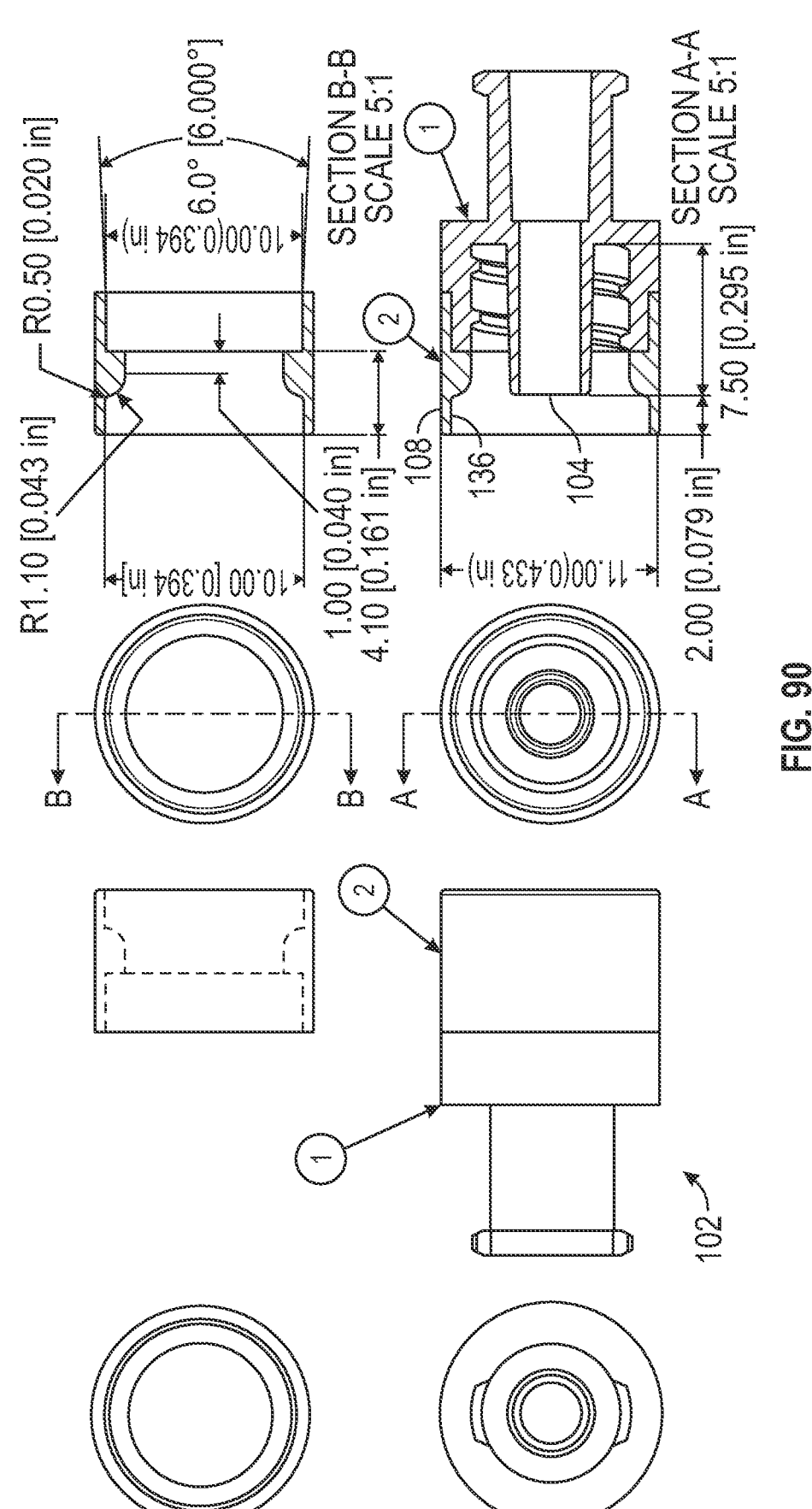
Figure 91:
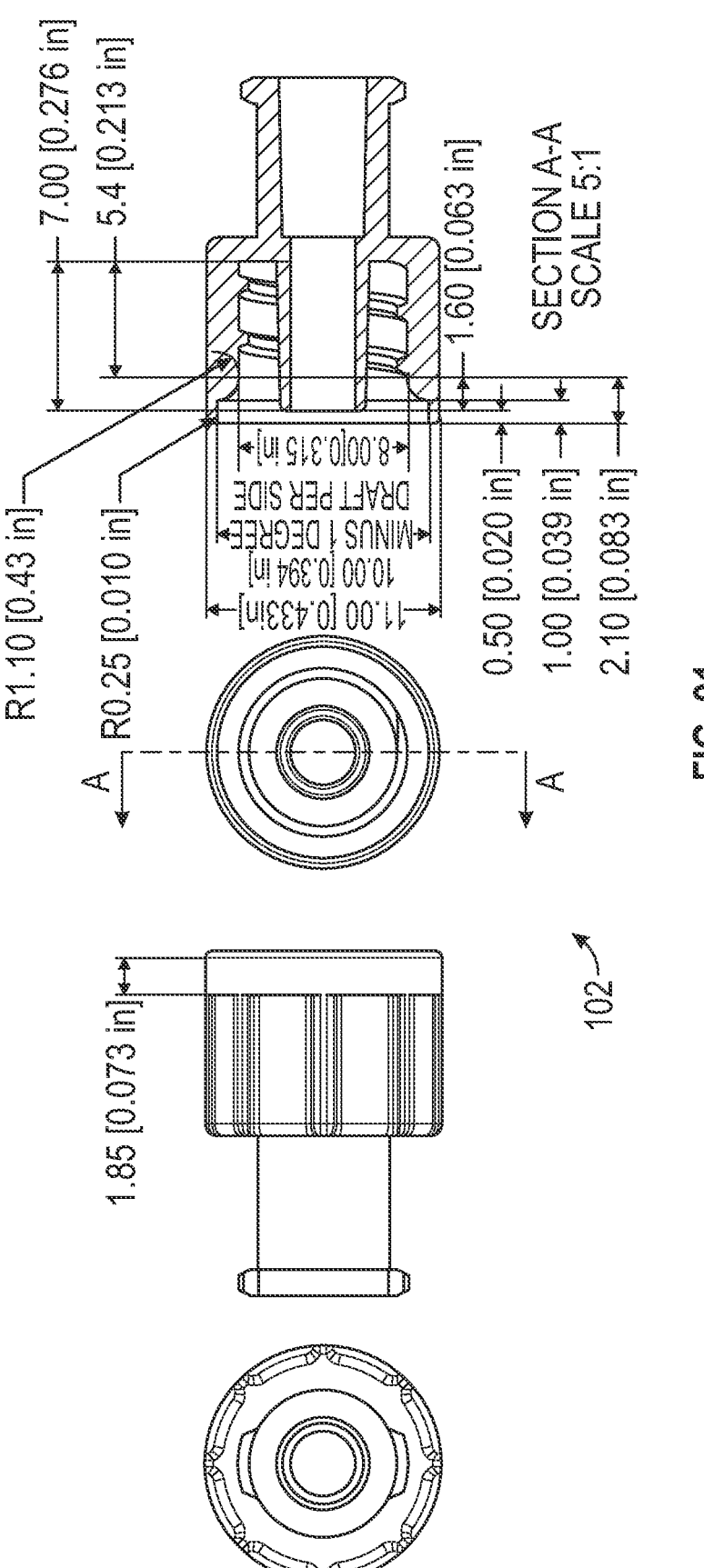
Figure 92:
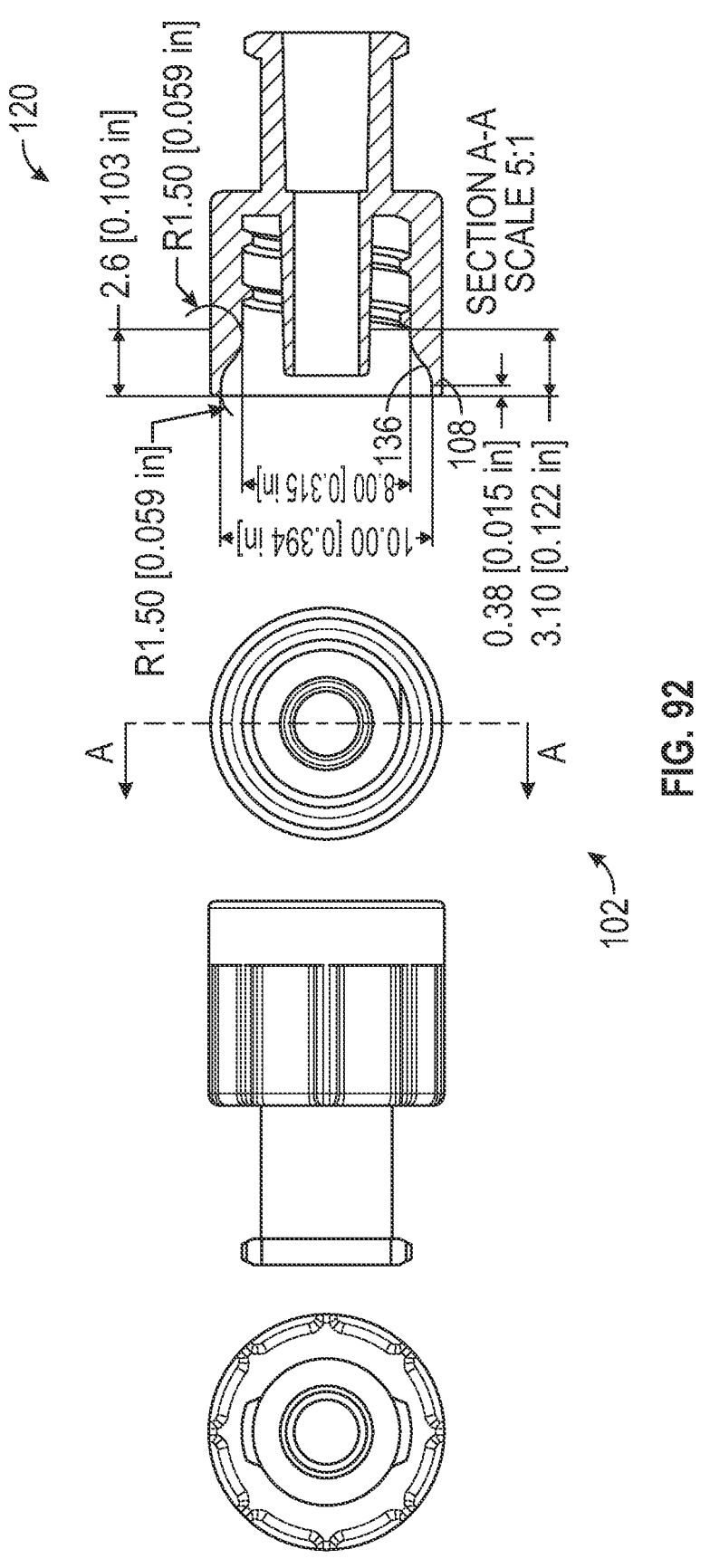
Figure 93:
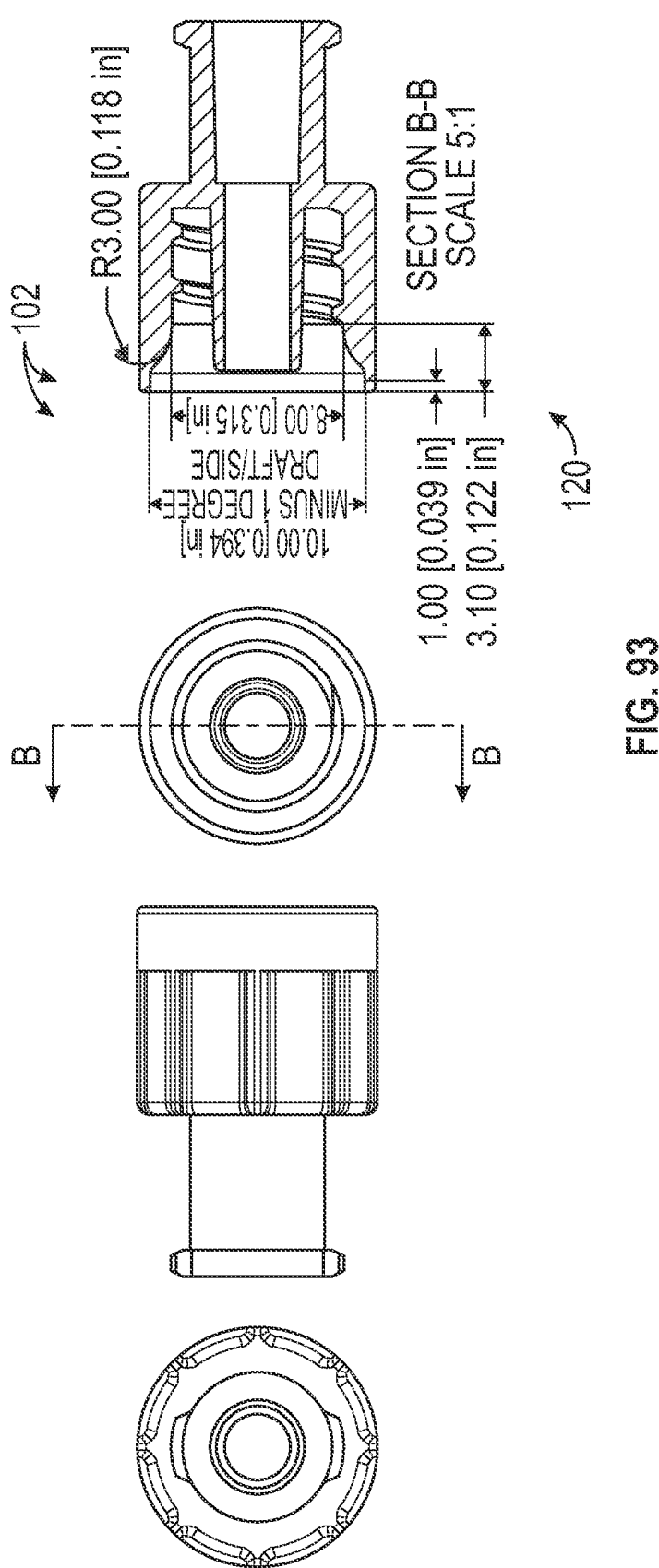
Figure 94:
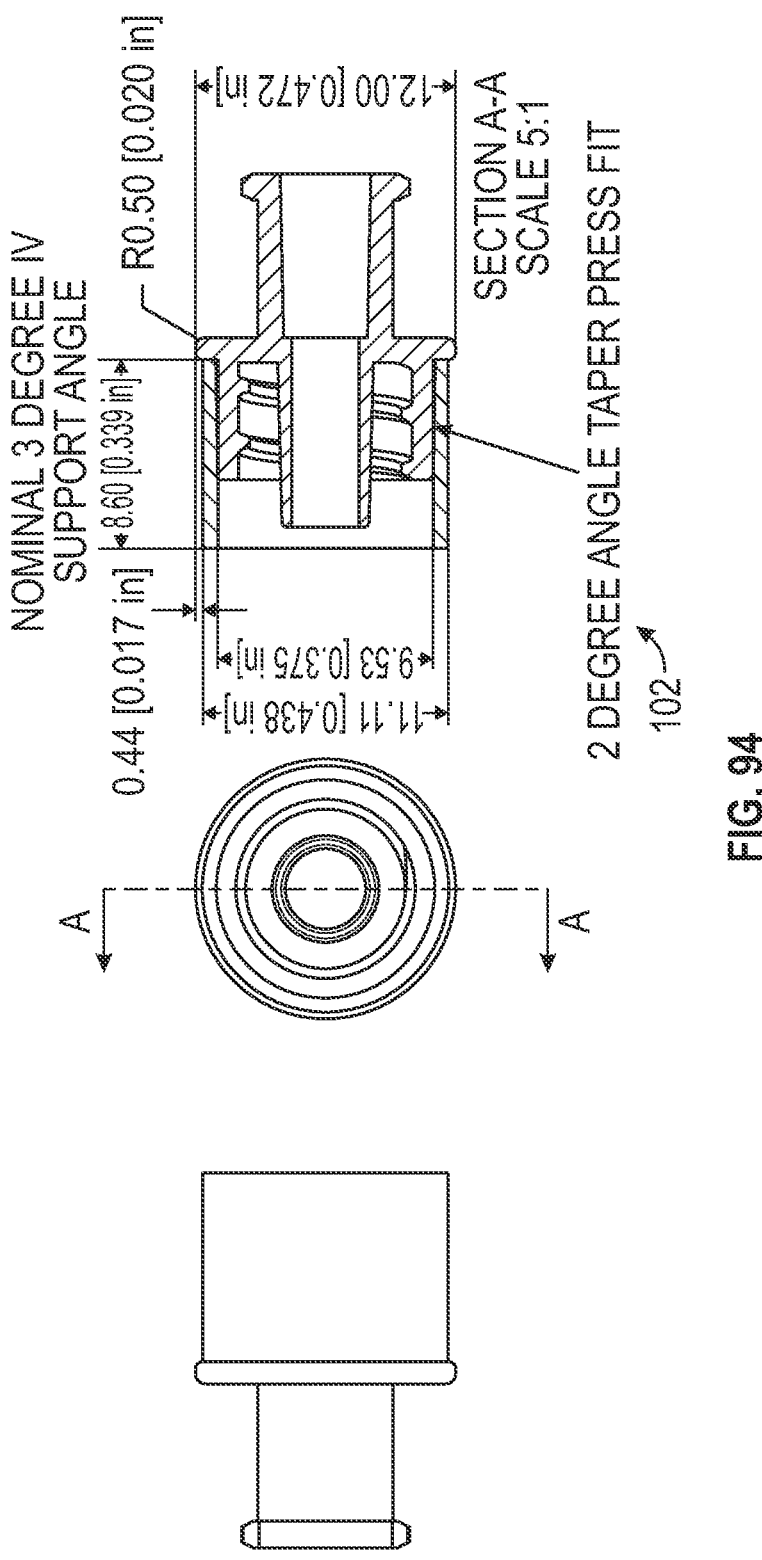
Figure 95:
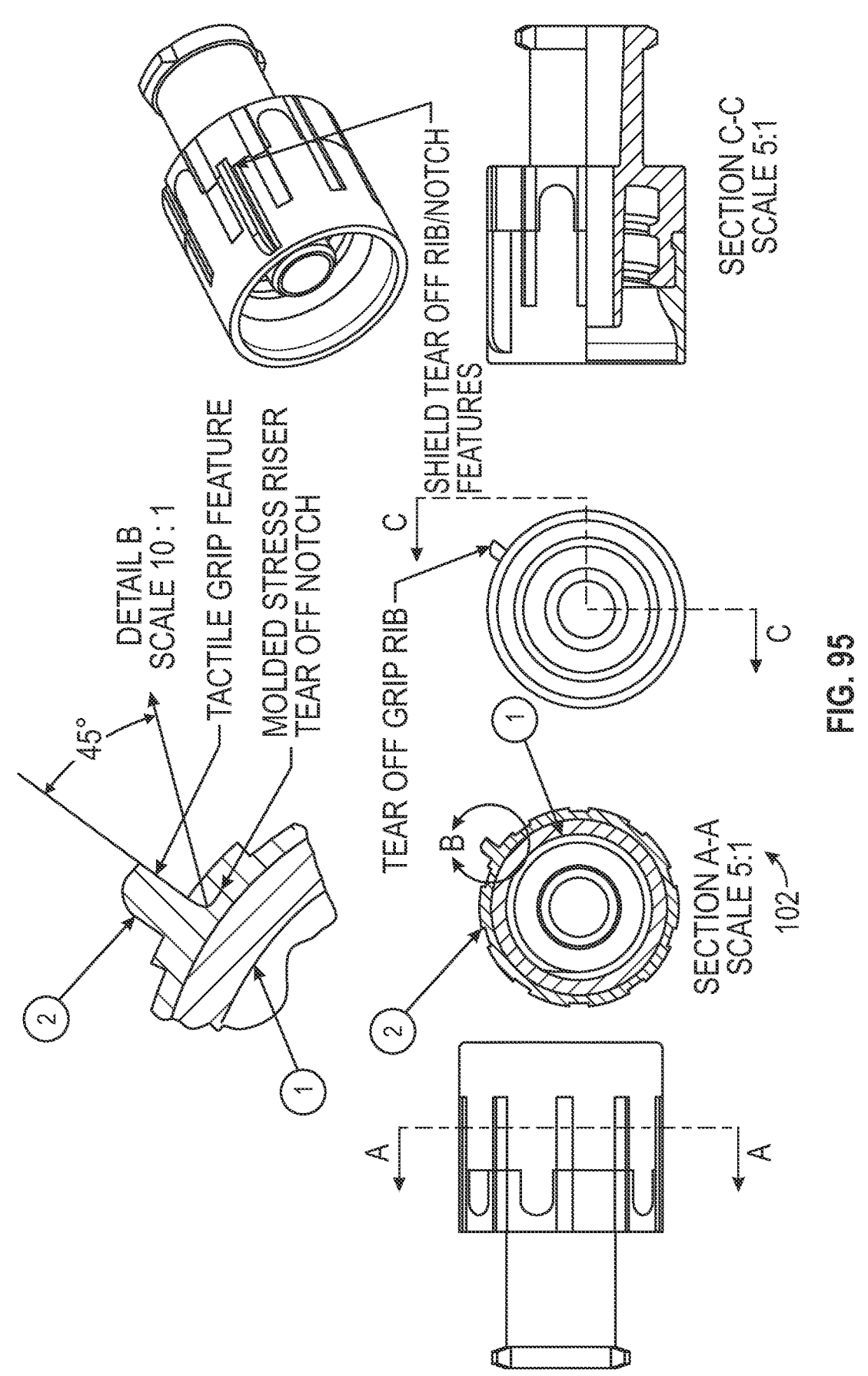
Figure 96:
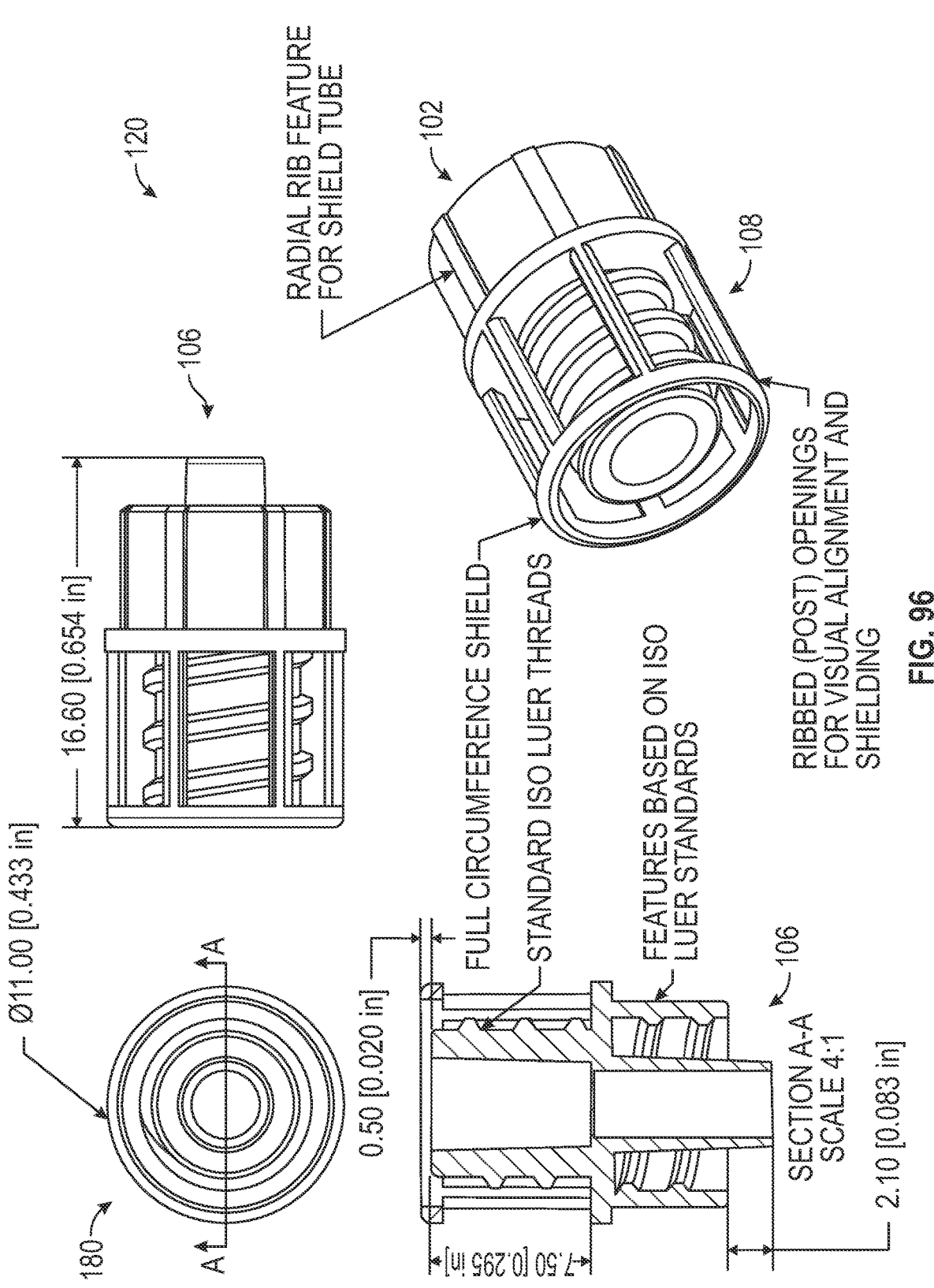
Figure 97:
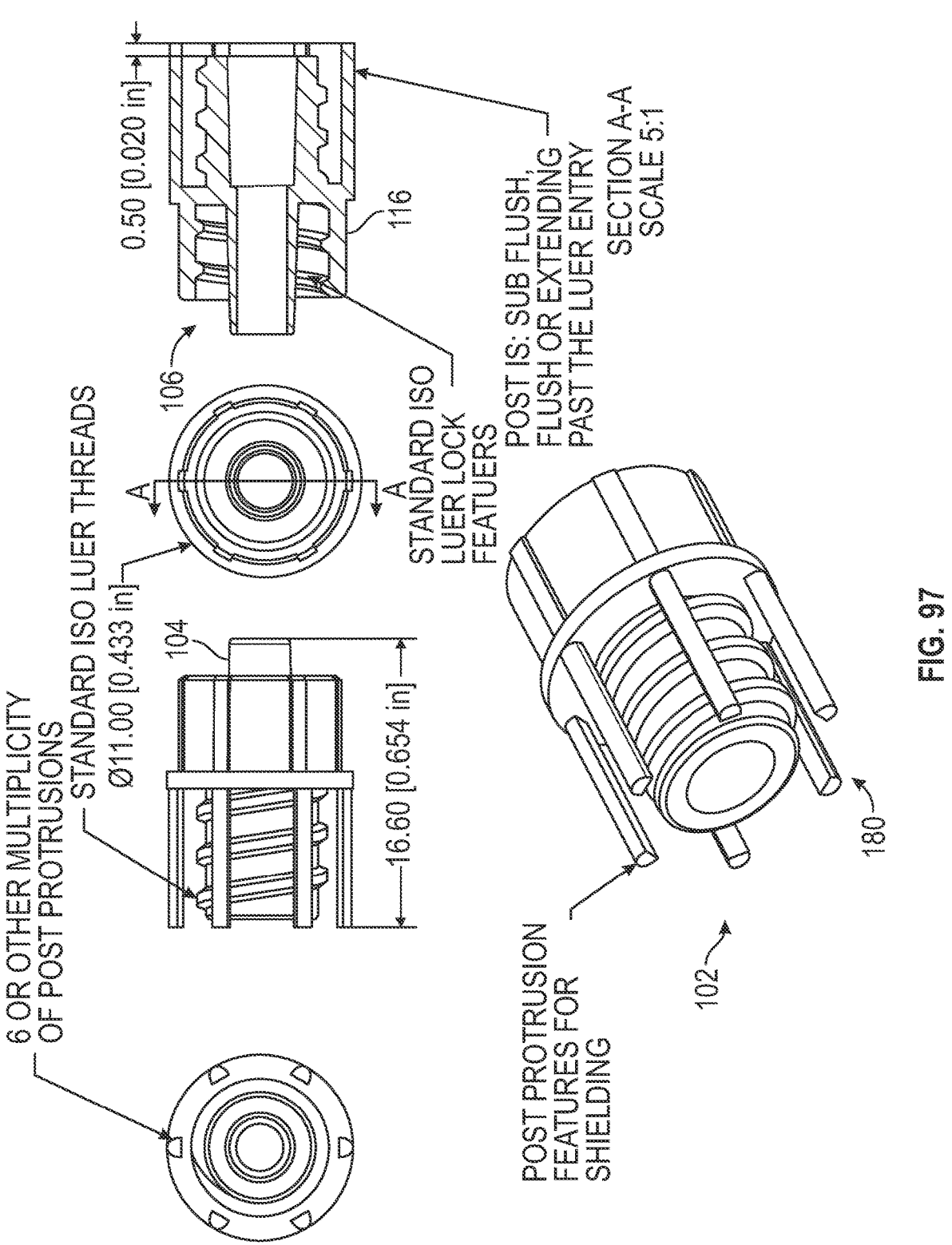
Figure 98:
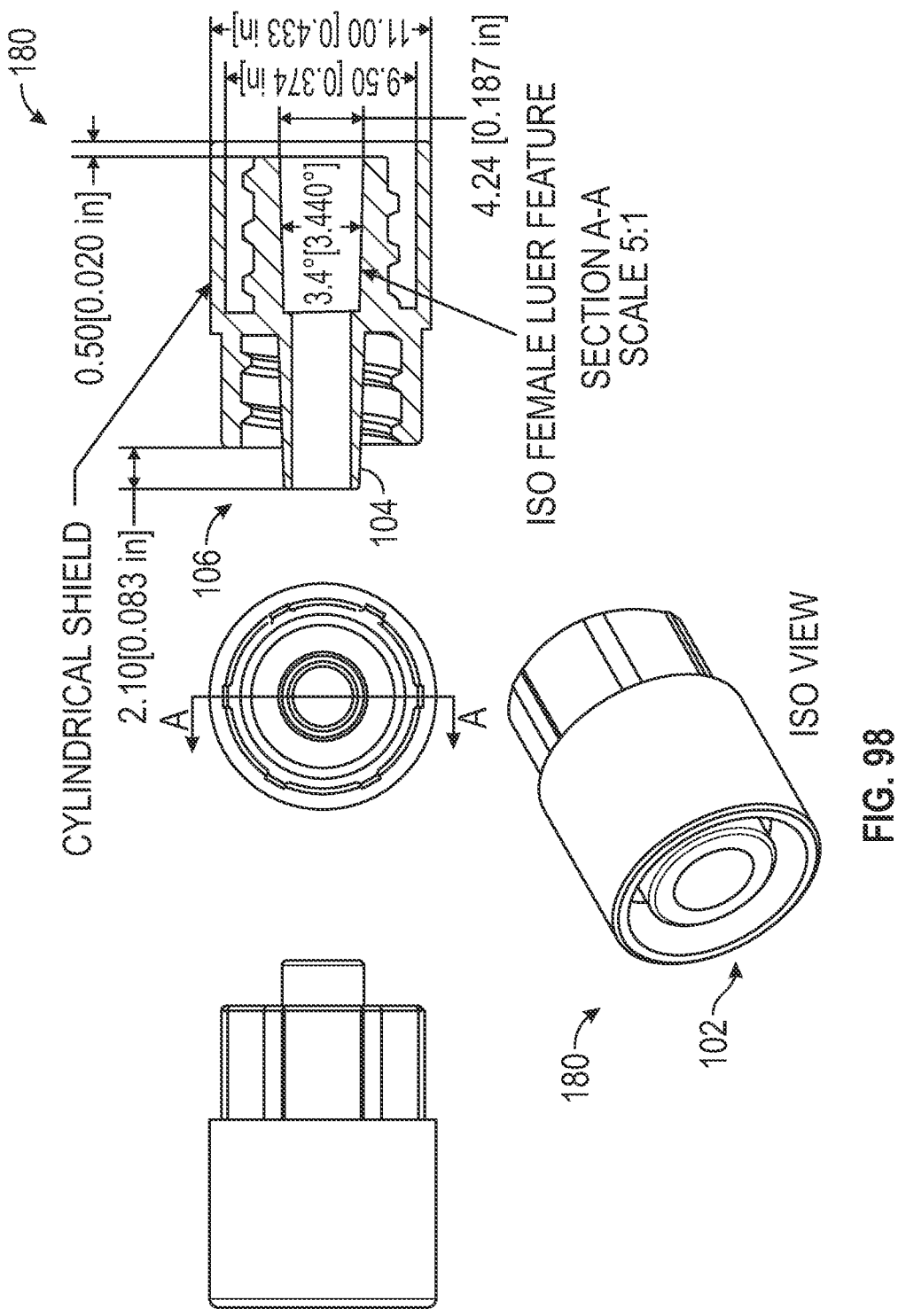
FIGS. 98-104 illustrate side, top, cross-sectional and perspective dimensioned drawings and supporting descriptions of example shielded female Luer-engageable reduced touch contamination devices, according to contemplated embodiments of the present invention.
Figure 99:
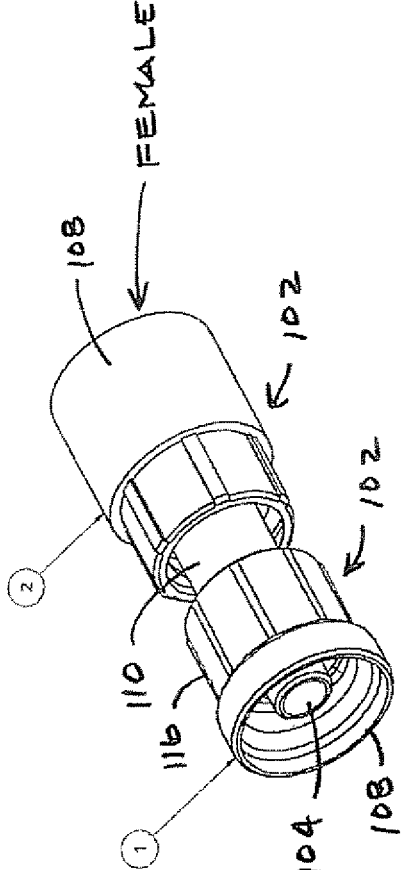
Figure 100:
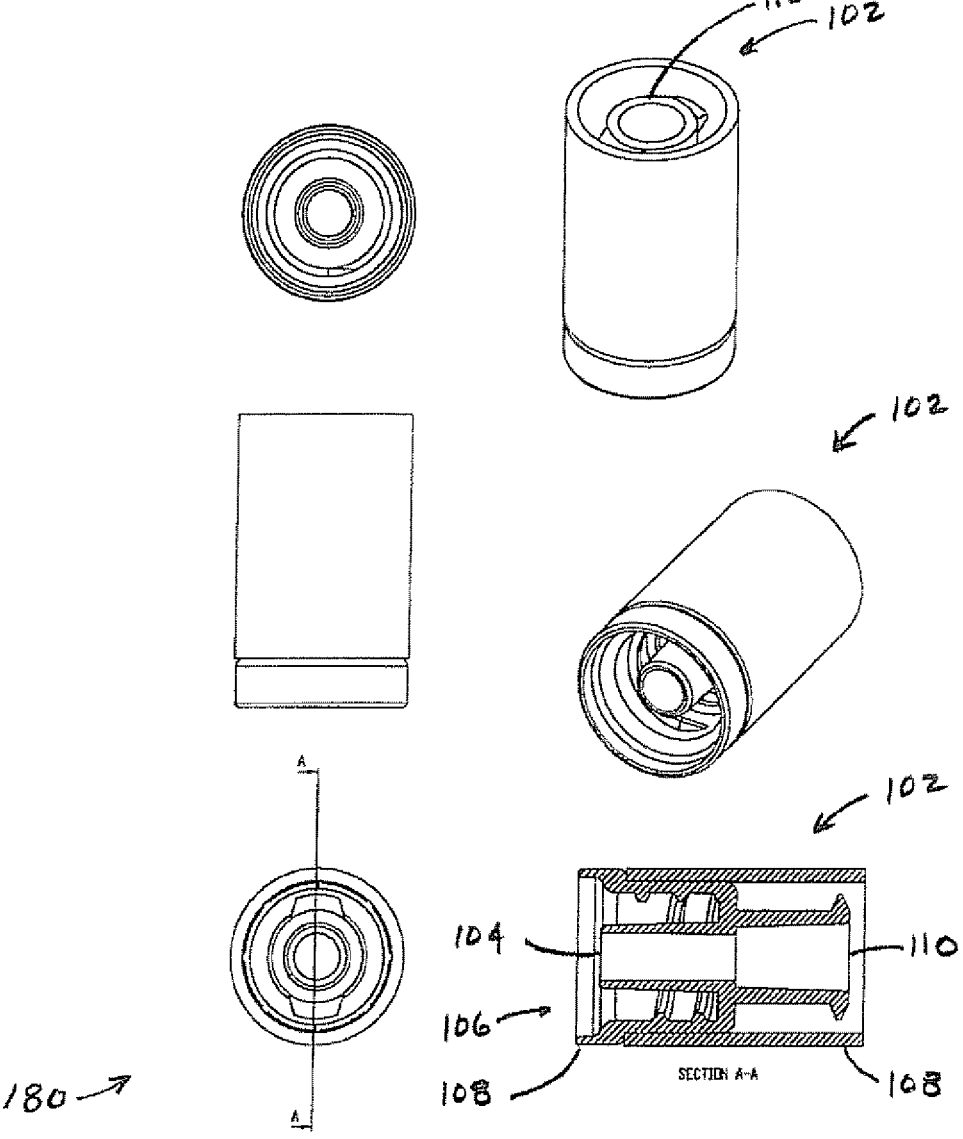
Figure 101:
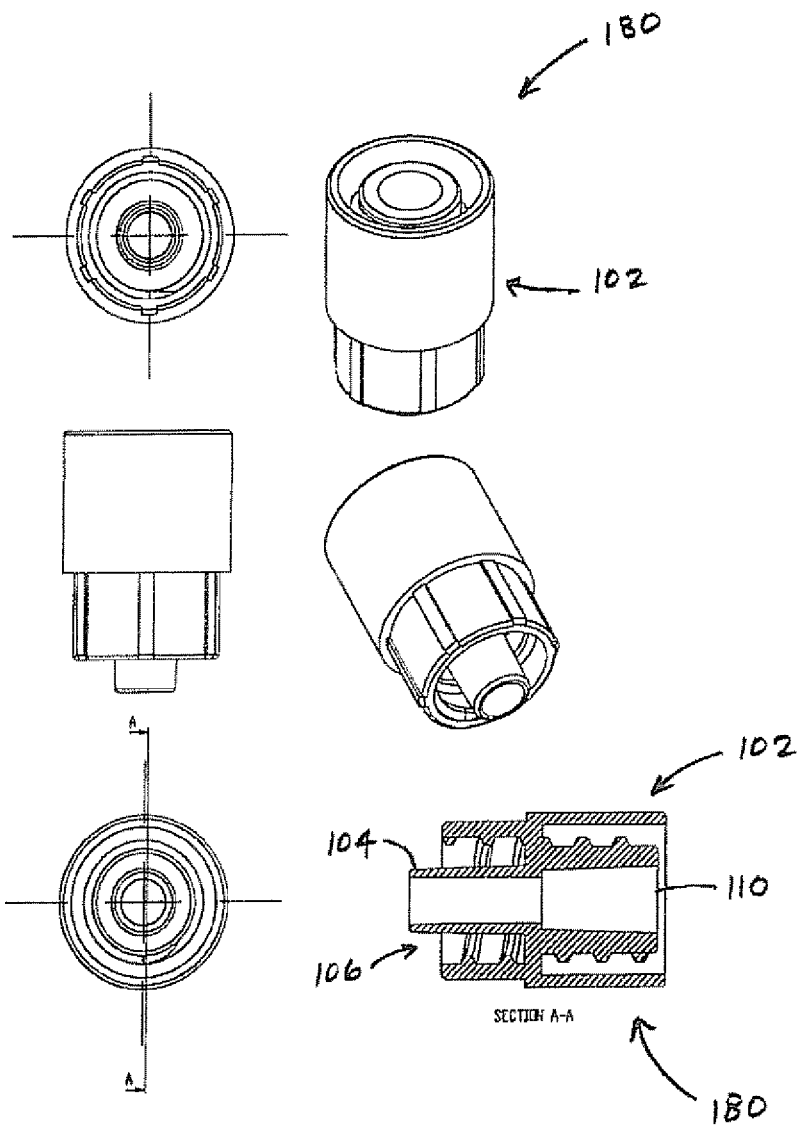
Figure 102:
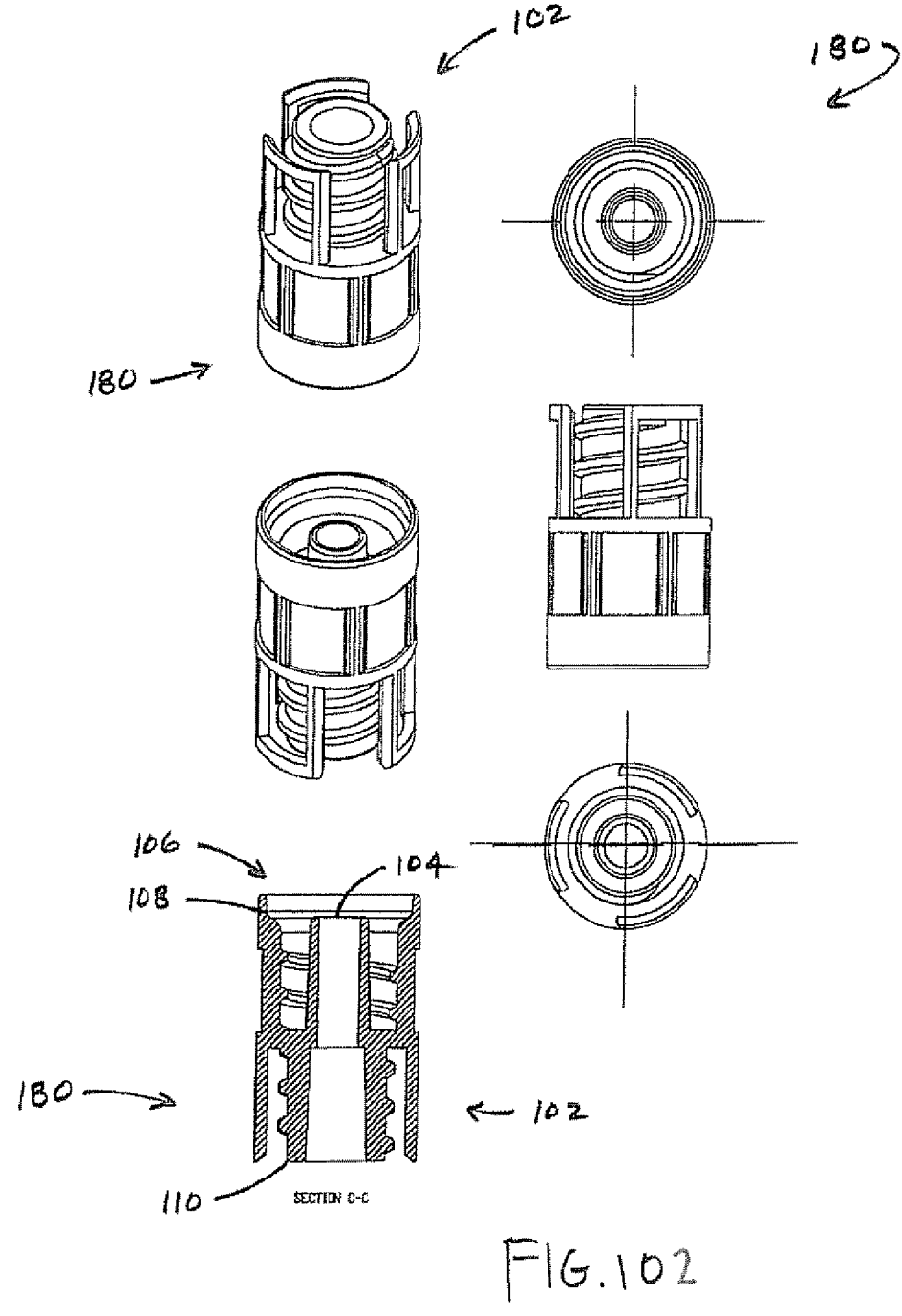
Figure 103:
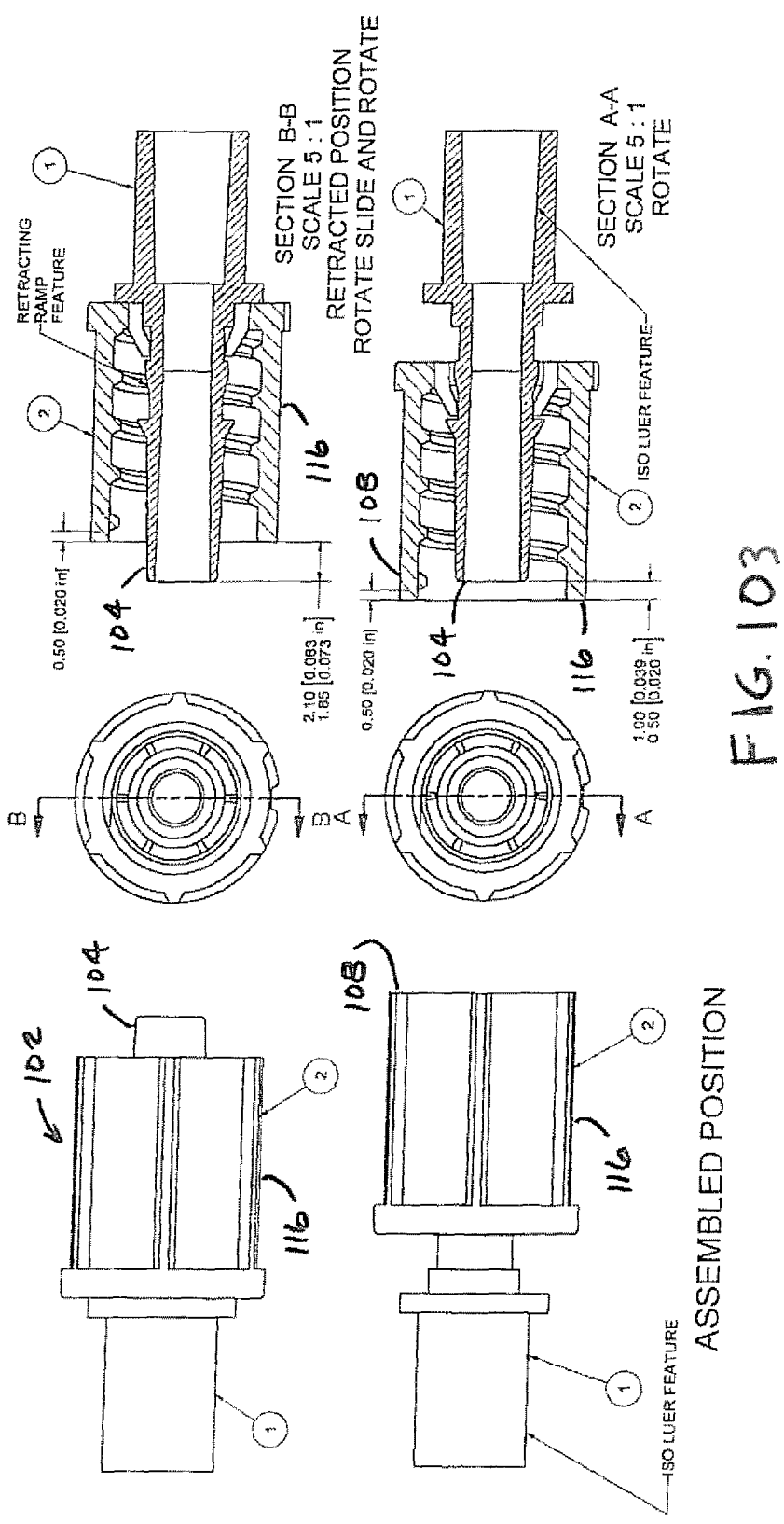
Figure 104:
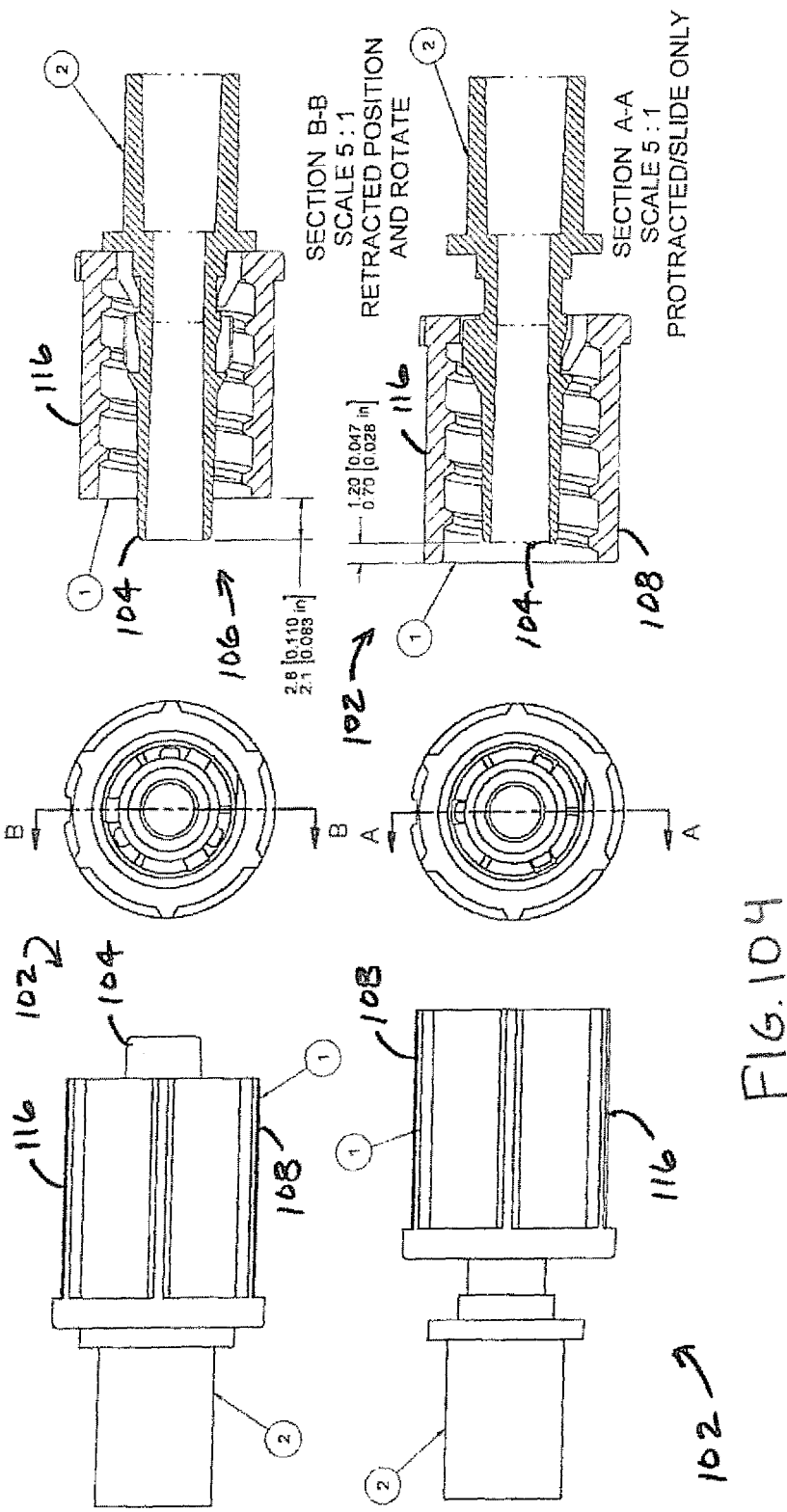
Figure 105:
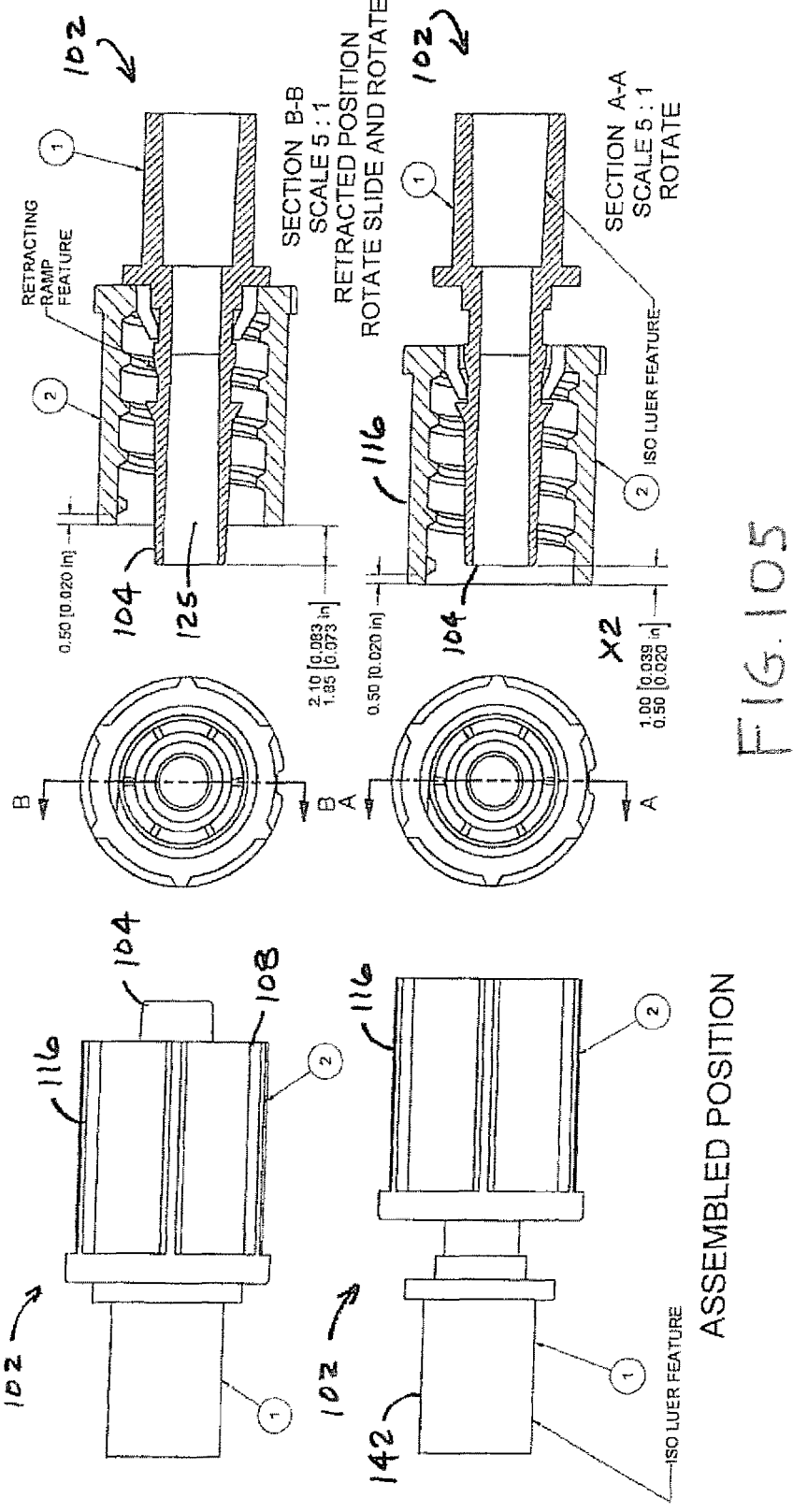
FIGS. 105-108 illustrate side, top, cross-sectional and perspective dimensioned drawings and supporting descriptions of additional reduced touch contamination devices, according to contemplated example embodiments of the present invention.
Figure 106:
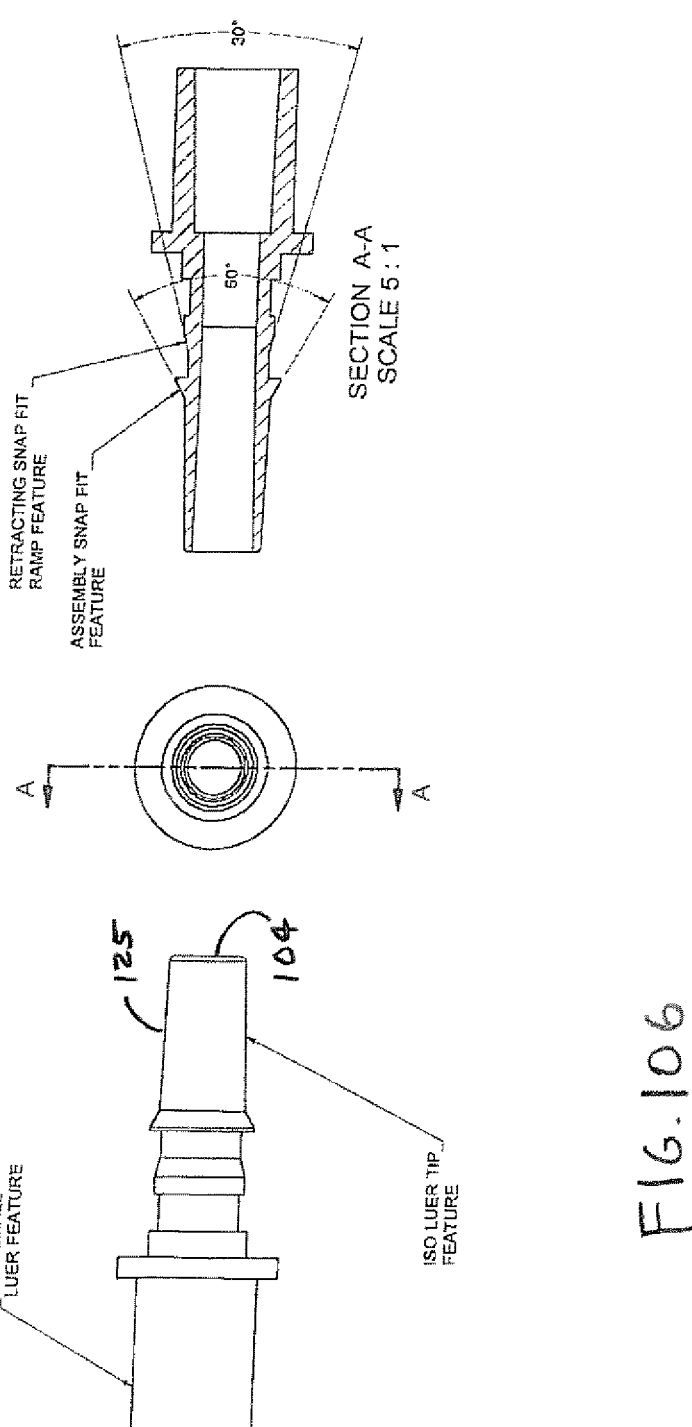
Figure 107:
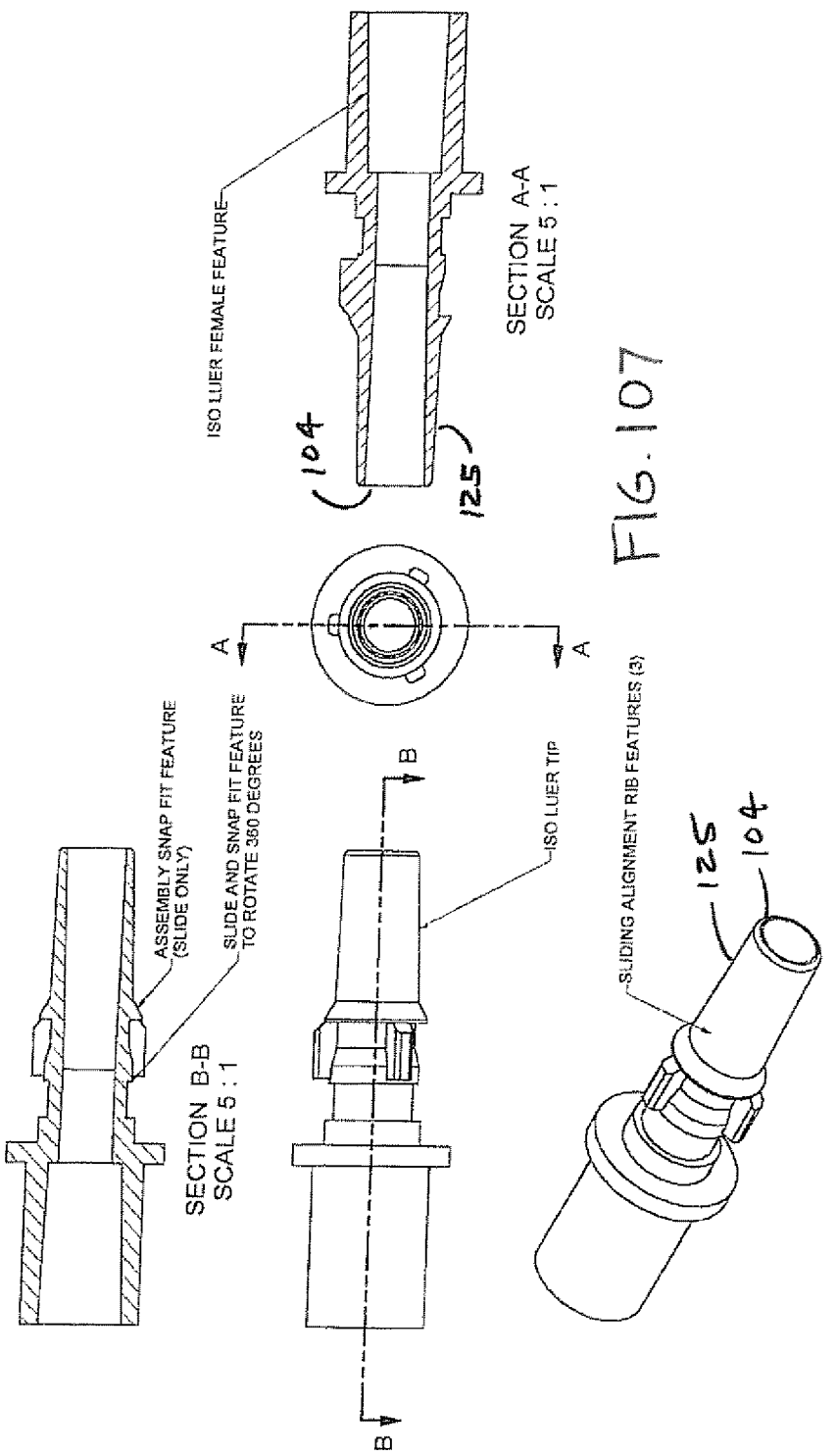
Figure 108:
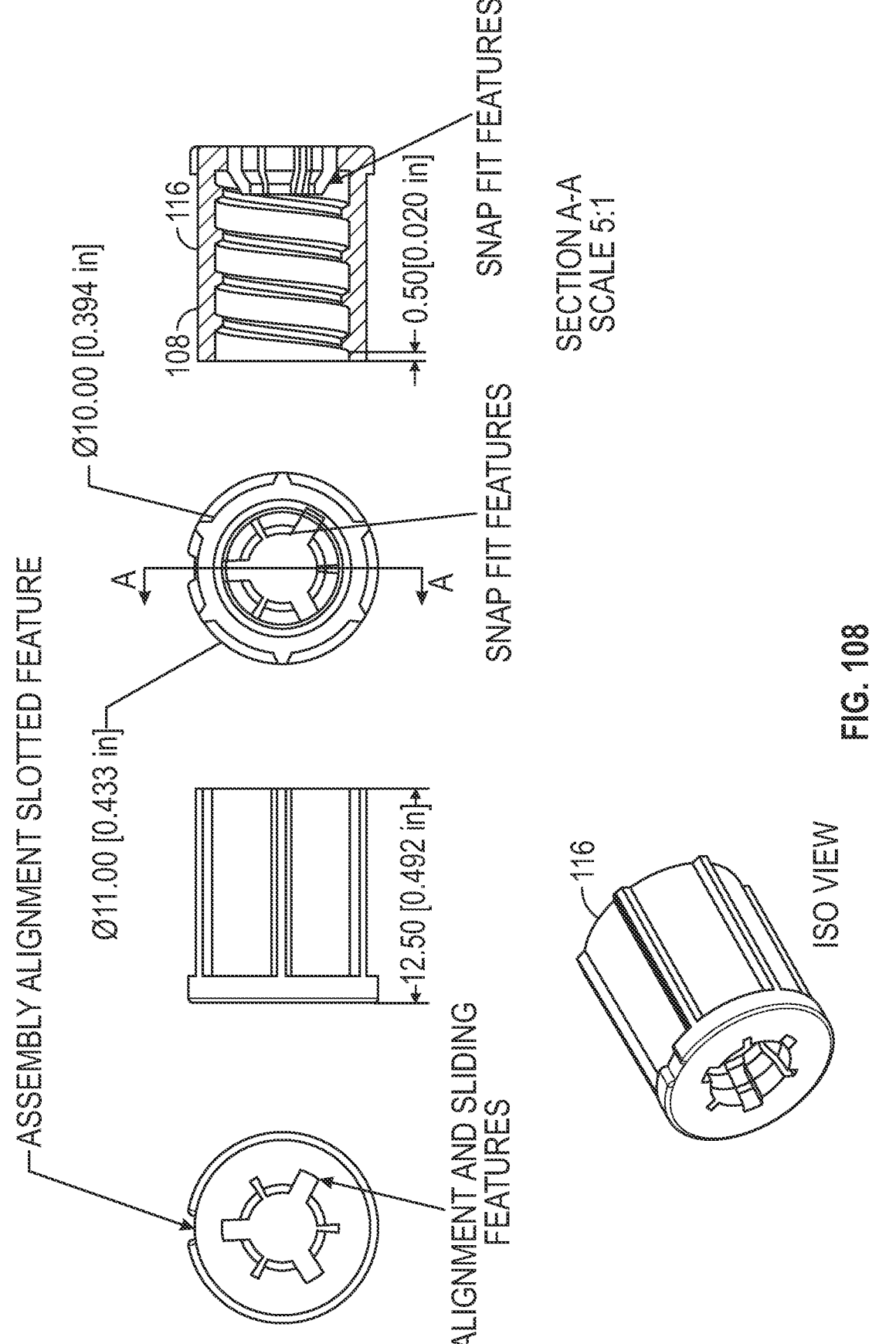

The reduced-touch contamination devices 102 preferably provide protections against contact contamination while maintaining full compatibility with ISO 594-1:2 Luer lock connector standards. This preferred feature of the present system is preferably enabled using one of several methodologies. First, the reduced-touch contamination devices 102 preferably comprise high levels of inherent compatibility with most ISO standard Luer lock connectors. For example, the ISO standard female Luer-type connector 210 of I.V. line 114 is directly compatible with the depicted reduced-touch contamination device 102. In alternate preferred implementation arrangements, any preferred embodiments of the present system that fall outside of the ISO dimensional requirements (to a degree that prevents the formation of a direct connection with a specific device) are preferably configured to be either removable from the Luer-containing devices, or alternately preferably, are immediately modifiable to a configuration that is equivalent to or closely matching ISO connection standard(s). In the lower depicted example of FIG. 2, reduced-touch contamination device 102 has been removed from existing medical product 103, thereby returning the medical device to full ISO-standard compatibility. Other example embodiments of the present system comprise removable shields, shields that are deformable away from extending male distal tip 104, and/or are movable relative to male distal tip 104/collar to allow the devices to achieved ISO-standard compatibility (see FIGS. 7-110 for example embodiments, 102 is used to generally represent the example shields).

Figure 3:
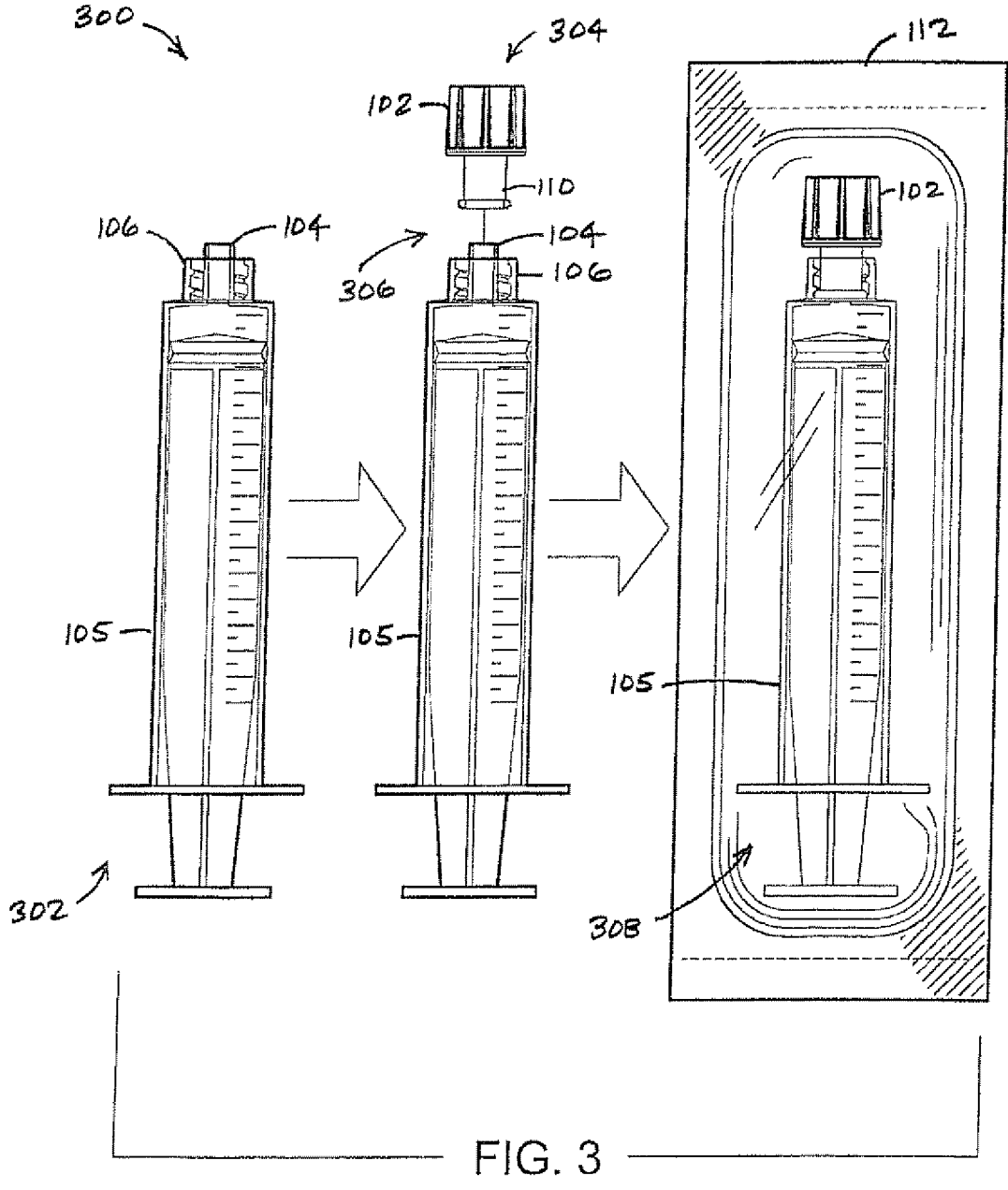
FIG. 3 shows a sequence of side views, illustrating a process of implementing and packaging the reduced-touch contamination device of FIG. 1B within an existing medical product having the Luer-type connector of FIG. 1A.

FIG. 3 shows a sequence of side views, illustrating a preferred implementation of the reduced-touch contamination device 102 within the existing medical device 103 having an existing Luer-type connector 107, according to one preferred embodiment of the present invention. In the example implementation of FIG. 3, the depicted medical device is the existing medical product 103, preferably comprising a medical syringe (empty or pre-filled). It should be noted that alternate preferred Luer-containing medical devices include I.V. lines (see FIG. 2), medical valves, medical adapters, etc.

Example embodiments of the present invention are preferably supplied in bulk quantity for combining with medical devices 103 (each medical device 103 including a standard male Luer-type connector 106 having a standard male distal tip 104 to be protected from contamination when being connected to a female Luer-type connector). Preferably, the reduced-touch contamination device 102 (at least embodying herein contamination shields) are assembled to medical device 103 in an arrangement that reduces contamination of male distal tip 104 when the tip is exposed, for example, prior to being connected to a female Luer-type connector 110 (see FIG. 2).

In one example arrangement of the present system, assembly is performed by the manufacturer/supplier of medical device 103. Once assembled, the bulk quantity of combined apparatus are preferably sterilized (if required) and placed in sterile medical packaging 112, as shown. In one preferred arrangement of the present system, packaging is performed by the manufacturer/supplier of medical device 103. This system preference provides a bulk quantity of modified medical devices 103 within sterile medical packaging 112, as shown, which are preferably distributed to care provider for use in patient treatment.

In accordance with the above-described preferred embodiment arrangements, there is thus provided method 300, related to patient treatment, such preferred method comprising the following steps. In initial preferred step 302, a first bulk quantity of medical devices 103 is preferably provided, wherein the first bulk quantity comprises a set of medical devices 103 having male Luer-type connectors. As previously described, each male Luer-type connector preferably comprises a male distal tip 104 (see FIG. 1A) that is to be protected from contamination when being connected to a female Luer-type connector.

In subsequent preferred step 304, a second bulk quantity consisting of reduced-touch contamination devices 102 (at least embodying herein contamination shields) is provided, as shown. Preferably, each device of such second bulk quantity is preferably configured to be placeable upon the medical device of the first bulk quantity, as shown. Preferably, each device of such second bulk quantity is configured such that, when placed in position on the first bulk quantity of medical devices 103, the combined apparatus preferably allows for reducing contamination potential of the male Luer-type connectors.

In subsequent preferred step 306, each of such second bulk quantity (i.e., contamination shields) is preferably placed upon each of the first bulk quantity (i.e, Luer-containing medical devices 103), providing a third bulk quantity comprising the combined elements. In subsequent preferred step 308, each of the third bulk quantity is preferably sterilized and then preferably packaged to provide a fourth bulk quantity comprising sterile packages 112 containing the combined apparatus. In a subsequent preferred step, the fourth bulk quantity of sterile packages is preferably made available for use in patient treatment. Upon reading this specification, those with ordinary skill in the art will now appreciate that, under appropriate circumstances, considering such issues as design preference, user preferences, distribution requirements, cost, production requirements, available materials, technological advances, etc., other manufacturing arrangements such as, for example, dividing steps between several cooperating entities, etc., may suffice.

Alternately preferably, reduced-touch contamination devices 102 are sold individually for attachment to user-selected medical devices 103. In this alternate preferred arrangement, individual reduced-touch contamination devices 102 are placed in sterile packages 112 made available for use in patient treatment.

Figure 4:
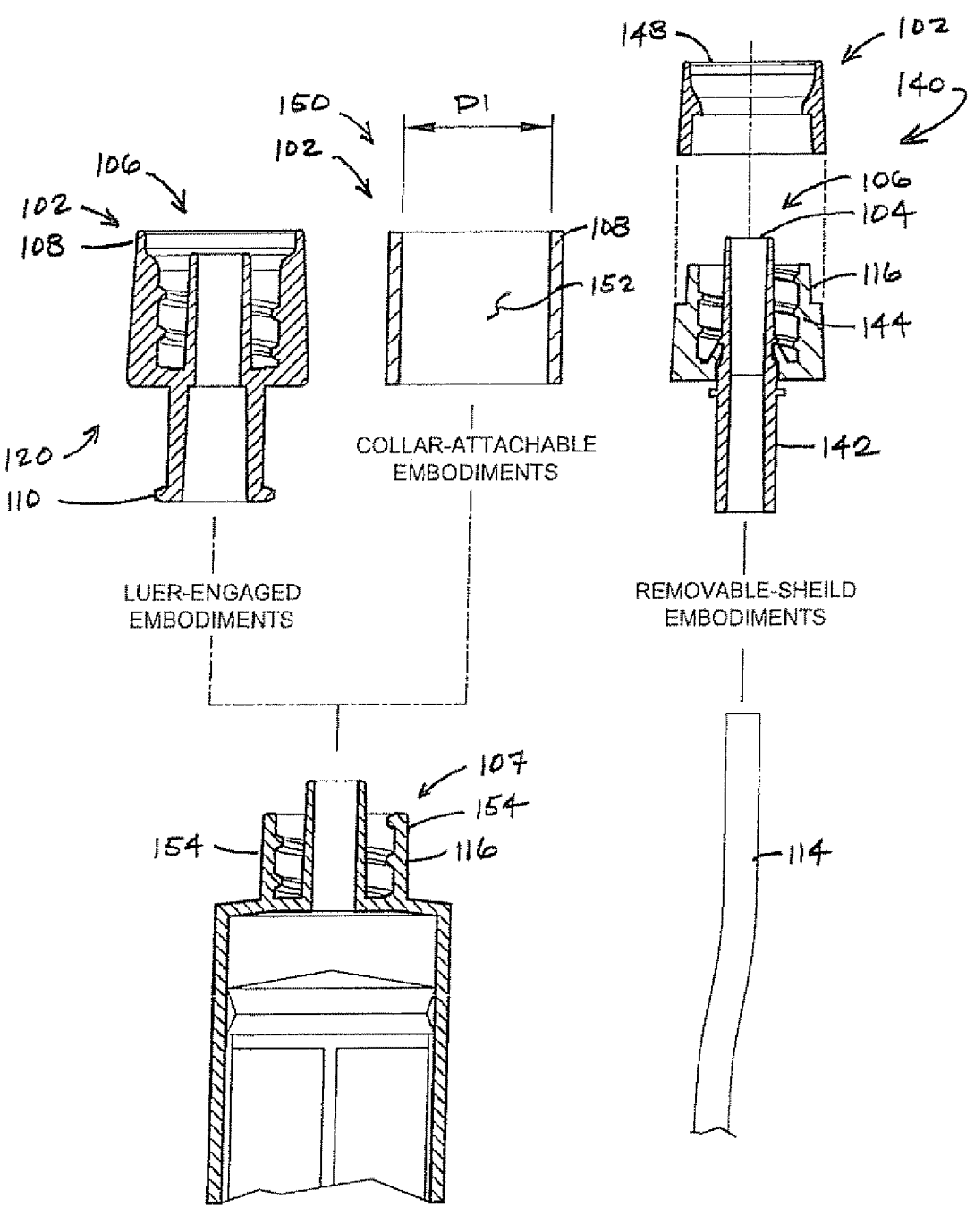
FIG. 4 shows cross-sectional views of the reduced-touch contamination device of FIG. 1B viewed along line 5-5, and two other different reduced-touch contamination devices, an attachable collar and removable shield, according to alternative example embodiments of the present invention, shown in comparison with the existing medical products of FIG. 1A and FIG. 2.

FIG. 4 shows a group of sectional views, illustrating preferred reduced-touch contamination devices 102, 102, 102, according to example embodiments of the present invention. Preferred configurations of reduced-touch contamination devices 102, 102, 102 fall within several principal categories, identified herein as Luer-engaged embodiments 120, collar-attachable embodiments 150, and removable-shield embodiments 140.

Generally stated, Luer-engaged embodiments 120 comprise a range of preformed adapters that are preferably configured to modify an existing Luer device by engaging directly the male connector assembly (and sometimes female) of a Luer-type connector (see FIGS. 7-19 and 50-74, and the preferred embodiment-feature combinations of Table 1 below). Each Luer-engaged embodiment 120 comprises a shielded male Luer-type connector 106 and a second female Luer-type connector 110 in fluid communication with the male Luer-type connector. Preferably, such second female Luer-type connector 110 is configured to be removably engagable with compatible male Luer-type connectors.

Preferred Luer-engaged embodiments 120 comprise single unitary moldings, as shown. Upon reading this specification, those with ordinary skill in the art will now appreciate that, under appropriate circumstances, considering such issues as design preference, user preferences, marketing preferences, cost, structural requirements, available materials, technological advances, etc., other shield arrangements such as, for example, multi-part assemblies combining an ISO-standard compatible Luer fitting with a non-integral shield s, non-integral shields including retractable features, removable features, resilient features, co-molded features, etc., may suffice.

Alternately preferably, Luer-engaged embodiments 120 comprise shielded female Luer-type connectors 180 having a second male Luer-type connector 106 in fluid communication (see FIGS. 98-104). Preferably, such second male Luer-type connectors 106 are configured to be removably engagable with compatible female Luer-type connectors.

Additional preferred features of Luer-engaged embodiment 120 are listed in Table 1.

TABLE 1

| LUER-ENGAGED EMBODIMENTS |
| --- |
| Features/Applications |

Shield distal periphery terminates beyond Luer tip
Rigid composition
Transparent composition
Opaque composition
Color-coded shields/bodies
Adapted to male Luer connector
Adapted to female Luer connector
Rotatable shield/collar
Fixed shield/collar
Shield is movable relative to tip/collar
Movable shield includes biasing spring
Shield includes funnel-shaped guide
Continuous shield wall
Discontinuous shield wall - perforated
Discontinuous shield wall - castellated
Two-part unit with rigid removable shield
Two-part with resilient removable shield
Two-part unit with fixed shield deformable away from tip/collar
Internal threads extend full shield length
Shield moves relative to tip and is rotatable
Shield moves relative to tip and is rotatable and collar starts in shielded position
devices has shielded male and female ends
devices has shielded male and female ends that are removable
internal threads do not extend the full shield length
Internal threads extend full shield length and can engage and stabilize without activating a needleless IV port "Clave ®" adapter
removable thread connection (it is noted that not all embodiments of the present system comprise a threaded connection)
removable non-threaded connection (slip fit Luers)

Example collar-attachable embodiments 150 preferably comprise a range of attachable/removable reduced-touch contamination devices 102 preferably configured to modify an existing Luer device by engaging the outer circumferential face of the Luer locking collar 116 in at least one position protectively surrounding the male Luer tip (and sometimes female) portion of the existing Luer device. Example collar-attachable embodiments 150 preferably comprise a continuous cylindrical member forming a shield 108 having an inner bore 152 configured to engage outer cylindrical wall portion 154 of the Luer locking collar 116 (see FIGS. 20-49 and the preferred embodiment feature-combinations of Table 2).

Preferably, example collar-attachable shields 108, when removably engaged about Luer locking collar 116, are configured to extend distally beyond Luer locking collar 116 and male distal tip 104 (see FIG. 51B). Preferred collar-attachable shields 108 are configured to protect male distal tip 104 by extending portions of shield 108 beyond Luer locking collar 116 a distance X2 of between about 2.1 mm and about 3.6 mm, thus reducing fluid-path contamination potential. Preferred collar-attachable shields 108 comprise an overall longitudinal length of less than about ¾ inch. Preferably, the outer wall (excluding projecting wall features) does not extend beyond a radius of about 0.4 inch from the longitudinal axis of the connector. Upon reading this specification, those with ordinary skill in the art will now appreciate that, under appropriate circumstances, considering such issues as design preference, user preferences, type of medical device, cost, structural requirements, available materials, technological advances, etc., other dimensional arrangements such as, for example, thicker walls, longer shields, non-circular shaped, etc., may suffice.

Preferably, shield 108 does not obstruct connections between male distal tip 104 and compatible female connectors. If shield 108 obstructs the connection of a specific Luer device, the reduced-touch contamination device 102 is removable from the medical device, thereby returning the medical device to full ISO-standard compatibility (at least embodying herein wherein such shield is removable from such medical device).

Preferably, collar-attachable shields 108 comprise an inner diameter D1 closely matching the outer diameter D2 of outer cylindrical wall portion 154 of the Luer locking collar 116. Preferred collar-attachable shields 108 comprise an inner diameter D1 of between about ⅜ inch and about ¾ inch with about ⅜ inch being preferred for Luer collars 116 meeting ISO standards.

Preferred collar-attachable embodiments 150 of the present system include extruded and molded circular embodiments, extruded and molded elliptical embodiments configured to "self-grip" onto the Luer lock collar to allow for some variation in Luer collar diameters (preferably increasing size compatability). Also, squeezing the widest portion of elliptical embodiments causes the device to "ungrip" on the shorter/tighter sides. Preferred embodiments preferably locate grips at the preferred "squeeze" points (see FIGS. 20-49)

Preferred collar-attachable embodiments 150 comprise overlapping coiled walls (see FIGS. 20-49). This preferred variation provides a "self gripping" function and is preferably manufactured using an extrusion process.

Preferred collar-attachable embodiments 150 comprise "C" shaped segments (see FIGS. 20-49), spiraled tubing, or frangible tubing that are preferably open, or can be opened, and therefore can be removed from existing Luer-type connector 107 by sliding over the tip before attachment AND by movement away from the longitudinal axis of the connector when a male and female Luer are being joined.

Preferred collar-attachable embodiments 150 are configured to expand or deflect away from the connector assembly if the shield's protective position obstructs the connection. In some preferred embodiments, shield 108 is retained in the shielding position; in other preferred embodiments, the device is configured to "pop off" Luer locking collar 116. Additional preferred features of collar-attachable embodiments 150 are listed in Table 2.

TABLE 2

| COLLAR-ATTACHABLE EMBODIMENTS<br>Features/Applications |
| --- |
| Shield distal periphery terminates beyond Luer tip |
| Extruded unit |
| Molded unit |
| Rigid composition |
| Resilient composition |
| Circular shape |
| Non-circular shape (oval and C-shaped) |
| Cut (Spiral) shape |
| Shield includes funnel-shaped guide |
| Shield is deformable away from device collar |
| Shield is movable along device collar |
| Movable shield includes positioning tab |
| Movable shield includes biasing spring |
| Shield is bonded or over-molded |
| Transparent compositions |
| Opaque compositions |
| Shield is adhered film |
| Shield is hinged |
| Ribbed shield |
| Tear-away (frangible) shield |
| Continuous shield wall |
| Discontinuous shield wall |
| Non-Syringe applications |
| IV tubing and extension sets |
| Port adapters and valved adapters (e.g."Clave[(R)]", "PRN"/needleless adapters) |
| Stopcocks |
| Blood-collection connectors |
| Needle and IV catheter hubs (for female connectors) |
| Moveable shield is a spring |
| Color-coded shields/bodies (preferred safety feature to distinguish syringes or IV lines with different drugs) |
| Shield comprises indicia/or a label (same as above including giving directions) |
| Shield is transferable between a male and female end |
| Includes an end cap to protect open tip in addition to collar |
| Attached on prefilled syringe |
| Shield has wider distal opening than standard Luer opening (8 mm) (provides improved attachment guide and targeting) |
| Various length specifications low profile |
| Kits |
| Packaged together in sterile packaging |
| Removable configuration with shielded portion in first provided position |
| Removable configuration with unshielded portion in first position |
| With truncated tip (accommodates longer shield in limited space) |
| Removable |
| Removable once connectors are mating (removable from side) |
| Not excessively long that connector "bottoms out" or connection is too deeply recessed after connection |

As previously indicated, it is sometimes advantageous to have a male Luer lock with a rotating Luer locking collar 116. This is particularly true when the reduced-touch contamination device is attaching to the female hub of a device that is difficult to twist during the connection phase. For example, when connecting a male Luer to a female hub of an I.V. catheter, the I.V. catheter ideally should not be turned to make a connection as the twisting action could dislodge the placement. Another possible complication with twisting the I.V. catheter is that it would require lifting the hand applying pressure to a vein to prevent backflow of blood;

and lifting the hand to perform this twisting manipulation could cause blood to flow from the vein to the skin resulting in a biohazard. For this reason, applicant has developed reduced-touch contamination device with rotating Luer locking collar. No existing Luer locks with rotating collars have a shield to protect the tip of the male Luer; therefore, these devices are prone to contamination during the connection phase. Some male rotating Luer locks even have retractable collars, which allow the collar to be pulled back exposing not only the tip of the male Luer but the entire connector. While this may make visualization of the tip and the initial slip fit easier, it leaves the male Luer completely exposed and the patient at more risk for direct contamination into the intravenous fluid path. While some of these connectors are retractable, when in the forward position the Luer collar never projects past the male Luer tip to shield it from contamination.

Preferred reduced-touch contamination devices of the present system comprise a rotating Luer lock with a shield that extends beyond the tip of a male Luer connector and protects the tip of a male Luer. Preferred reduced-touch contamination devices of the present system comprise a rotating Luer lock with a retractable shield that extends beyond the tip of a male Luer connector and protects the tip of a male Luer.

Preferred reduced-touch contamination devices of the present system comprise two parts assembled that include a male Luer connector which can engage a rotating Luer lock, a Luer lock that can rotate on the male Luer connector with an extended shield. While such a system would significant advantageous over the prior art there might be times where the shield extending beyond the tip would interfere with the connection with a female type hub as described earlier in the specification. One preferred means for overcoming this problem is to have at least two parts assembled that include a male Luer connector, which can engage a rotating Luer lock, a Luer lock that can rotate on the male Luer connector with an alterable shield; the alterable shield portion being deformable, retractable, or be alterable in similar ways.

Another preferred means for overcoming this problem is to have at least two parts assembled that include a male Luer connector which can engage a rotating Luer lock, a Luer lock that can rotate on the male Luer connector, and a shield with dimensions that would not be likely to interfere with female connectors, with properties such as a relatively short length beyond the shield tip or with a shield that is wider than the base of female connector with a wide base that might interfere with the shield.

Another preferred option is to have a Luer locking collar 116 that can be positioned in a forward position as a shield and can be retractable along the longitudinal axis 109 of the male Luer connector so that the collar is no longer in a forward shielded position. Another preferred way to overcome this problem is to have three parts assembled that include a male Luer connector which can engage a rotating Luer lock, a Luer lock that can rotate on the male Luer connector, and a removable shield.

As depicted in FIG. 4, example removable-shield embodiments 140 preferably comprise a male Luer-lock-type connector 106 having an ISO standard Luer locking collar and ISO standard male distal tip 104 extending along longitudinal axis and to be protected from contamination when exposed. Removable-shield embodiments 140 preferably comprise at least one other fluid-conducting connector 142 in fluid communication with such male Luer-type connector 106. Preferred fluid-conducting connectors 142 comprise features preventing rotation or removal of the connector, for example, I.V. tubing connections (as shown), tubing barb connections, and similar fixed tubing features/fittings.

Preferably, Luer locking collar 116 comprises an ISO-standard locking portion 144 and an removable shield portion 148, such shield portion 148 being configured to shield such male distal tip to reduce contamination potential (see FIG. 1A). Preferably Luer locking collar 116 is configured to be rotatable to assist connection to a compatible locking Luer device. Preferably, shield portion 148 does not obstruct connections between male distal tip 104 and compatible female connectors. If shield portion 148 obstructs the connection of a specific Luer device, shield portion 148 is removed from reduced-touch contamination device 102, thereby bringing reduced-touch contamination device 102 to full ISO-standard conformance (at least embodying herein wherein such shield is removable from such medical device). Upon reading this specification, those with ordinary skill in the art will now appreciate that, under appropriate circumstances, considering such issues as design preference, user preferences, marketing preferences, cost, structural requirements, available materials, technological advances, etc., other shield arrangements such as, for example, retractable shield, etc., may suffice.

Additional preferred features of removable-shield embodiments 140 are listed in Table 3.

TABLE 3

REMOVABLE-SHIELD EMBODIMENTS
Features/Applications

Shield distal periphery terminates beyond Luer tip
Rigid composition
Transparent composition
Opaque composition
Color-coded shields/bodies
Adapted to male Luer connector
Adapted to female Luer connector
Rotatable shield/collar
Shield is movable relative to tip/collar
Movable shield includes biasing spring
Shield includes funnel-shaped guide
Continuous shield wall
Discontinuous shield wall - perforated
Discontinuous shield wall - castellated
Two-part unit with rigid removable shield
Two-part with resilient removable shield
Two-part unit with fixed shield deformable away from tip/collar
Internal threads extend full shield length
Shield moves relative to tip and is rotatable
Shield moves relative to tip and is rotatable and collar starts in shielded position
devices has shielded male and female ends
devices has shielded male and female ends that are removable
internal threads do not extend the full shield length
Internal threads extend full shield length and can engage and stabilize without activating a needleless IV port "Clave ®" adapter
removable thread connection (it is noted that not all embodiments of the present system comprise a threaded connection)
removable non-threaded connection (slip fit Luers)

Figures 5A, 5B:
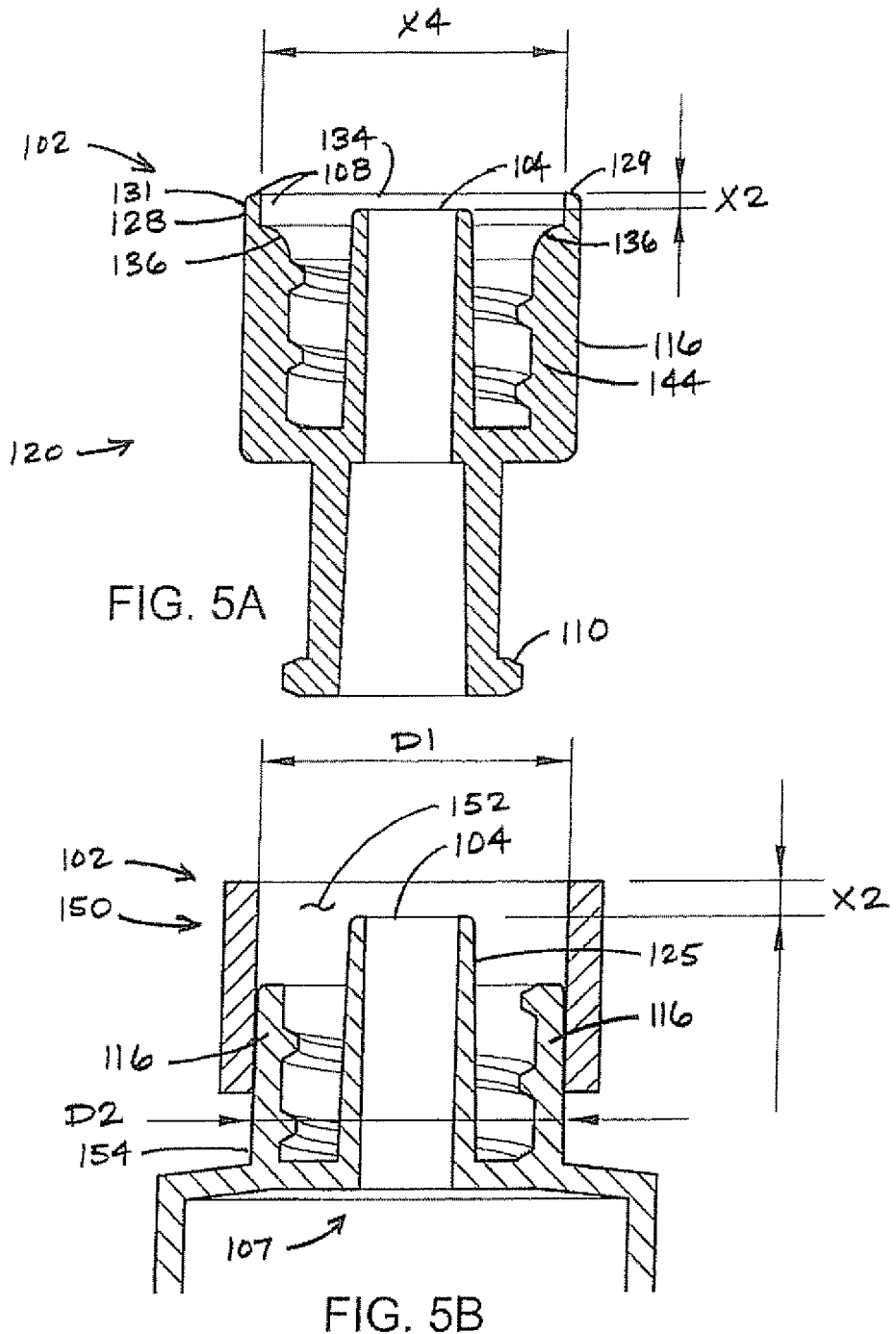
FIG. 5A shows an enlarged cross-sectional view of the reduced-touch contamination device of FIG. 1B viewed along line 5-5.
FIG. 5B shows a diagrammatic cross-sectional view of the attachable collar reduced-touch contamination device of FIG. 4 secured around the male Luer-type connector the existing medical product of FIG. 2.

FIG. 5A shows the sectional view 5-5 of FIG. 1B, illustrating preferred geometric configurations of reduced-touch contamination devices 102, according to preferred Luer-engaging embodiments 120 of the present invention. In preferred embodiments of the present system, the outer Luer locking collar 116 of reduced-touch contamination device 102 forms shield 108, as shown. More specifically, Luer locking collar 116 preferably comprises an ISO-standard locking portion 144 and an integral shield portion 128, as shown. Preferably, integral shield portion 128 extends beyond male distal tip 104 and shields contact between non-sterile surfaces and the sterile male distal tip 104 of the Luer connector.

Preferably, integral shield portion 128 comprises a distal terminating portion 129 comprising a continuous periphery 131, as shown. Continuous periphery 131 preferably extends the above-defined distance X2 beyond male distal tip 104, as shown, forming distal portion 134. In the embodiment of FIG. 5A, distal portion 134 of integral shield portion 128 comprises one unitary structure of a generally cylindrical transverse cross section, as shown. Preferably, integral shield portion 128 does not obstruct connection of compatible Luer connectors.

In addition, the internal bore of distal portion 134 comprises a funnel-like guide 136 configured to assist guiding a female Luer-type connector toward male distal tip 104. Preferably, funnel-like guide 136 does not obstruct the connection of a female Luer-type connector with male distal tip 104. Upon reading this specification, those with ordinary skill in the art will now appreciate that, under appropriate circumstances, considering such issues as design preference, user preferences, marketing preferences, cost, structural requirements, available materials, technological advances, etc., other shield-portion arrangements such as, for example, discontinuous shields, perforated shields, asymmetrical shields, non-circular shields, etc., may suffice.

Reduced-touch contamination device 102 of FIG. 5A further comprises female Luer-type connector 110, as shown. Female Luer-type connector 110 preferably comprises ISO standard female Luer dimensions. It is noted that alternate preferred embodiments of the present invention include shields (see FIGS. 50-74).

As noted in Table 1, preferred embodiments of the present system have shields that comprise transparent portions to allow visualization of the engagement of the male and female connectors. Preferred bodies of reduced-touch contamination devices comprise transparent elements to allow visualization of flow to allow differentiation of different fluids, gases and solids and determine fluid directional flow in this critical region. Preferred embodiments of the present system comprise shielded connectors that comprise low profiles for compatibility with intravascular applications, thereby removing the risks of malfunction of such devices. Preferred embodiments of the present system are universally compatible with current Luer connectors used for intravascular access (not just a preselected, pre-supplied proprietary connector for continuous ambulatory peritoneal dialysis). Preferred embodiments of the present system are adapted to intravascular access, such as devices that comprise a distal intravenous catheter and a proximal IV solution source.

Figure 6:
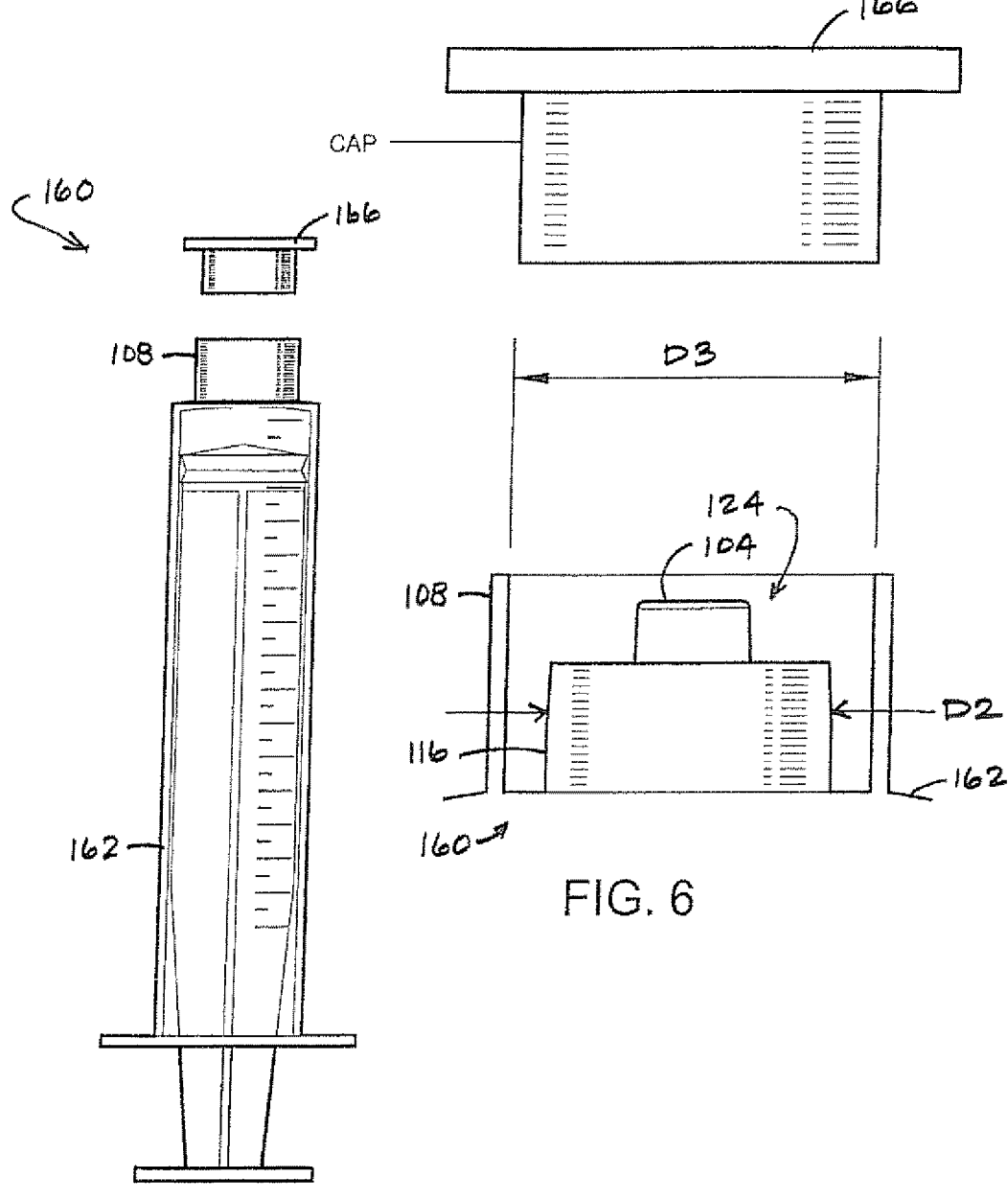
FIG. 6 shows a side view and enlarged isolated view of a reduced-touch contamination device with a fixed shield, integrated within a medical device, according to another contemplated example embodiment of the present invention.

FIG. 6 shows a side view of an alternate preferred reduced-touch contamination device 160 integrated within a fluid-delivery medical device 162, according to another preferred embodiment of the present invention. Reduced-touch contamination device 160 preferably comprises male Luer-type connector 124 protected by a fixed integral shield 108, as shown. Shield 108 preferably extends beyond male distal tip 104 and shields contact between non-sterile surfaces and the sterile male distal tip 104 of the Luer connector. Shield 108 preferably comprises an inner diameter D3 larger than the outer diameter D2 of outer cylindrical wall portion 154 of the Luer locking collar 116. This preferred arrangement protects male distal tip 104 without interfering with connections with other Luer-engaged devices. Preferred integral shields 108 comprise an inner diameter D3 of less than about ¾ inch. Alternate preferred reduced-touch contamination device 160 may be fitted with cap 166 in pre-filled syringe applications. In this preferred arrangement, shield 108 can preferably function as a positioning/stabilizing receiver for cap 166.

FIGS. 105-108 includes drawings and supporting descriptions of additional preferred embodiments of the present system. The preferred embodiments of FIGS. 105-110 comprise axially-translating and rotating Luer locking collars 116 having at least one tip-protecting position (preferably configured to shield male distal tip 104) and at least one tip-exposed position configured provide exposed access to male distal tip 104 to provide unobstructed access to male distal tip 104 when being connected to a compatible female connector. An additional "retracting-shield" embodiment is shown in FIGS. 50-74.

Since a male Luer locking collar in a forward shielding position would have additional threads, for some clinicians using the product, they may be familiar with a small number of turns being necessary to lock the female connector over the male connector. They would have to rotate the collar more times than usual to stabilize. It might occur that some would engage the female hub and turn the rotating Luer locking collar the customary number of times for a standard device and not make the full number of turns required. The male and female connectors might not be connected or might come loose.

There are several preferred solutions to this issue. In preferred embodiments of the present system, a rotating collar is rotatable in a forward position that is preferably stable along the longitudinal axis of the male connector that shields the male connector tip. Preferably, the rotating collar is functional for connections in such a forward position. Preferably, the rotating collar is also configured to be slid along longitudinal axis into a retracted position that would place the male Luer tip in a more standard position relative to the rotating collar. Preferably, the shield is configured to be stable in the retracted position where it would rotate in same position along the longitudinal axis after "clicking" into position. Alternatively, the shield in the retracted position preferably continues to be slid forward and backward along the longitudinal axis. While there are advantages to having a retractable shield that is in a stable position or freely slideable along the longitudinal axis, in both cases it is preferred that the collar has a limiter that prevents forward movement while in the retracted position in order to engage, rotate and lock a female type hub with a male Luer connector.

In some preferred embodiments, at least one of the tip-protected position or tip-exposed position limits rotation of locking collar. For example, preferred embodiments comprise a "collar-forward" (protected) position wherein Luer locking collar is non-rotatable (however, preferably configured to shield male distal tip). To engage a compatible female connector on the male 6% conical fitting, Luer locking collar must be pushed back to a freely-rotating second position. To achieve the second position, allowing locking of the Luer fitting, the female connector must be fully engaged on the male 6% conical fitting. This preferred feature greatly reduces the chance of leakage at the fitting by allowing a lock only after the conical tapers are fully engaged.

In the above-described embodiment, the collar cannot rotate in a forward shielding position. When a female catheter hub engages the collar, it preferably pushes the male collar backwards from a non-spinning position until it snaps into a retracted position. Once in the retracted position the collar could then be spinnable along the longitudinal axis. The advantage of such a configuration is that the male connector tip would start in a shielded position. The user would need to push the collar backwards with the female hub to avoid problems with have extra turns (e.g. unfamiliarity with excess turns or leaking as described above). The male Luer tip preferably remains protected during the initial connection with a female hub and when the shield is being retracted, since the female hub would then already be enclosing the male tip. In these preferred configurations, the shield could be stable in the retracted position where it would rotate in same position along the longitudinal access after "clicking" into position for example. Alternatively, the shield in the retracted position could be slid forward and backward along the longitudinal axis of the connector. While there are advantages to have a retractable shield that is in a stable or freely slideable along the longitudinal axis, in both cases it would be desirable that the collar has a limiter that prevents forward movement while in the retracted position in order to engage, rotate and lock a female type hub with a male Luer connector.

It is apparent to those of ordinary skill in the art that the depictions of the described embodiments are only meant to be taken as examples through which the present invention may be implemented, and not to limit the invention. Any conceivable interface configuration may be employed within the capabilities of any device that will successfully implement the present invention while maintaining its overall spirit and concept.

While the invention has been shown and described in exemplary forms, it will be apparent to those skilled in the art that many modifications, additions, and deletions can be made therein without departing from the spirit and scope of the invention as defined by the following claims.

What is claimed is:

1. An apparatus configured to receive a female Luer connector, the apparatus comprising:

a male Luer connector comprising a conical connector and a circumferential collar oriented about a longitudinal axis, the conical connector comprising a proximal portion and a distal portion, the circumferential collar comprising a distal end and an inner surface, wherein:

the inner surface of the circumferential collar surrounds the proximal portion of the conical connector and does not surround the distal portion of the conical connector, and the inner surface of the circumferential collar is threaded and defined by a plurality of peaks and valleys; and a shield comprising a distal terminating periphery substantially surrounding the longitudinal axis at a distal end of the shield, the shield oriented about the longitudinal axis and surrounding the distal portion of the conical connector, wherein:

the shield extends beyond the distal portion of the conical connector;

the shield comprises an inner bore extending from the distal portion of the conical connector to the distal end of the shield, the inner bore of the shield having a diameter larger than a diameter of an inner bore of the circumferential collar;

the shield is positionally fixed relative to the circumferential collar;

the shield comprises a continuous inner surface; and the shield is an adhered film.

2. The apparatus of claim 1, wherein the shield is fixed to the circumferential collar.

3. The apparatus of claim 1, wherein the diameter of the inner bore of the shield is larger than an outer diameter of the circumferential collar.

4. The apparatus of claim 1, wherein an inner surface of the shield is threadless.

5. The apparatus of claim 1, wherein the diameter of the inner bore of the shield is greater than or equal to an outer diameter of the circumferential collar.

6. The apparatus of claim 1, wherein the shield does not extend beyond a radius of 0.4 inches from a longitudinal axis of the connector.

7. An apparatus configured to receive a female Luer connector, the apparatus comprising:

a male Luer connector comprising a conical connector and a circumferential collar oriented about a longitudinal axis; and a shield comprising an inner bore extending from a distal portion of the conical connector to a distal end of the shield and a distal terminating periphery at the distal end of the shield, the shield oriented about the longitudinal axis and surrounding the distal portion of the conical connector, and the distal terminating periphery extending beyond a distal end of the conical connector, wherein the shield comprises a continuous inner surface and the shield is frangible, and wherein the shield extends beyond the circumferential collar a distance of between 2.1 mm and 3.6 mm.

8. The apparatus of claim 7, wherein the apparatus is a syringe.

9. The apparatus of claim 7, wherein the apparatus is an adapter.

10. The apparatus of claim 7, wherein the distal terminating periphery surrounds the longitudinal axis.

11. The apparatus of claim 7, wherein the shield further comprises a funnel like guide, wherein the funnel like guide does not extend beyond a distal end of the circumferential collar.

12. The apparatus of claim 7, wherein an inner surface of the shield is ridgeless.

* * * * *